United States Patent
Haruyama et al.

(10) Patent No.: US 12,012,405 B2
(45) Date of Patent: Jun. 18, 2024

(54) COMPOUND, LIGHT-EMITTING DEVICE, LIGHT-EMITTING APPARATUS, ELECTRONIC DEVICE, AND LIGHTING DEVICE

(71) Applicant: Semiconductor Energy Laboratory Co., Ltd., Kanagawa-ken (JP)

(72) Inventors: Takuya Haruyama, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 668 days.

(21) Appl. No.: 17/133,254

(22) Filed: Dec. 23, 2020

(65) Prior Publication Data
US 2021/0206767 A1    Jul. 8, 2021

(30) Foreign Application Priority Data

Dec. 27, 2019 (JP) ................................. 2019-239346

(51) Int. Cl.
*H10K 85/60* (2023.01)
*C07C 211/61* (2006.01)
*C07D 471/14* (2006.01)

(52) U.S. Cl.
CPC ......... *C07D 471/14* (2013.01); *H10K 85/615* (2023.02); *H10K 85/633* (2023.02);
(Continued)

(58) Field of Classification Search
CPC ........................... C07C 15/28; C07C 2603/24
See application file for complete search history.

(56) References Cited

U.S. PATENT DOCUMENTS

| 4,188,401 A | 2/1980 | Brandes et al. |
| 5,759,444 A | 6/1998 | Enokida et al. |

(Continued)

FOREIGN PATENT DOCUMENTS

| EP | 1775334 A1 * | 4/2007 | ............ C09K 11/06 |
| JP | 2014-045179 A | 3/2014 | |

(Continued)

OTHER PUBLICATIONS

Shizu, K. et al., "Highly-efficient thermally-activated delayed-fluorescence (TADF) compounds by controlling HOMO-LUMO overlap density," Extended Abstracts (The 61th Spring Meeting 2014), the Japan Society of Applied Physics and Related Societies, Mar. 17, 2014, pp. 12-224.

(Continued)

*Primary Examiner* — Vu A Nguyen
(74) *Attorney, Agent, or Firm* — Husch Blackwell LLP

(57) ABSTRACT

A novel compound is provided. The novel compound is represented by General Formula (G1).

(Continued)

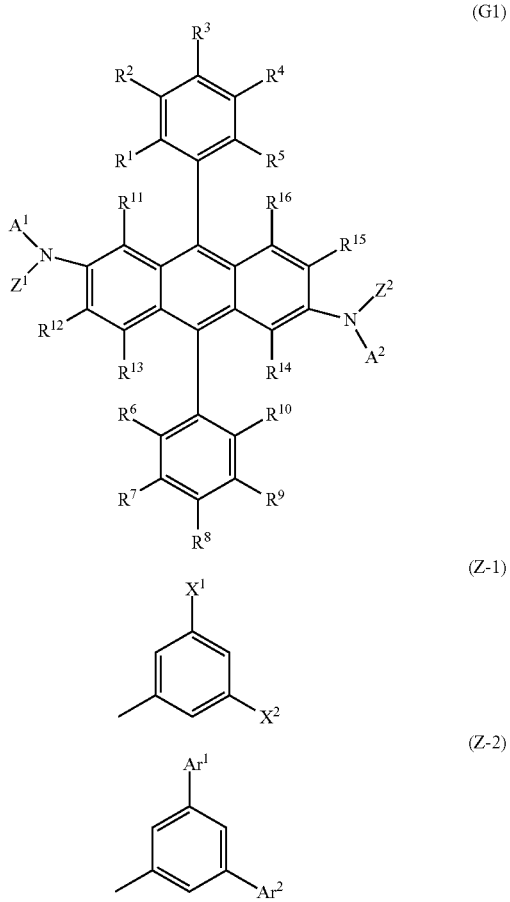

Each of $A^1$ and $A^2$ independently represents a substituted or unsubstituted condensed aromatic ring, a substituted or unsubstituted condensed heteroaromatic ring, or a structure represented by Formula (Z-1) or (Z-2); and each of $Z^1$ and $Z^2$ independently has a structure represented by Formula (Z-1) or (Z-2), Each of $X^1$ and $X^2$ independently represents any one of an alkyl group, a cycloalkyl group, a substituted or unsubstituted cycloalkyl group having a bridge structure, and a trialkylsilyl group. Each of $Ar^1$ and $Ar^2$ independently represents a substituted or unsubstituted aromatic hydrocarbon group, and at least one of $Ar^1$ and $Ar^2$ includes the same substituent as $X^1$. Each of $R^1$ to $R^{16}$ independently represents any one of hydrogen, an alkyl group, a substituted or unsubstituted cycloalkyl group, a trialkylsilyl group, and a substituted or unsubstituted aryl group.

20 Claims, 20 Drawing Sheets

(52) U.S. Cl.
CPC ..... *H10K 85/6572* (2023.02); *H10K 85/6574* (2023.02); *H10K 85/6576* (2023.02)

(56) References Cited

U.S. PATENT DOCUMENTS

| | | | |
|---|---|---|---|
| 6,376,107 | B1 | 4/2002 | Heuer et al. |
| 7,816,017 | B2 | 10/2010 | Funahashi et al. |
| 8,058,478 | B2 | 11/2011 | Funahashi et al. |
| 9,276,228 | B2 | 3/2016 | Seo et al. |
| 9,559,313 | B2 | 1/2017 | Seo et al. |
| 9,947,885 | B2 | 4/2018 | Seo et al. |
| 10,347,851 | B2 | 7/2019 | Lennartz et al. |
| 10,505,132 | B2 | 12/2019 | Seo et al. |
| 10,644,254 | B2 | 5/2020 | Seo et al. |
| 10,734,594 | B2 | 8/2020 | Seo et al. |
| 2006/0210830 | A1 | 9/2006 | Funahashi et al. |
| 2011/0034733 | A1 | 2/2011 | Funahashi et al. |
| 2014/0034930 | A1 | 2/2014 | Seo et al. |
| 2014/0117322 | A1 | 5/2014 | Seo et al. |
| 2016/0104847 | A1 | 4/2016 | Xia et al. |
| 2016/0172602 | A1 | 6/2016 | Ogiwara et al. |
| 2016/0315274 | A1 | 10/2016 | Lennartz et al. |
| 2019/0280236 | A1 | 9/2019 | Tabata et al. |
| 2020/0044165 | A1 | 2/2020 | Lennartz et al. |
| 2021/0043840 | A1 | 2/2021 | Seo et al. |
| 2021/0061753 | A1 | 3/2021 | Haruyama et al. |
| 2021/0066596 | A1 | 3/2021 | Haruyama et al. |

FOREIGN PATENT DOCUMENTS

| | | | | |
|---|---|---|---|---|
| KR | 2014-0142923 | A | | 12/2014 |
| KR | 20160059609 | A | * | 5/2016 ............. C09K 11/06 |

OTHER PUBLICATIONS

Nakanotani, H. et al., "High-efficiency organic light-emitting diodes with fluorescent emitters," Nature Communications, May 30, 2014, vol. 5, pp. 4016-1-4016-7.

Noda.H et al., "Excited state engineering for efficient reverse intersystem crossing", Science Advances, Jul. 22, 2018, vol. 4, No. 6, p. 6910.

* cited by examiner

COMPOUND, LIGHT-EMITTING DEVICE, LIGHT-EMITTING APPARATUS, ELECTRONIC DEVICE, AND LIGHTING DEVICE

BACKGROUND OF THE INVENTION

1. Field of the Invention

One embodiment of the present invention relates to a compound, a light-emitting device, a light-emitting apparatus, an electronic device, and a lighting device. Note that one embodiment of the present invention is not limited thereto. That is, one embodiment of the present invention relates to an object, a method, a manufacturing method, or a driving method. One embodiment of the present invention relates to a process, a machine, manufacture, or a composition of matter.

2. Description of the Related Art

In recent years, research and development of light-emitting devices using electroluminescence (EL) have been actively conducted. Such a light-emitting device has a structure in which an EL layer (containing a light-emitting substance) is provided between a pair of electrodes. In a light-emitting device, voltage application between the pair of electrodes causes, in the EL layer, recombination of electrons and holes injected from the electrodes, which brings the light-emitting substance (an organic compound) contained in the EL layer into an excited state. Light is emitted when the light-emitting substance returns to the ground state from the excited state. The excited state can be a singlet excited state (S*) and a triplet excited state (T*). Light emission from a singlet excited state is referred to as fluorescence, and light emission from a triplet excited state is referred to as phosphorescence. The statistical generation ratio in the light-emitting device is considered to be $S^*:T^*=1:3$. Therefore, a light-emitting device including a phosphorescent substance capable of converting triplet excitation energy into light emission has been actively researched and developed recently by way of obtaining high efficiency.

As a material capable of partly or entirely converting triplet excitation energy into light emission, a thermally activated delayed fluorescent (TADF) material is known in addition to a phosphorescent substance. A TADF material can generate a singlet excited state from a triplet excited state by reverse intersystem crossing.

Disclosed is a method for making a fluorescent substance emit light efficiently in a light-emitting device including a TADF material, in which the TADF material is combined with a fluorescent substance and the singlet excitation energy of the TADF material is transferred to the fluorescent substance (see Patent Document 1 and Non-Patent Document 1).

As for energy transfer from a host material to a guest material in a light-emitting layer of a light-emitting device, in general it is preferable that the concentration ratio of the guest material (fluorescent substance) to the host material be increased in order to increase the efficiency of energy transfer due to the Förster mechanism; however, it is known that there is a trade-off relationship: an increase in the concentration ratio of the guest material increases the rate of energy transfer due to the Dexter mechanism, which results in a decrease in the emission efficiency. Therefore, increasing the concentration ratio of the guest material has not been an effective means for improving the emission efficiency.

REFERENCE

Patent Document

[Patent Document 1] Japanese Published Patent Application No. 2014-045179

Non-Patent Document

[Non-Patent Document 1] Hiroki Noda et al., "SCIENCE ADVANCES", 2018, vol. 4, no. 6, eaao6910

SUMMARY OF THE INVENTION

One embodiment of the present invention provides a novel compound. One embodiment of the present invention provides a novel compound that efficiently receives energy from a singlet excited state (St) (hereinafter the energy is referred to as a singlet excitation energy) of a host material even when the concentration ratio of the guest material in an EL layer of a light-emitting device is increased, whereby the transfer of energy from a triplet excited state (P) (the energy is hereinafter referred to as a triplet excitation energy) of the host material is unlikely to occur (energy transfer due to the Dexter mechanism can be prevented).

Another embodiment of the present invention provides a novel compound that can be used in a light-emitting device. Another embodiment of the present invention provides a novel compound that can be used in an EL layer of a light-emitting device. Another embodiment of the present invention provides a novel light-emitting device with high emission efficiency with the use of the novel compound of one embodiment of the present invention. Another embodiment of the present invention provides a novel light-emitting apparatus, a novel electronic device, or a novel lighting device.

Note that the description of these objects does not disturb the existence of other objects. One embodiment of the present invention does not have to achieve all these objects. Other objects will be apparent from and can be derived from the description of the specification, the drawings, the claims, and the like.

One embodiment of the present invention is a fluorescent substance that is a compound represented by General formula (G1) below.

[Chemical Formula 1]

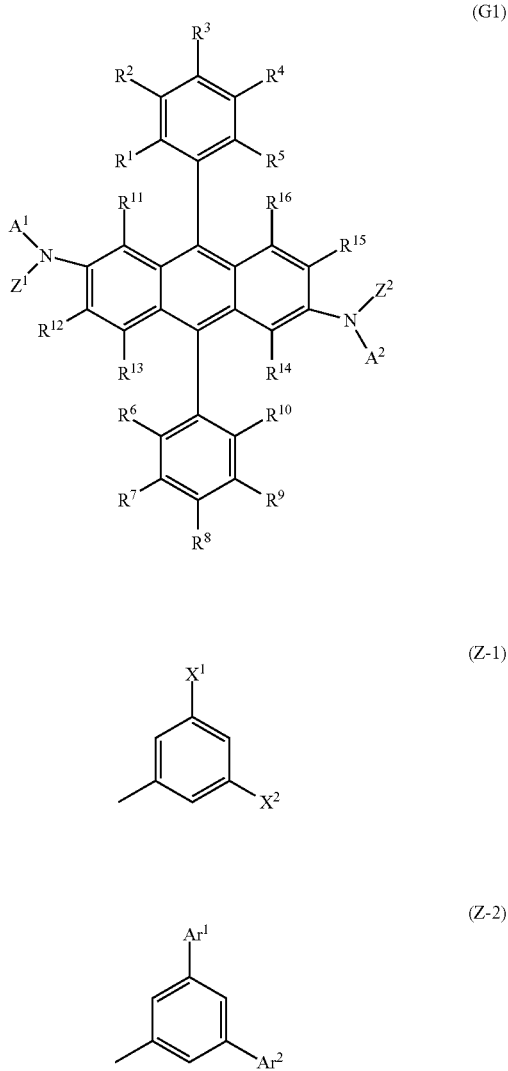

(G1)

(Z-1)

(Z-2)

In General Formula (G1), each of $A^1$ and $A^2$ independently represents a substituted or unsubstituted condensed aromatic ring having 10 to 30 carbon atoms, a substituted or unsubstituted condensed heteroaromatic ring having 3 to 30 carbon atoms, or a structure represented by General Formula (Z-1) or General Formula (Z-2); and each of $Z^1$ and $Z^2$ independently has a structure represented by General Formula (Z-1) or (Z-2). In General Formula (Z-1), each of $X^1$ and $X^2$ independently represents any one of an alkyl group having 3 to 10 carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms. Each of $Ar^1$ and $Ar^2$ independently represents a substituted or unsubstituted aromatic hydrocarbon group having 6 to 13 carbon atoms, and at least one of $Ar^1$ and $Ar^2$ includes the same substituent as $X^1$. Each of $R^1$ to $R^{16}$ independently represents any one of hydrogen, an alkyl group having 3 to 10 carbon atoms, a substituted or unsubstituted cycloalkyl group having 3 to 10 carbon atoms, a trialkylsilyl group having 3 to 12 carbon atoms, and a substituted or unsubstituted aryl group having 6 to 25 carbon atoms.

Another embodiment of the present invention is a compound represented by General Formula (G2) below.

[Chemical Formula 2]

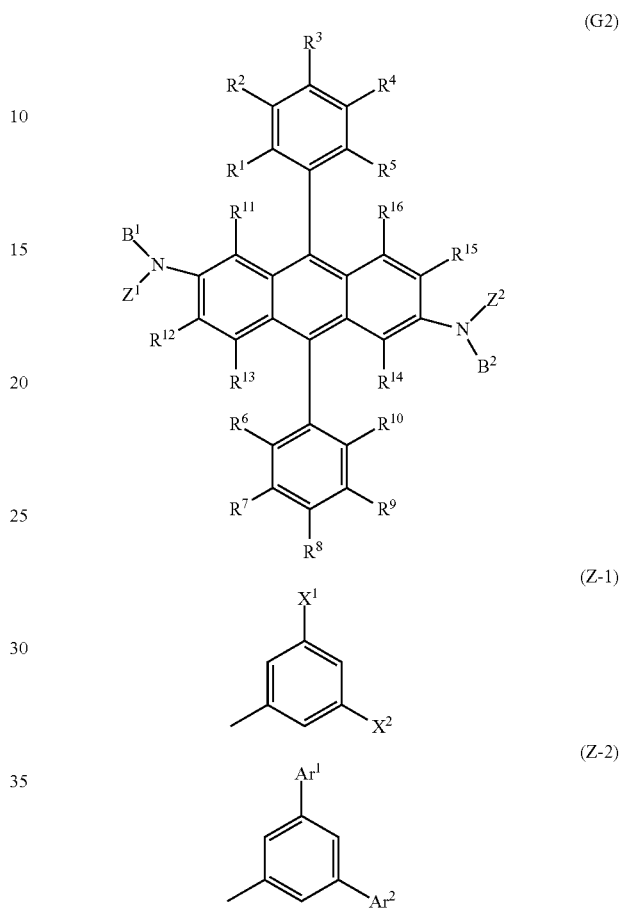

(G2)

(Z-1)

(Z-2)

In General Formula (G2), each of $B^1$ and $B^2$ independently represents a substituted or unsubstituted condensed heteroaromatic ring having 3 to 30 carbon atoms; and each of $Z^1$ and $Z^2$ independently has a structure represented by General Formula (Z-1) or General Formula (Z-2). In General Formula (Z-1), each of $X^1$ and $X^2$ independently represents any one of an alkyl group having 3 to 10 carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms. Each of $Ar^1$ and $Ar^2$ independently represents a substituted or unsubstituted aromatic hydrocarbon group having 6 to 13 carbon atoms, and at least one of $Ar^1$ and $Ar^2$ includes the same substituent as $X^1$. Each of $R^1$ to $R^{16}$ independently represents any one of hydrogen, an alkyl group having 3 to 10 carbon atoms, a substituted or unsubstituted cycloalkyl group having 3 to 10 carbon atoms, a trialkylsilyl group having 3 to 12 carbon atoms, and a substituted or unsubstituted aryl group having 6 to 25 carbon atoms.

Note that the condensed heteroaromatic ring in General Formulae (G1) and (G2) includes a pyrrole ring. As the condensed heteroaromatic ring including a pyrrole ring, an indole ring, a carbazole ring, an indenocarbazole ring, an indolocarbazole ring, a dibenzocarbazole ring, or the like is preferred.

Another embodiment of the present invention is a compound represented by General Formula (G3) below.

[Chemical Formula 3]

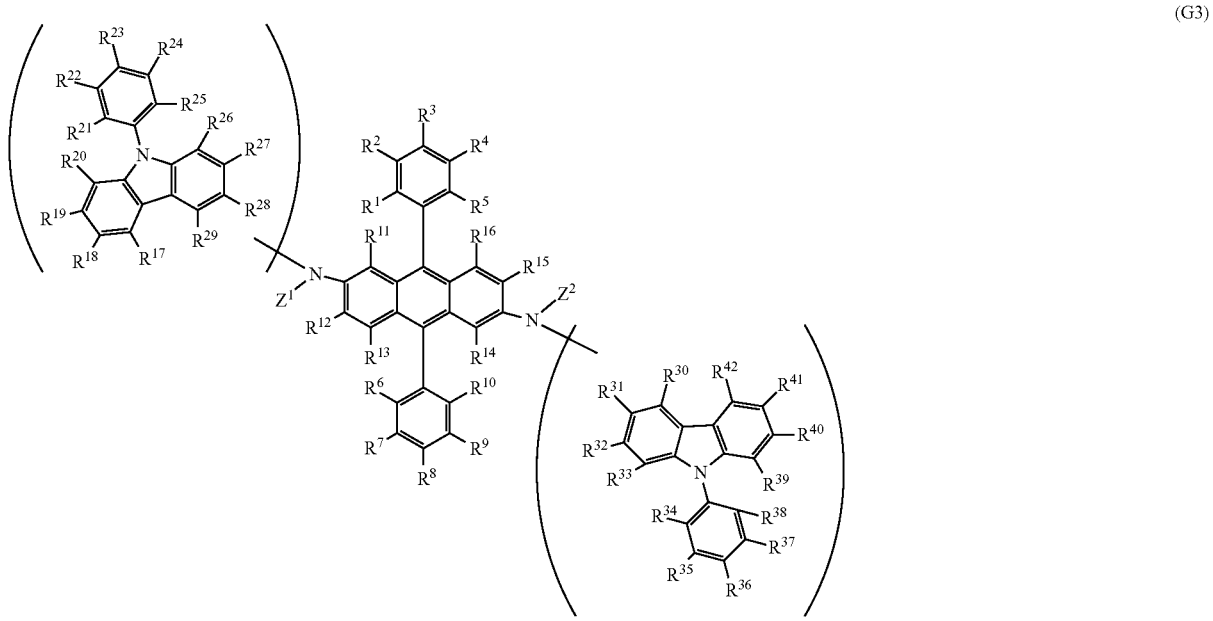

(G3)

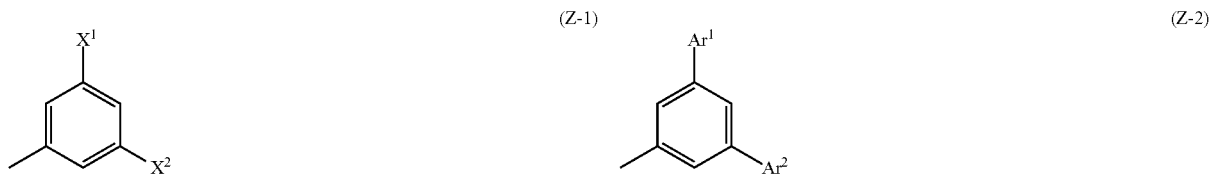

In General Formula (G3), each of $Z^1$ and $Z^2$ independently has a structure represented by General Formula (Z-1) or General Formula (Z-2). In General Formula (Z-1), each of $X^1$ and $X^2$ independently represents any one of an alkyl group having 3 to carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms. Each of $Ar^1$ and $Ar^2$ independently represents a substituted or unsubstituted aromatic hydrocarbon group having 6 to 13 carbon atoms, and at least one of $Ar^1$ and $Ar^2$ includes the same substituent as Each of $R^1$ to $R^{42}$ independently represents any one of hydrogen, an alkyl group having 3 to 10 carbon atoms, a substituted or unsubstituted cycloalkyl group having 3 to 10 carbon atoms, a trialkylsilyl having 3 to 12 carbon atoms, and a substituted or unsubstituted aryl group having 6 to 25 carbon atoms; any one of $R^{17}$ to $R^{29}$ is bonded to a nitrogen atom that is bonded to $Z^1$; and any one of $R^{30}$ to $R^{42}$ is bonded to a nitrogen atom that is bonded to $Z^2$.

Another embodiment of the present invention is a compound represented by General Formula (G4).

[Chemical Formula 4]

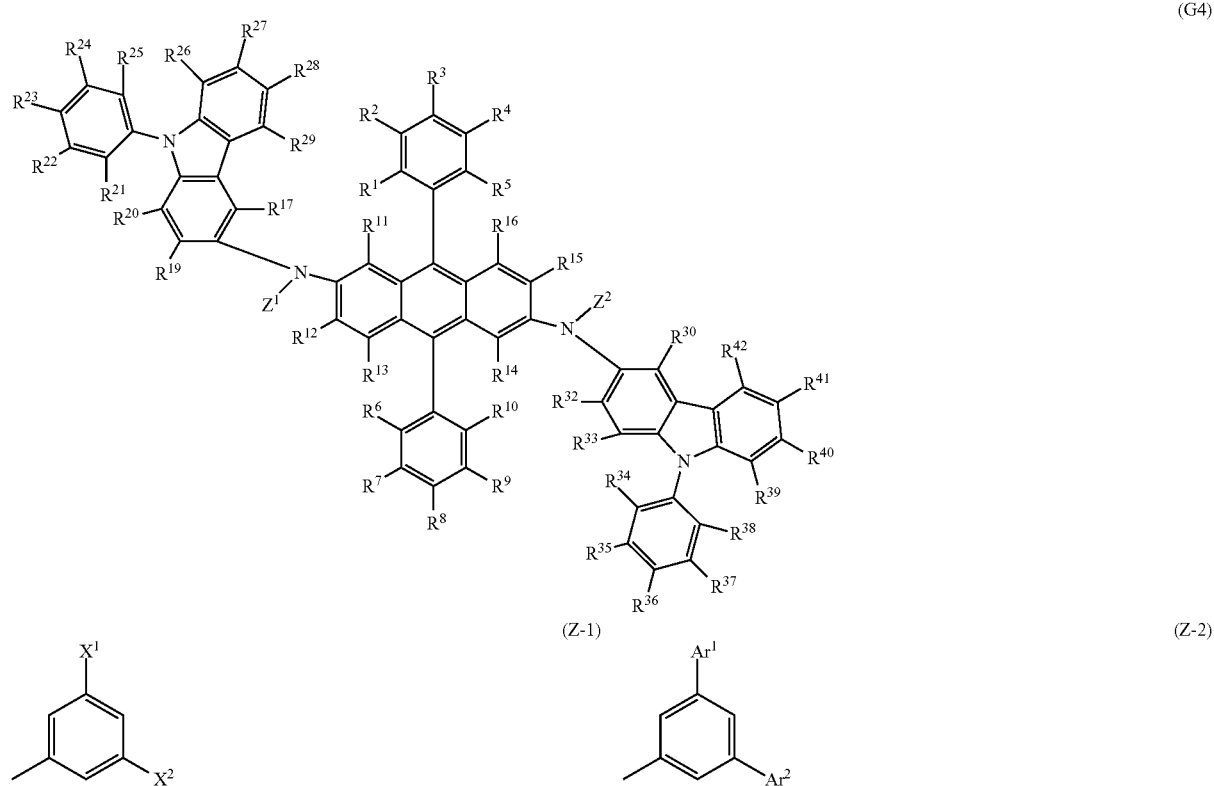

(G4)

(Z-1)

(Z-2)

In General Formula (G4), each of $Z^1$ and $Z^2$ independently has a structure represented by General Formula (Z-1) or General Formula (Z-2). In General Formula (Z-1), each of $X^1$ and $X^2$ independently represents any one of an alkyl group having 3 to carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms. Each of $Ar^1$ and $Ar^2$ independently represents a substituted or unsubstituted aromatic hydrocarbon group having 6 to 13 carbon atoms, and at least one of $Ar^1$ and $Ar^2$ includes the same substituent as $X^1$. Each of $R^1$ to $R^{17}$, $R^{19}$ to $R^{30}$, and $R^{32}$ to $R^{42}$ independently represents any one of hydrogen, an alkyl group having 3 to 10 carbon atoms, a substituted or unsubstituted cycloalkyl group having 3 to 10 carbon atoms, a trialkylsilyl group having 3 to 12 carbon atoms, and a substituted or unsubstituted aryl group having 6 to 25 carbon atoms.

Another embodiment of the present invention is a compound represented by Structural Formula (100).

[Chemical Formula 5]

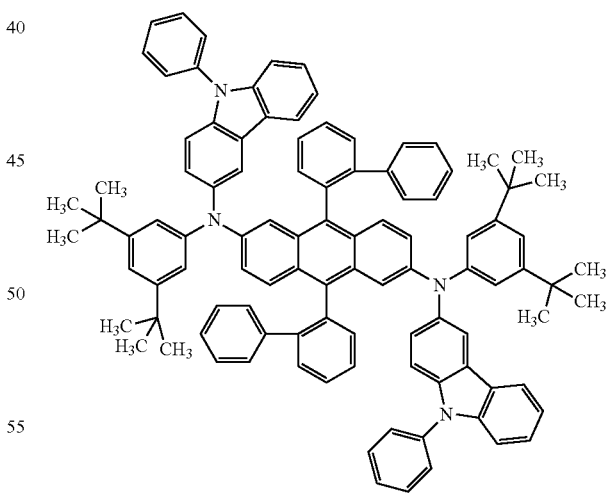

(100)

Another embodiment of the present invention is a light-emitting device using the above-described compound of one embodiment of the present invention. Note that the present invention also includes a light-emitting device in which an EL layer provided between a pair of electrodes or a light-emitting layer included in the EL layer contains the compound of one embodiment of the present invention. In addition to the aforementioned light-emitting device, the present invention includes a light-emitting device including a layer (e.g., a cap layer) that is in contact with an electrode and contains an organic compound. In addition to the light-emitting devices, a light-emitting apparatus including a transistor, a substrate, and the like is also included in the scope of the invention. Furthermore, in addition to the light-emitting apparatus, an electronic device and a lighting device that include a microphone, a camera, an operation button, an external connection portion, a housing, a cover, a support, a speaker, or the like are also included in the scope of the invention.

In addition, the scope of one embodiment of the present invention includes a light-emitting apparatus including a light-emitting device, and a lighting device including the light-emitting apparatus. Accordingly, the light-emitting apparatus in this specification refers to an image display device and a light source (including a lighting device). In addition, the light-emitting apparatus includes the following in its category: a module in which a connector such as a flexible printed circuit (FPC) or a tape carrier package (TCP) is attached to a light-emitting apparatus; a module in which a printed wiring board is provided at the end of a TCP; and a module in which an integrated circuit (IC) is directly mounted on a light-emitting device by a chip on glass (COG) method.

One embodiment of the present invention can provide a novel compound. Another embodiment of the present invention can provide a novel compound that can be used in a light-emitting device. Another embodiment of the present invention can provide a novel compound that can be used in an EL layer of a light-emitting device. Another embodiment of the present invention can provide a light-emitting device with high emission efficiency. Another embodiment of the present invention can provide a highly reliable light-emitting device. Another embodiment of the present invention can provide a novel light-emitting device. Another embodiment of the present invention can provide a novel light-emitting apparatus, a novel electronic device, or a novel lighting device.

Note that the description of these effects does not preclude the existence of other effects. One embodiment of the present invention does not necessarily achieve all the effects listed above. Other effects will be apparent from and can be derived from the descriptions of the specification, the drawings, the claims, and the like.

DETAILED DESCRIPTION OF THE INVENTION

Figure 1A:
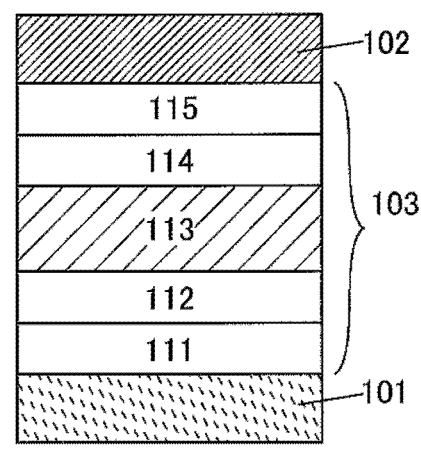
FIG. 1A illustrates a structure of a light-emitting device.

Embodiments and examples of the present invention will be described in detail below with reference to the drawings. Note that the present invention is not limited to the following description, and the modes and details of the present invention can be modified in various ways without departing from the spirit and scope of the present invention. Therefore, the present invention should not be construed as being limited to the description in the following embodiments and examples.

Note that the position, size, range, or the like of each component illustrated in drawings and the like is not accurately represented in some cases for easy understanding. Therefore, the disclosed invention is not necessarily limited to the position, size, range, or the like disclosed in the drawings and the like.

In describing structures of the invention with reference to the drawings in this specification and the like, the same components in different drawings are commonly denoted by the same reference numeral.

In this specification and the like, a singlet excited state (S*) refers to a singlet state having excitation energy. An S1 level refers to the lowest level of the singlet excitation energy level, that is, the excitation energy level of the lowest singlet excited state (S1 state). A triplet excited state (T*) refers to a triplet state having excitation energy. A T1 level refers to the lowest level of the triplet excitation energy level, that is, the excitation energy level of the lowest triplet excited state (T1 state). Note that in this specification and the like, simple expressions "singlet excited state" and "singlet excitation energy level" sometimes mean the S1 state and the S1 level, respectively. In addition, expressions "triplet excited state" and "triplet excitation energy level" sometimes mean the T1 state and the T1 level, respectively.

In this specification and the like, a fluorescent substance refers to a compound that emits light in a visible light region or a near-infrared region when the relaxation from a singlet excited state to a ground state occurs. A phosphorescent substance refers to a compound that emits light in a visible light region or a near-infrared region at room temperature when the relaxation from a triplet excited state to a ground state occurs. That is, a phosphorescent substance refers to a compound that can convert triplet excitation energy into light emission.

Embodiment 1

In this embodiment, compounds that are embodiments of the present invention will be described. A compound of one embodiment of the present invention is represented by General Formula (G1) below.

[Chemical Formula 6]

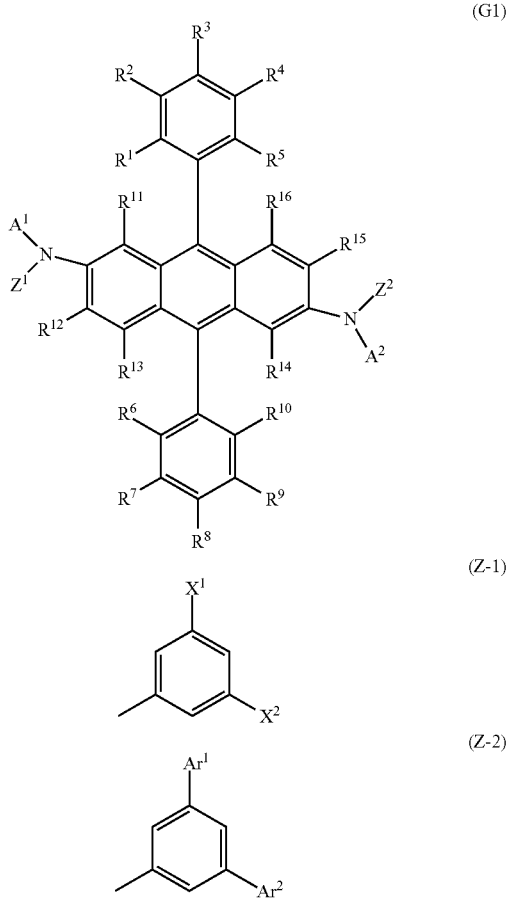

In General Formula (G1), each of $A^1$ and $A^2$ independently represents a substituted or unsubstituted condensed aromatic ring having 10 to 30 carbon atoms, a substituted or unsubstituted condensed heteroaromatic ring having 3 to 30 carbon atoms, or a structure represented by General Formula (Z-1) or General Formula (Z-2); and each of $Z^1$ and $Z^2$ independently has a structure represented by General Formula (Z-1) or (Z-2). In General Formula (Z-1), each of $X^1$ and $X^2$ independently represents any one of an alkyl group having 3 to 10 carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms. Each of $Ar^1$ and $Ar^2$ independently represents a substituted or unsubstituted aromatic hydrocarbon group having 6 to 13 carbon atoms, and at least one of $Ar^1$ and $Ar^2$ includes the same substituent as $X^1$. Each of $R^1$ to $R^{16}$ independently represents any one of hydrogen, an alkyl group having 3 to 10 carbon atoms, a substituted or unsubstituted cycloalkyl group having 3 to 10 carbon atoms, a trialkylsilyl group having 3 to 12 carbon atoms, and a substituted or unsubstituted aryl group having 6 to 25 carbon atoms.

Another embodiment of the present invention is a compound represented by General Formula (G2) below.

[Chemical Formula 7]

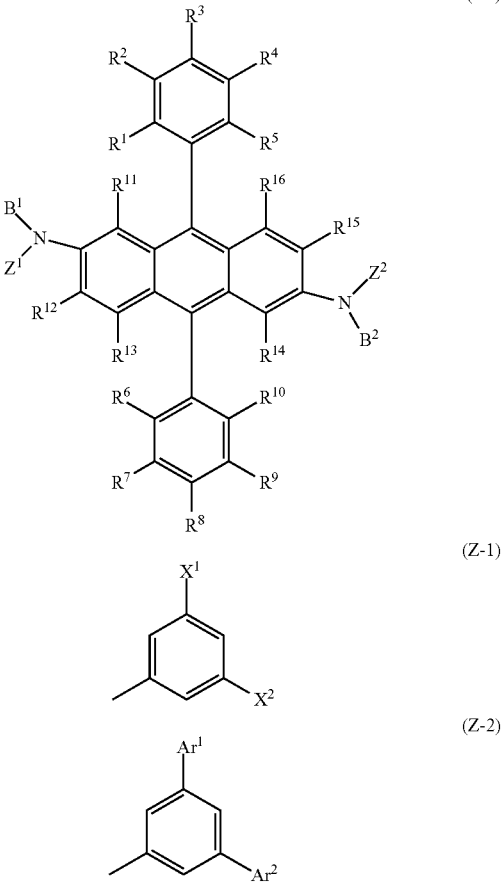

In General Formula (G2), each of $B^1$ and $B^2$ independently represents a substituted or unsubstituted condensed heteroaromatic ring having 3 to 30 carbon atoms; and each of $Z^1$ and $Z^2$ independently has a structure represented by General Formula (Z-1) or General Formula (Z-2). In General Formula (Z-1), each of $X^1$ and $X^2$ independently represents any one of an alkyl group having 3 to 10 carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms, Each of $Ar^1$ and $Ar^2$ independently represents a substituted or unsubstituted aromatic hydrocarbon group having 6 to 13 carbon atoms, and at least one of $Ar^1$ and $Ar^2$ includes the same substituent as $X^1$. Each of $R^1$ to $R^{16}$ independently represents any one of hydrogen, an alkyl group having 3 to 10 carbon atoms, a substituted or unsubstituted cycloalkyl group having 3 to 10 carbon atoms, a trialkylsilyl group having 3 to 12 carbon atoms, and a substituted or unsubstituted aryl group having 6 to 25 carbon atoms.

Each of the condensed heteroaromatic ring represented by $A^1$ and $A^2$ in General Formula (G1) and $B^1$ and $B^2$ in General Formula (G2) is preferably a condensed heteroaromatic ring including a pyrrole ring.

Each of the condensed heteroaromatic ring represented by $A^1$ and $A^2$ in General Formula (G1) and $B^1$ and $B^2$ in General Formula (G2) is preferably an indole ring, a carbazole ring, an indenocarbazole ring, an indolocarbazole ring, or a dibenzocarbazole ring.

Another embodiment of the present invention is a compound represented by General Formula (G3) below.

[Chemical Formula 8]

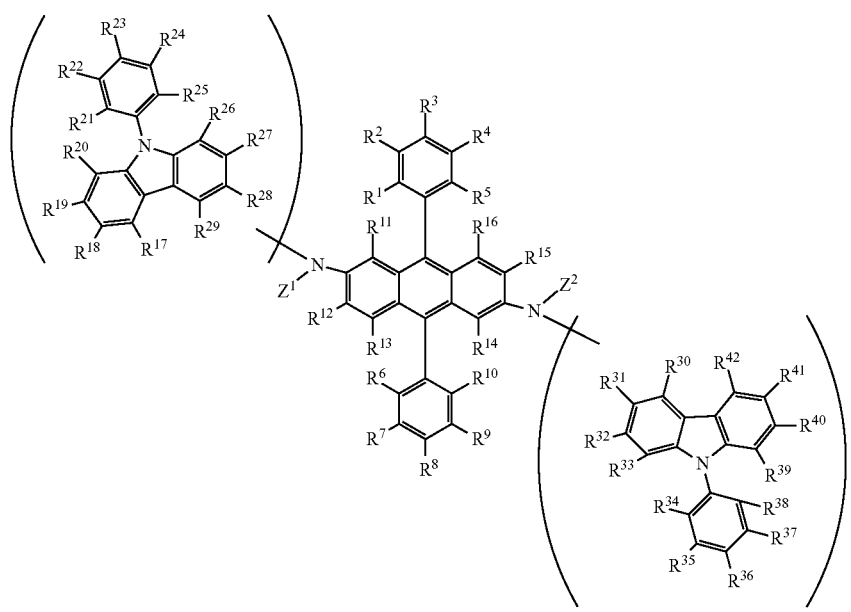

(G3)

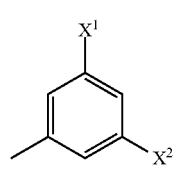

(Z-1)

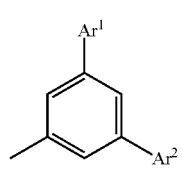

(Z-2)

In General Formula (G3), each of $Z^1$ and $Z^2$ independently has a structure represented by General Formula (Z-1) or General Formula (Z-2). In General Formula (Z-1), each of $X^1$ and $X^2$ independently represents any one of an alkyl group having 3 to carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms. Each of $Ar^1$ and $Ar^2$ independently represents a substituted or unsubstituted aromatic hydrocarbon group having 6 to 13 carbon atoms, and at least one of $Ar^1$ and $Ar^2$ includes the same substituent as $X^1$. Each of $R^1$ to $R^{42}$ independently represents any one of hydrogen, an alkyl group having 3 to 10 carbon atoms, a substituted or unsubstituted cycloalkyl group having 3 to 10 carbon atoms, a trialkylsilyl having 3 to 12 carbon atoms, and a substituted or unsubstituted aryl group having 6 to 25 carbon atoms; any one of $R^{17}$ to $R^{29}$ is bonded to a nitrogen atom that is bonded to $Z^1$; and any one of $R^{30}$ to $R^{42}$ is bonded to a nitrogen atom that is bonded to $Z^2$.

Another embodiment of the present invention is a compound represented by General Formula (G4).

having 6 to 13 carbon atoms, and at least one of $Ar^1$ and $Ar^2$ includes the same substituent as $X^1$. Each of $R^1$ to $R^{17}$, $R^{19}$ to $R^{30}$, and $R^{32}$ to $R^{42}$ independently represents any one of hydrogen, an alkyl group having 3 to 10 carbon atoms, a substituted or unsubstituted cycloalkyl group having 3 to 10 carbon atoms, a trialkylsilyl group having 3 to 12 carbon atoms, and a substituted or unsubstituted aryl group having 6 to 25 carbon atoms.

The compound of one embodiment of the present invention is a material having a function of converting singlet excitation energy into light emission (a fluorescent substance), and thus can be used as a guest material in combination with a host material in a light-emitting layer of a light-emitting device. The compound of one embodiment of the present invention has a luminophore that contributes to light emission and a protecting group that prevents the transfer of triplet excitation energy from the host material to the compound due to the Dexter mechanism. The luminophore of the compound of one embodiment of the present invention is a condensed aromatic ring or a condensed heteroaromatic ring. Each of the aryl groups in two or more diarylamino groups included in the compound of one

[Chemical Formula 9]

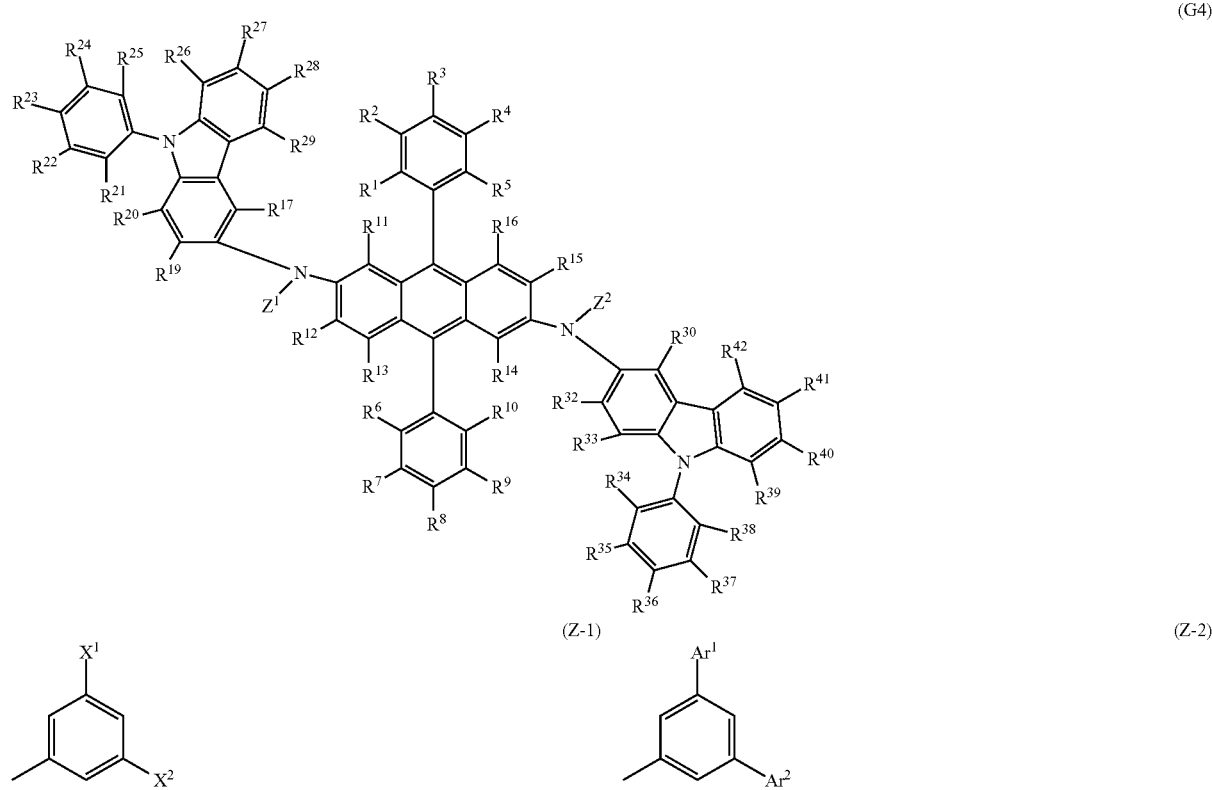

In General Formula (G4), each of $Z^1$ and $Z^2$ independently has a structure represented by General Formula (Z-1) or General Formula (Z-2). In General Formula (Z-1), each of $X^1$ and $X^2$ independently represents any one of an alkyl group having 3 to carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms. Each of $Ar^1$ and $Ar^2$ independently represents a substituted or unsubstituted aromatic hydrocarbon group embodiment of the present invention has at least two protecting groups; specifically, the protecting group is any of a cycloalkyl group having a bridge structure and having 7 to 10 carbon atoms, an alkyl group having 3 to 10 carbon atoms, a substituted or unsubstituted cycloalkyl group having 3 to 10 carbon atoms, and a trialkylsilyl group having 3 to 12 carbon atoms.

Note that the compound of one embodiment of the present invention has a structure in which the two or more diarylamino groups including the protecting groups are bonded to the luminophore at symmetric positions, whereby the quantum yield can be increased. When the diarylamino groups are included in the compound of one embodiment of the present invention, an increase in molecular weight can be prevented and a sublimation property can be maintained.

In the compound of one embodiment of the present invention, since the protecting group is bonded to the aryl group of the diarylamino bonded to the luminophore, the protecting group can be positioned to cover the luminophore, and the host material and the luminophore can be made away from each other at such a distance that energy transfer from the host material to the luminophore due to the Dexter mechanism is unlikely to occur.

Note that in General Formulae (G1) to (G4), examples of the condensed aromatic ring having 10 to 30 carbon atoms or the condensed heteroaromatic ring having 3 to 30 carbon atoms include a phenanthrene ring, a stilbene ring, an acridone ring, a phenoxazine ring, and a phenothiazine ring. Furthermore, other examples are a naphthalene ring, an anthracene ring, a fluorene ring, a chrysene ring, a triphenylene ring, tetracene ring, a pyrene ring, a perylene ring, a quinoline ring, a benzimidazole ring, a quinazoline ring, a carbazole ring, an acridine ring, a coumalin ring, a quinacridone ring, a naphthobisbenzofuran ring, a dibenzofuran ring, a dibenzothiophene ring, an indenocarbazole ring, an indolocarbazole ring, and a dibenzo carbazole ring, which can increase the fluorescence quantum yield.

Note that in General Formulae (G1) to (G4), examples of the aromatic hydrocarbon group having 6 to 13 carbon atoms include a phenyl group, a biphenyl group, a naphthyl group, and a fluorenyl group.

In General Formulae (G1) to (G4), specific examples of the alkyl group having 3 to 10 carbon atoms include a propyl group, an isopropyl group, a butyl group, an isobutyl group, a sec-butyl group, a tert-butyl group, a pentyl group, a hexyl group, a heptyl group, and an octyl group.

In General Formulae (G1) to (G4), specific examples of the cycloalkyl group having 3 to 10 carbon atoms include a cyclopropyl group, a cyclobutyl group, and a cyclohexyl group. In the case where the cycloalkyl group has a substituent, specific examples of the substituent include an alkyl group having 1 to 7 carbon atoms, such as a methyl group, an ethyl group, a propyl group, an isopropyl group, a butyl group, an isobutyl group, a sec-butyl group, a left-butyl group, a pentyl group, or a hexyl group, a cycloalkyl group having 5 to 7 carbon atoms, such as a cyclopentyl group, a cyclohexyl group, a cycloheptyl group, or a 8,9,10-trinorbornanyl group, and an aryl group having 6 to 12 carbon atoms, such as a phenyl group, a naphthyl group, or a biphenyl group.

In General Formulae (G1) to (G4), specific examples of the cycloalkyl group having a bridge structure and having 7 to 10 carbon atoms include an adamantyl group, a bicyclo[2.2.1]heptyl group, a tricyclo[5.2.1.0$^{2,6}$]decanyl group, and a noradamantyl group. In General Formulae (G1) to (G4), specific examples of a trialkylsilyl group having 3 to 12 carbon atoms include a trimethylsilyl group, a triethylsilyl group, and a tert-butyl dimethylsilyl group.

In the case where any one of the condensed aromatic ring, the condensed heteroaromatic ring, the aromatic hydrocarbon group having 6 to 13 carbon atoms, the cycloalkyl group having 3 to 10 carbon atoms, and the aryl group having 6 to 25 carbon atoms has a substituent in General Formulae (G1) to (G4), examples of the substituent include an alkyl group having 1 to 7 carbon atoms, such as a methyl group, an ethyl group, a propyl group, an isopropyl group, a butyl group, an isobutyl group, a sec-butyl group, a tert-butyl group, a pentyl group, or a hexyl group, a cycloalkyl group having 5 to 7 carbon atoms, such as a cyclopentyl group, a cyclohexyl group, a cycloheptyl group, or an 8,9,10-trinorbornanyl group, and an aryl group having 6 to 12 carbon atoms, such as a phenyl group, a naphthyl group, or a biphenyl group.

In General Formulae (G1) to (G4), specific examples of the aryl group having 6 to 25 carbon atoms include a phenyl group, a naphthyl group, a biphenyl group, a fluorenyl group, and a spirofluorenyl group. Note that in the case where the aryl group has a substituent, examples of the substituent include an alkyl group having 3 to 10 carbon atoms, a substituted or unsubstituted cycloalkyl group having 3 to 10 carbon atoms, and a trialkylsilyl group having 3 to 12 carbon atoms.

Specific examples of the compounds represented by General Formulae (G1) to (G4) are shown in Structure Formulae (100) to (139) below. Note that specific examples of the compounds represented by General Formulae (G1) to (G4) are not limited to those shown below.

[Chemical Formula 10]

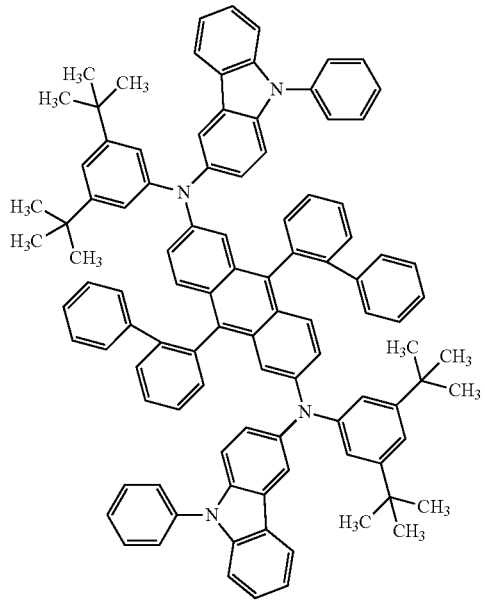

(100)

(101)
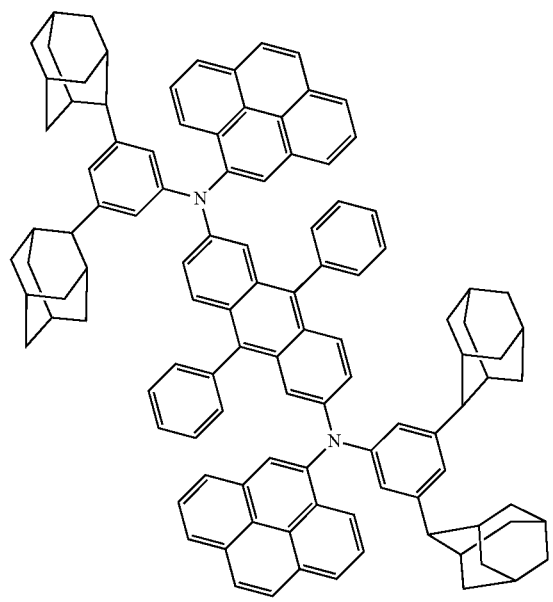
(103)
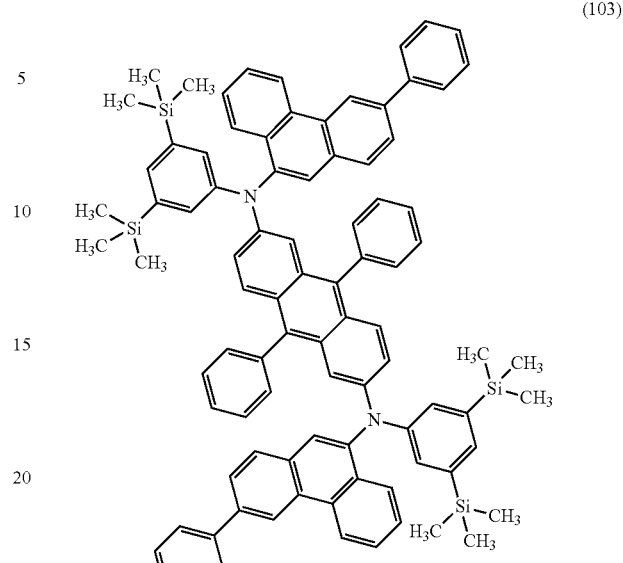
[Chemical Formula 11]
(102)
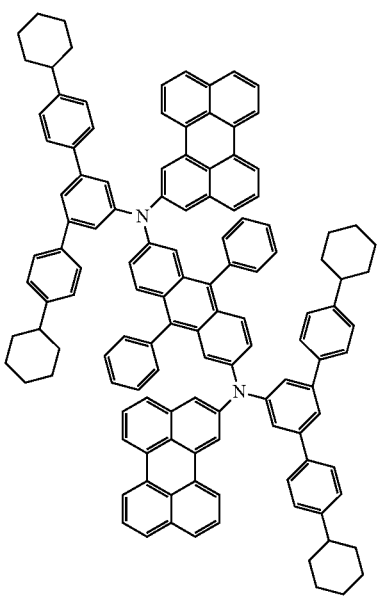
(104)
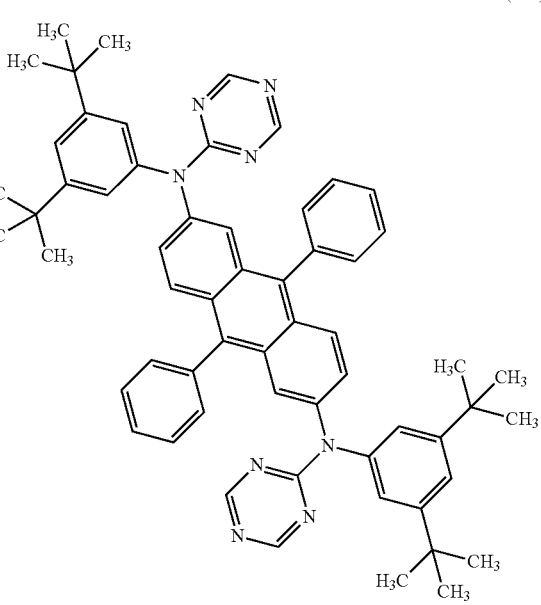

[Chemical Formula 12]
(105)
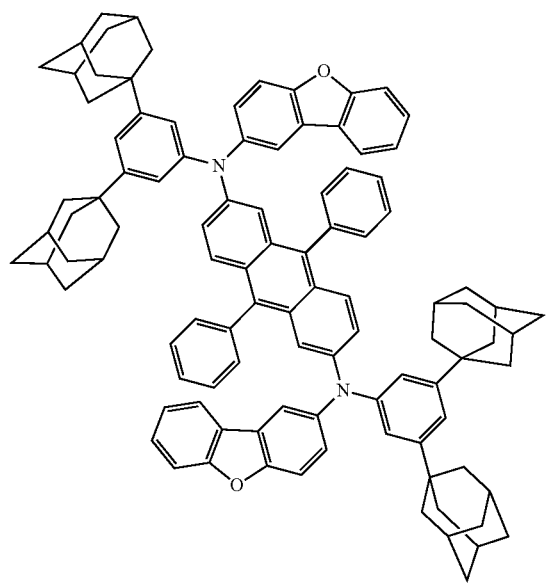
(106)
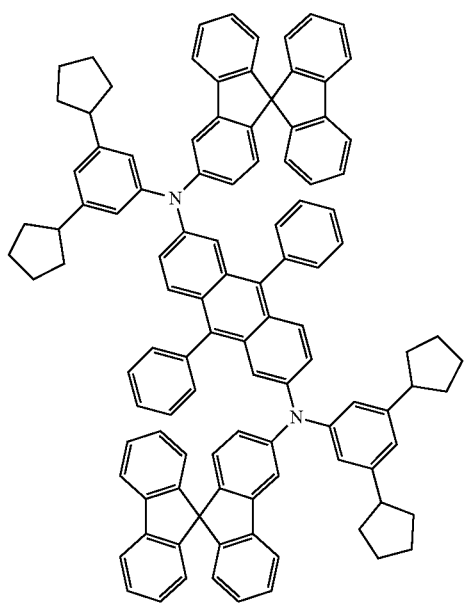
(108)
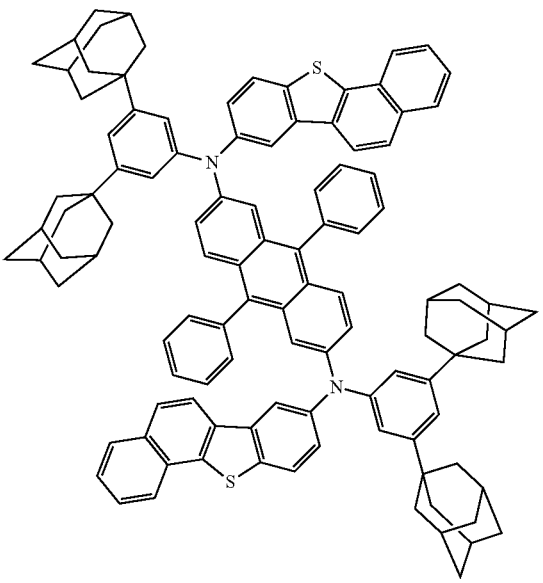

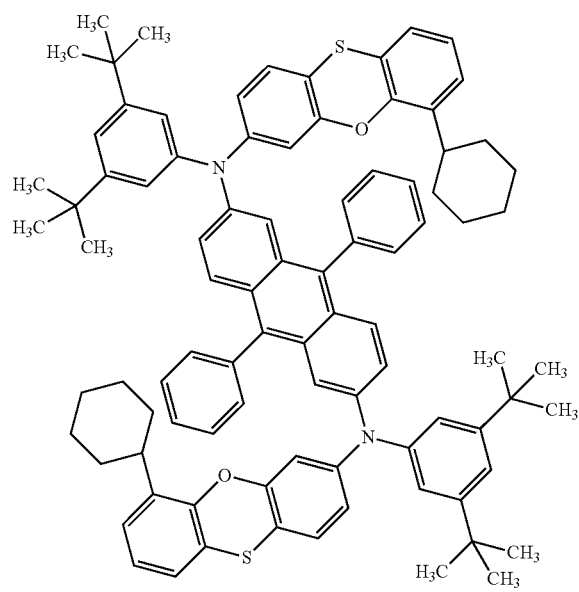
(109)
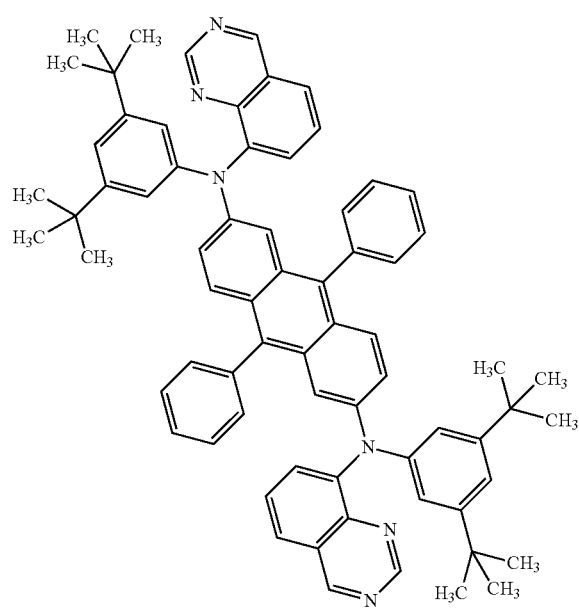
(110)
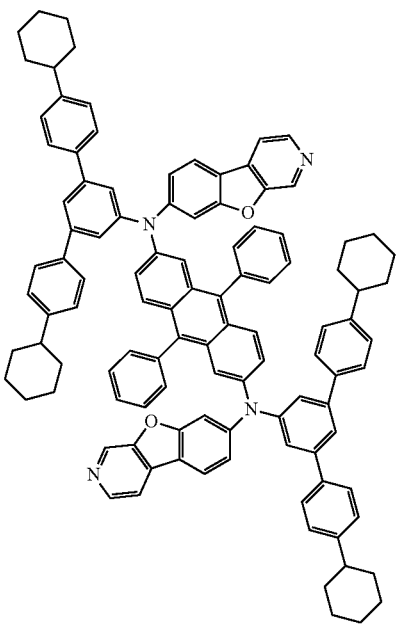
(111)
[Chemical Formula 13]
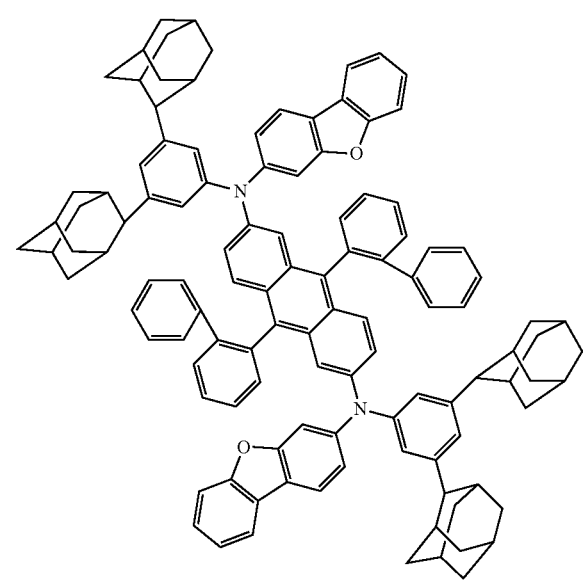
(112)

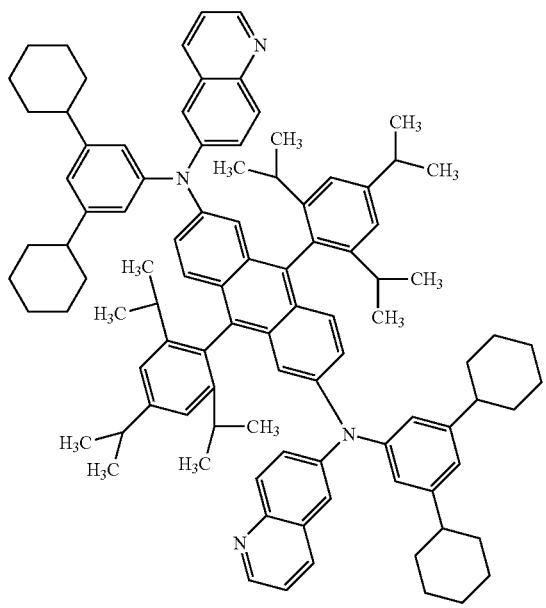 (113)
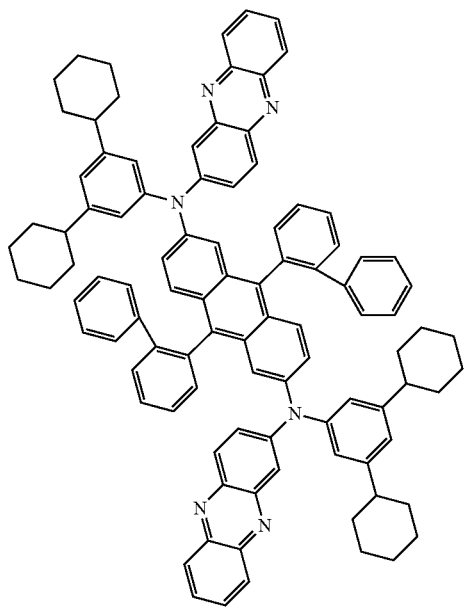 (115)
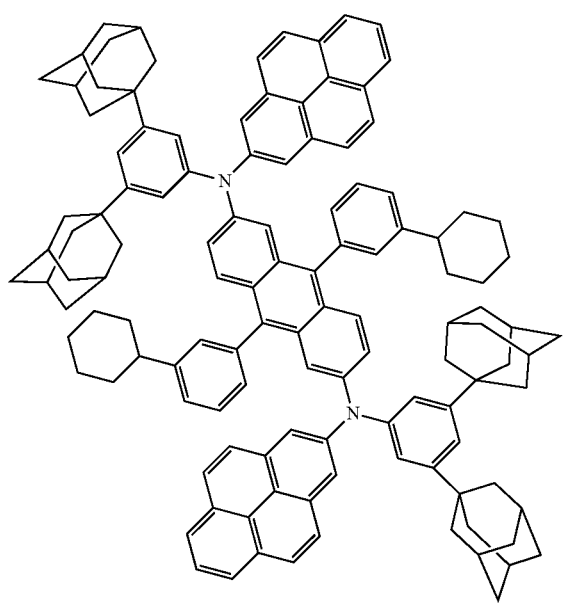 (114)
[Chemical Formula 14]
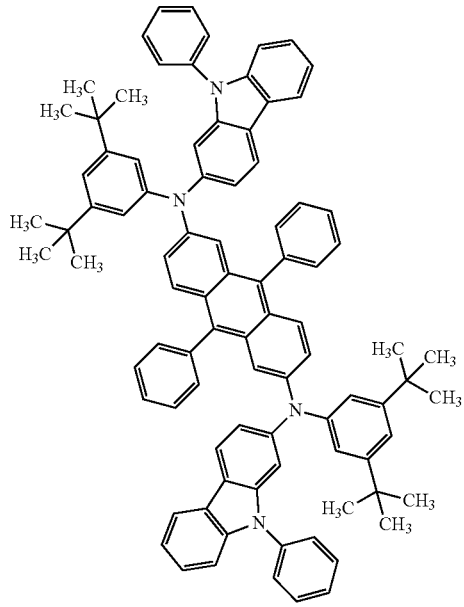 (116)

(117)
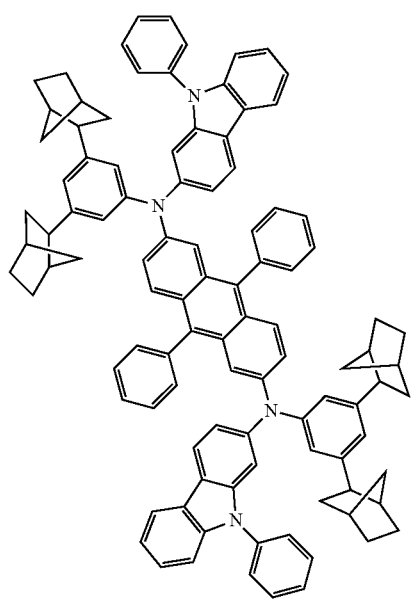
(118)
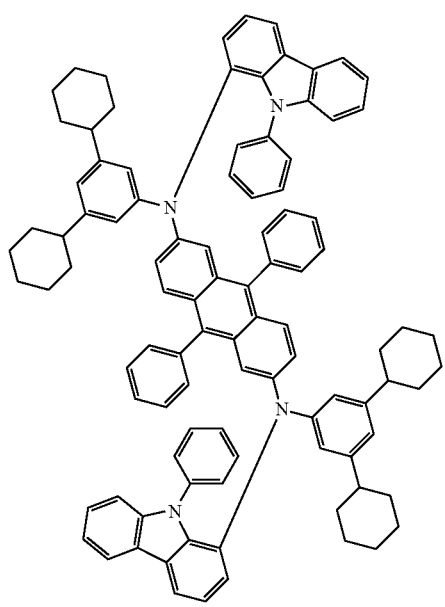
[Chemical Formula 15]
(119)
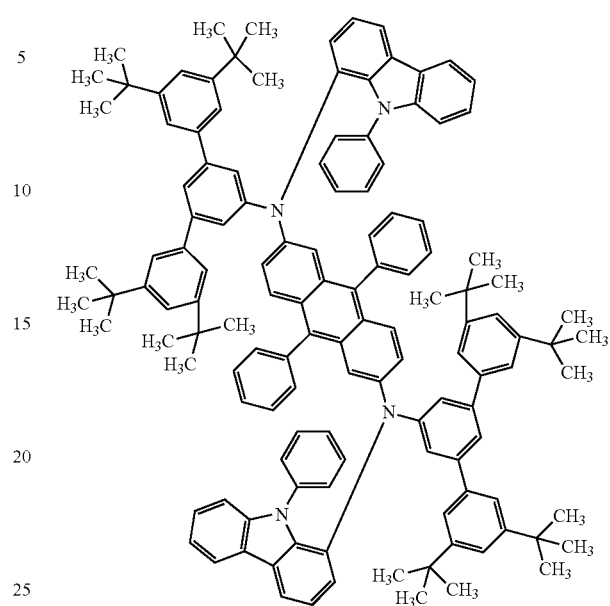
(120)
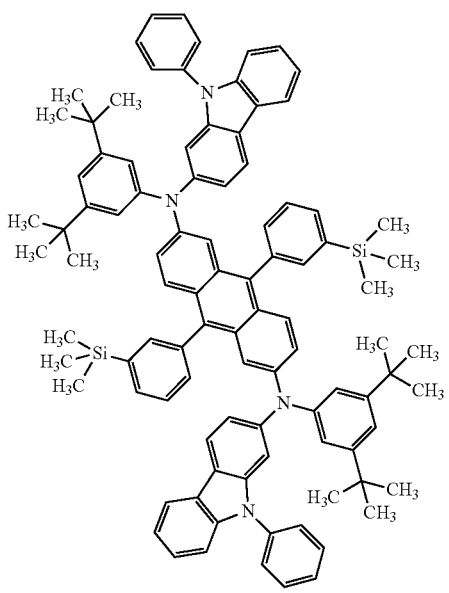

-continued
(121)
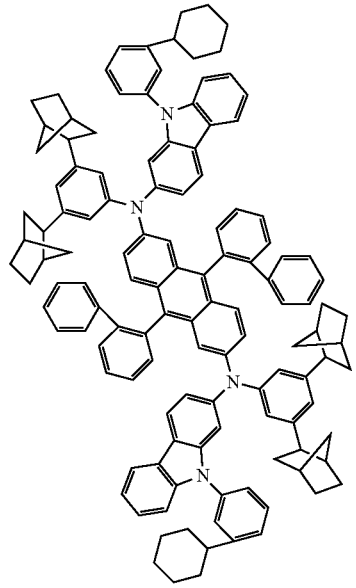
(122)
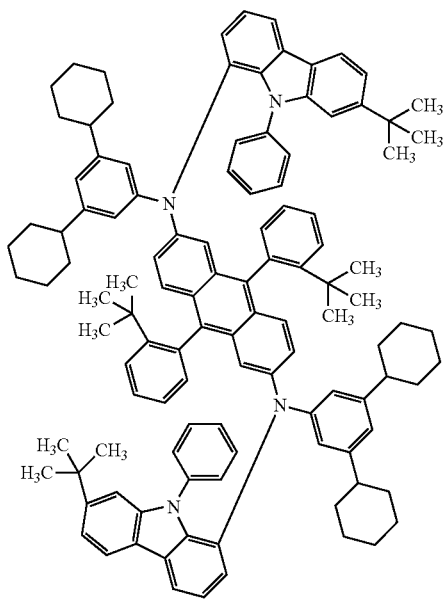
-continued
(123)
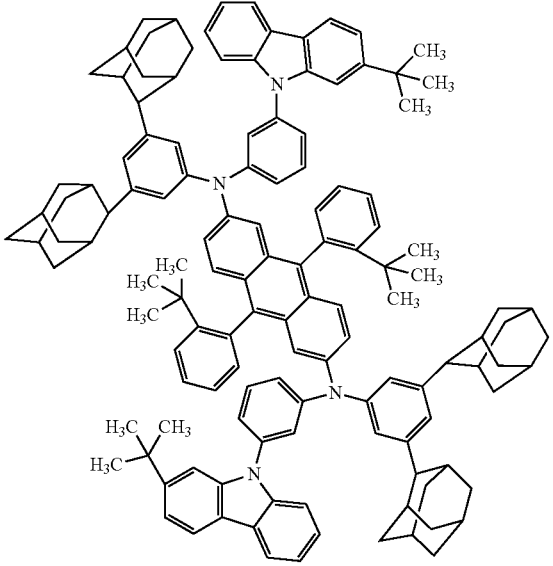
[Chemical Formula 16]
(124)
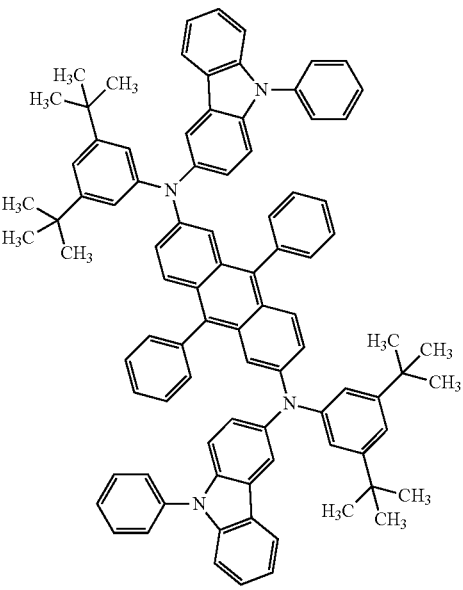

(125)
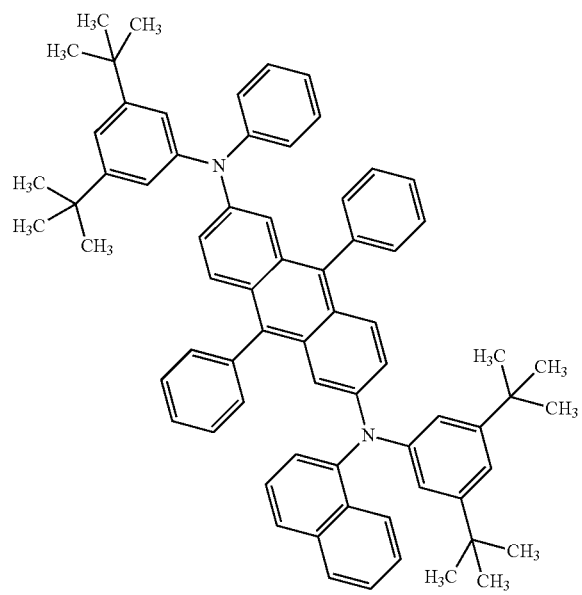
(126)
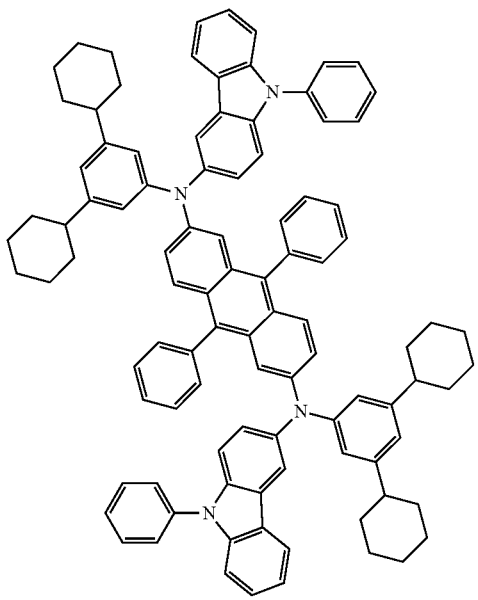
(127)
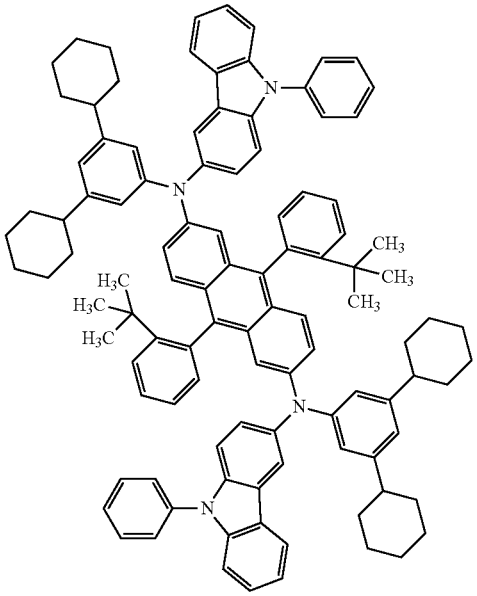
[Chemical Formula 17]
(128)
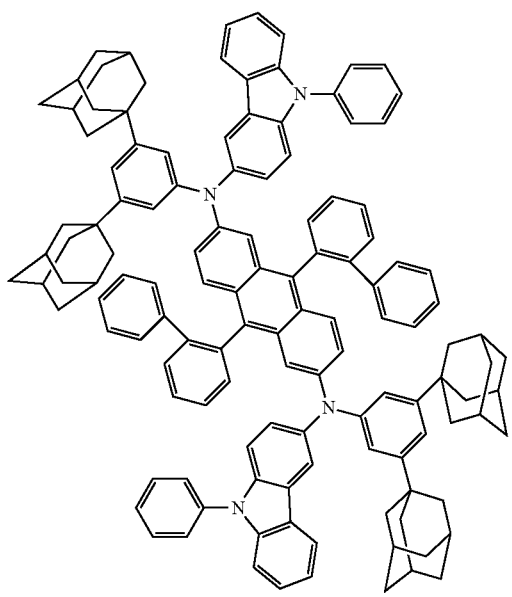

-continued
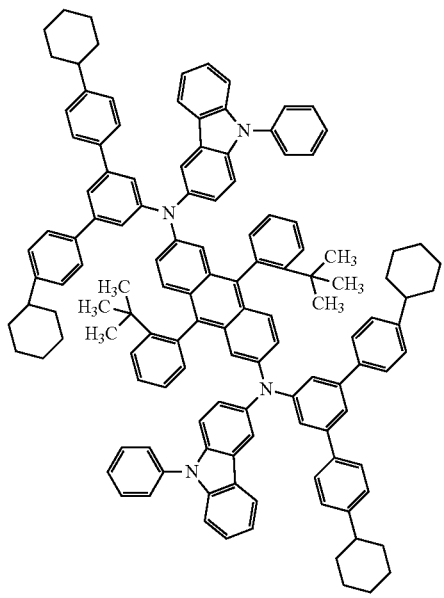
(129)
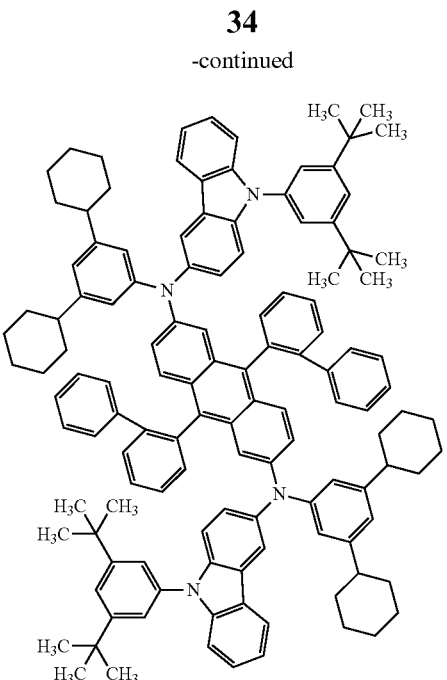
(131)
[Chemical Formula 18]
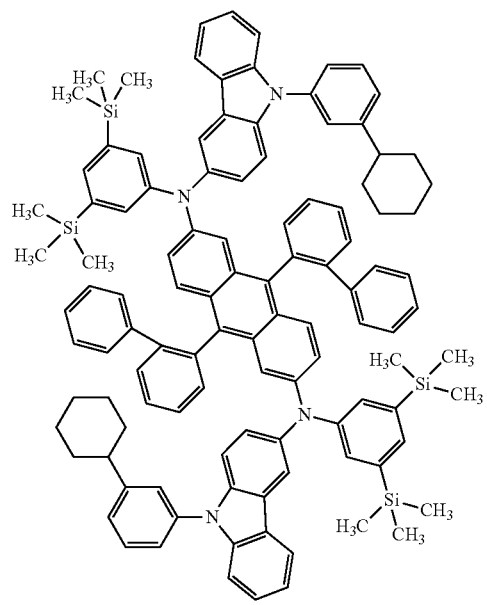
(130)
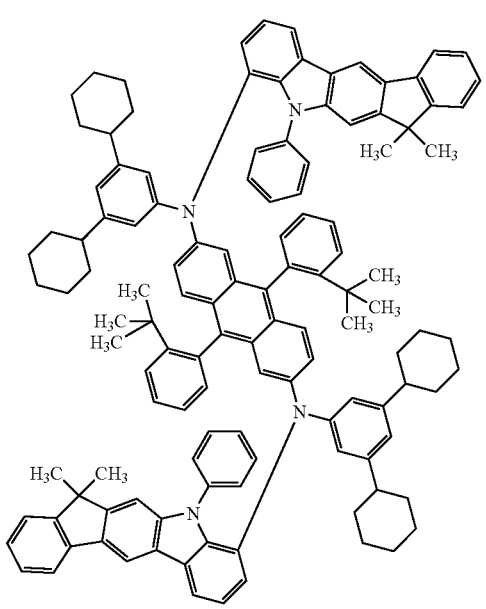
(132)

(133)
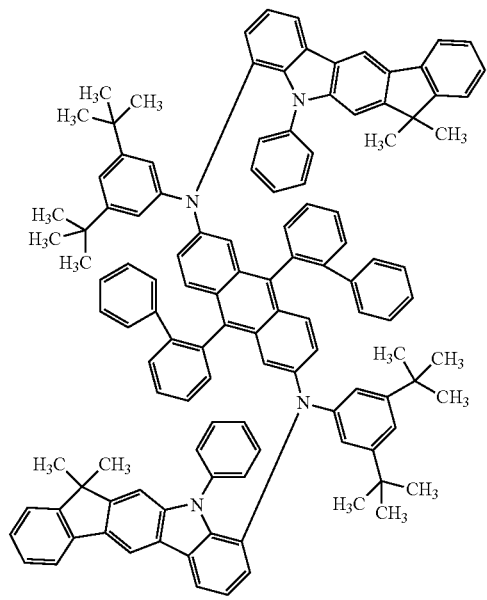
(134)
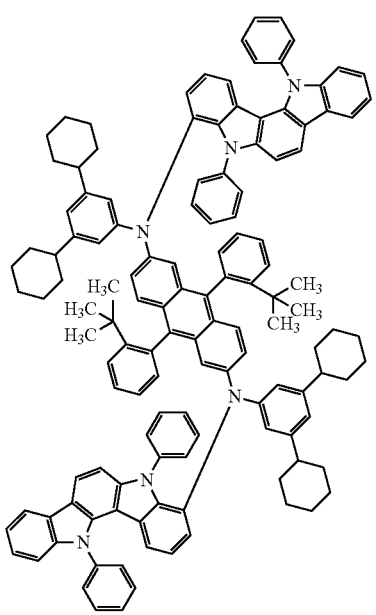
(135)
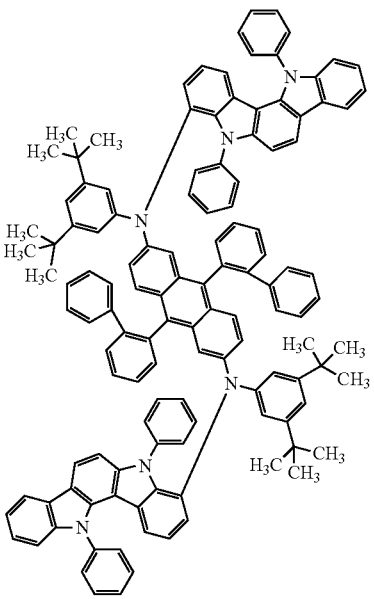
[Chemical Formula 19]
(136)
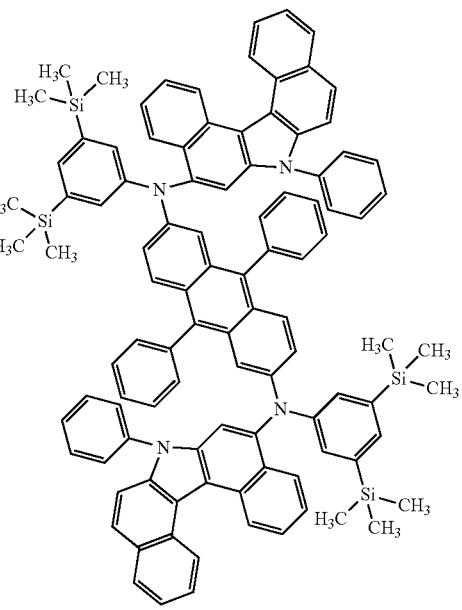

(137)
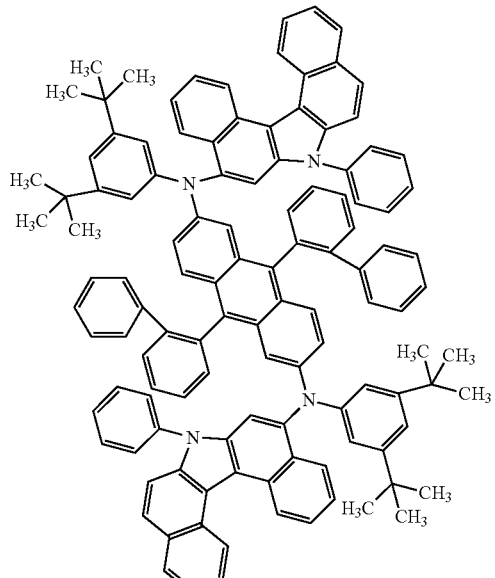
(139)
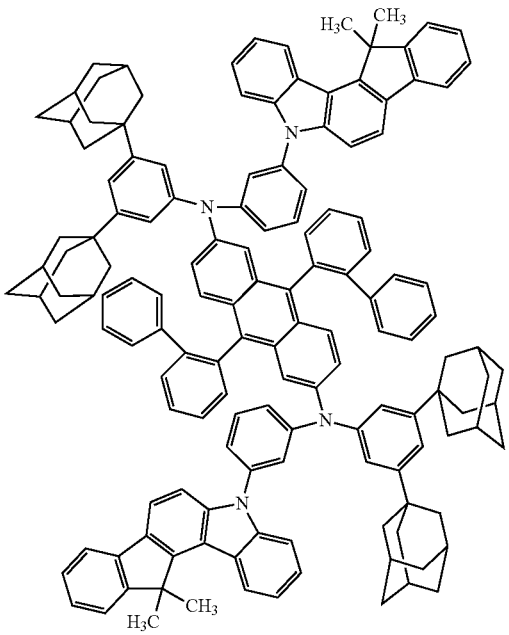
(138)
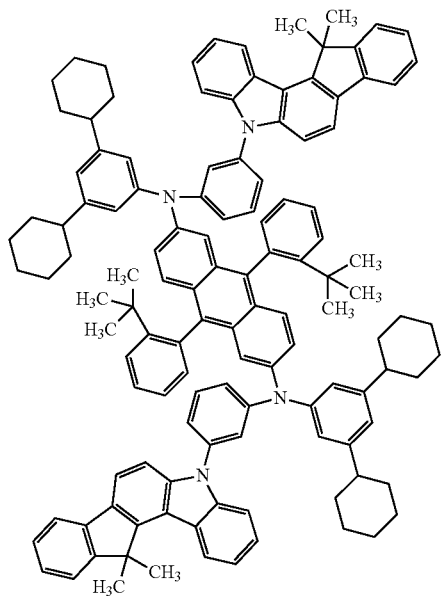
<Method of Synthesizing Organic Compound Represented by General Formula (G1)>
Next, described is a method of synthesizing the compound represented by General Formula (G1) below.
[Chemical Formula 20]
(G1)
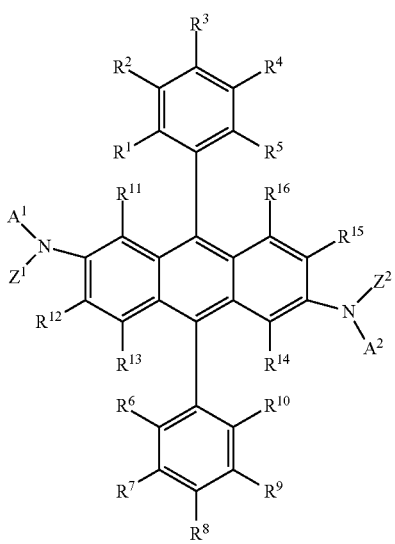
(Z-1)
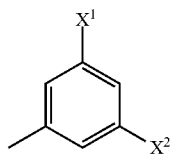

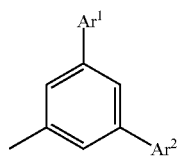

(Z-2)

In General Formula (G1), each of $A^1$ and $A^2$ independently represents a substituted or unsubstituted condensed aromatic ring having 10 to 30 carbon atoms, a substituted or unsubstituted condensed heteroaromatic ring having 3 to 30 carbon atoms, or a structure represented by General Formula (Z-1) or General Formula (Z-2); and each of $Z^1$ and $Z^2$ independently has a structure represented by General Formula (Z-1) or (Z-2). In General Formula (Z-1), each of $X^1$ and $X^2$ independently represents any one of an alkyl group having 3 to 10 carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms. Each of $Ar^1$ and $Ar^2$ independently represents a substituted or unsubstituted aromatic hydrocarbon group having 6 to 13 carbon atoms, and at least one of $Ar^1$ and $Ar^2$ includes the same substituent as $X^1$. Each of $R^1$ to $R^{16}$ independently represents any one of hydrogen, an alkyl group having 3 to 10 carbon atoms, a substituted or unsubstituted cycloalkyl group having 3 to 10 carbon atoms, a trialkylsilyl group having 3 to 12 carbon atoms, and a substituted or unsubstituted aryl group having 6 to 25 carbon atoms.

The compound represented by General Formula (G1) can be synthesized, for example, by a method shown in Synthesis Schemes (S-1) and (S-2) below.

First, a compound 1, a compound 2 (aniline compound), and a compound 3 (aniline compound) are coupled, whereby a compound 4 (diamine compound) is obtained (Synthesis Scheme (S-1)).

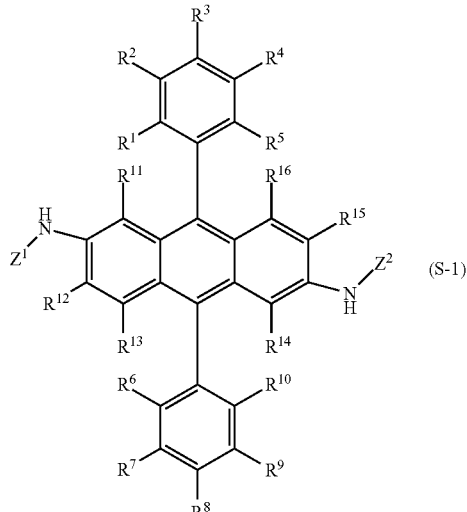

Compound 4

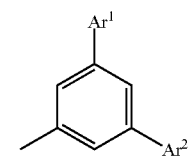

(Z-1)  (Z-2)

Next, the compound 4 (diamine compound), a compound 5 (halogenated aryl), and a compound 6 (halogenated aryl) are coupled, whereby the compound represented by General Formula (G1) is obtained (Synthesis Scheme (S-2)).

[Chemical Formula 21]

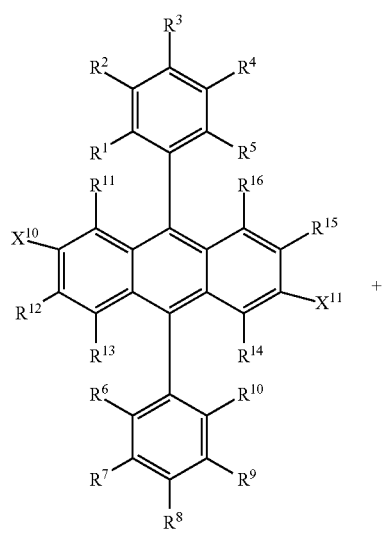

Compound 1

Z¹—NH₂ + Z²—NH₂  →(Coupling reaction)

Compound 2    Compound 3

[Chemical Formula 22]

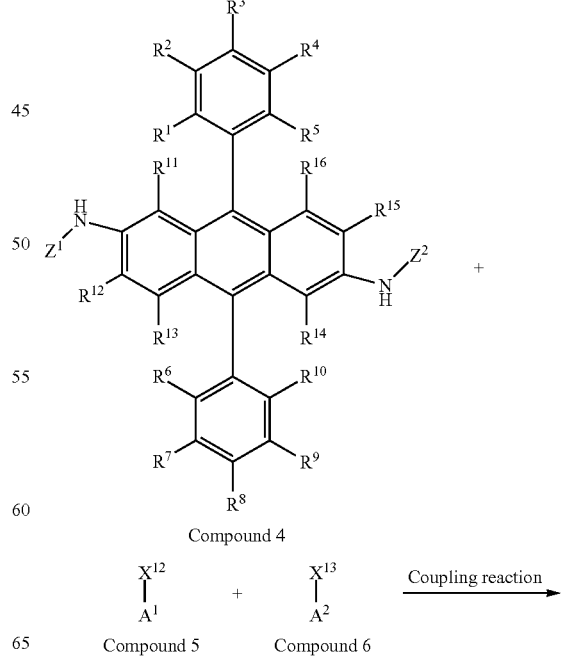

Compound 4

X¹²—A¹ + X¹³—A² →(Coupling reaction)

Compound 5    Compound 6

-continued

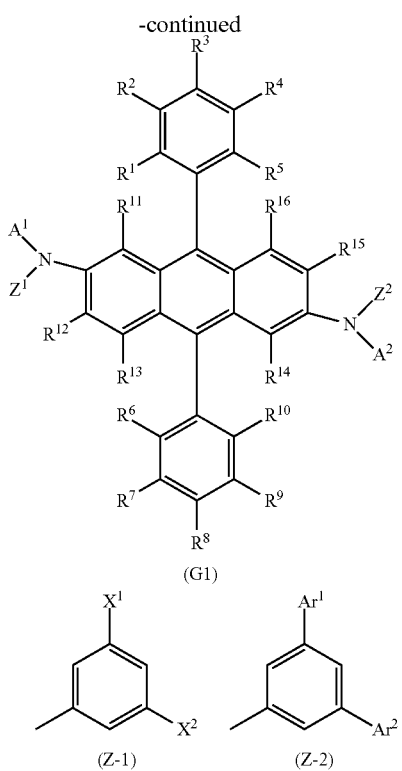

(G1)

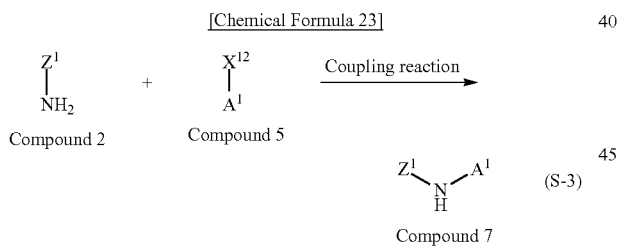

The compound represented by General Formula (G1) can also be synthesized by a method shown in Synthesis Schemes (S-3), (S-4), and (5-5) below.

First, the compound 2 (aniline compound) and the compound 5 (halogenated aryl) are coupled, whereby a compound 7 (amine compound) is obtained (Synthesis Scheme (S-3)).

[Chemical Formula 23]

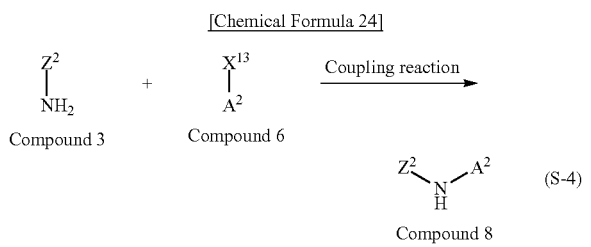

The compound 3 (aniline compound) and the compound 6 (halogenated aryl) are coupled, whereby a compound 8 (amine compound) is obtained (Synthesis Scheme (S-4)).

[Chemical Formula 24]

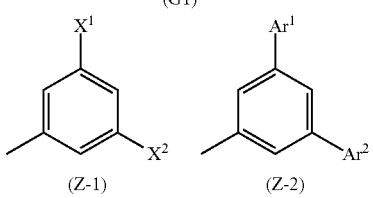

Next, the compound 1, the compound 7 (amine compound), and the compound 8 (amine compound) are coupled, whereby the compound represented by General Formula (G1) is obtained (Synthesis Scheme (S-5)).

[Chemical Formula 25]

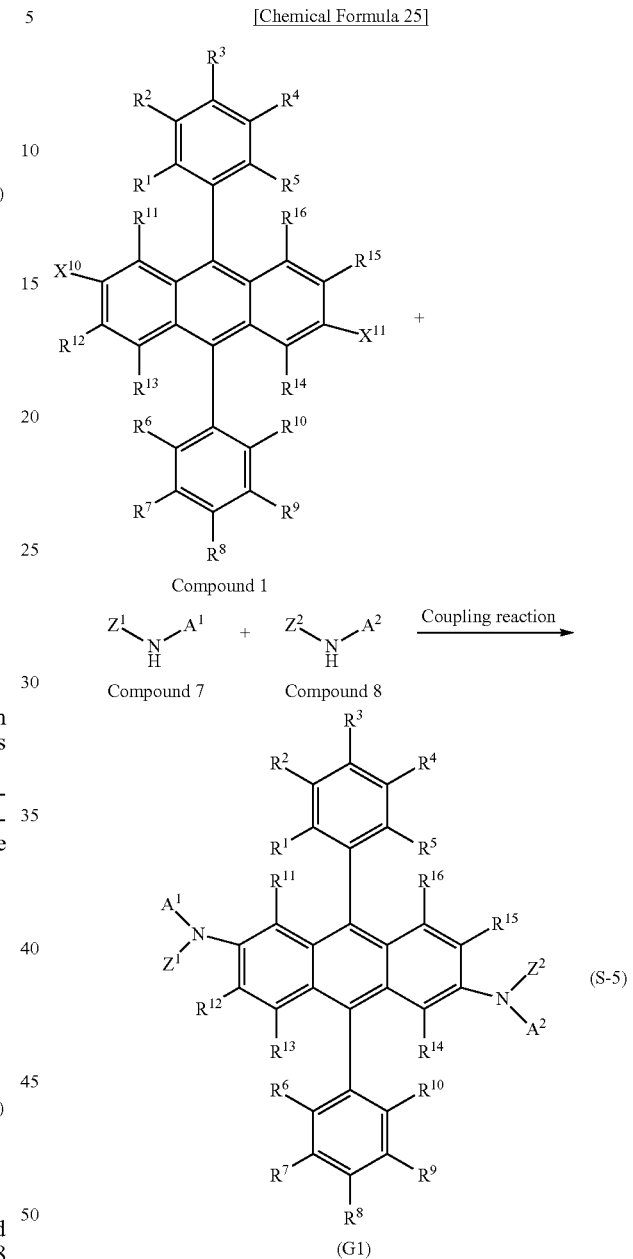

In Synthesis Schemes (S-1) to (S-5), each of $A^1$ and $A^2$ independently represents a substituted or unsubstituted condensed aromatic ring having 10 to 30 carbon atoms, a substituted or unsubstituted condensed heteroaromatic ring having 3 to 30 carbon atoms, or a structure represented by General Formula (Z-1) or General Formula (Z-2); and each of $Z^1$ and $Z^2$ independently has a structure represented by General Formula (Z-1) or (Z-2). In General Formula (Z-1), each of $X^1$ and $X^2$ independently represents any one of an alkyl group having 3 to 10 carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms. Each of $Ar^1$ and $Ar^2$ independently represents a substituted or unsubstituted aromatic hydrocarbon group having 6 to 13 carbon atoms, and at least one of $Ar^1$ and $Ar^2$ includes the same substituent as $X^1$. Each of $R^1$ to $R^{16}$ independently represents any one of hydrogen, an alkyl group having 3 to 10 carbon atoms, a substituted or unsubstituted cycloalkyl group having 3 to 10 carbon atoms, a trialkylsilyl group having 3 to 12 carbon atoms, and a substituted or unsubstituted aryl group having 6 to 25 carbon atoms.

In the case where a Buchwald-Hartwig reaction using a palladium catalyst is employed in Synthesis Schemes (S-1) to (S-5), $X^{10}$ to $X^{13}$ each represent a halogen group or a triflate group. As the halogen, iodine, bromine, or chlorine is preferable. In the reaction, a palladium compound such as bis(dibenzylideneacetone)palladium(0) or palladium(II) acetate and a ligand such as tri(tert-butyl)phosphine, tri(n-hexyl)phosphine, tricyclohexylphosphine, di(1-adamantyl)-n-butylphosphine, or 2-dicyclohexylphosphino-2',6'-dimethoxy-1,1'-biphenyl can be used. In addition, an organic base such as sodium-tert-butoxide, an inorganic base such as potassium carbonate, cesium carbonate, or sodium carbonate, or the like can be used. Furthermore, toluene, xylene, mesitylene, benzene, tetrahydrofuran, dioxane, or the like can be used as a solvent. Reagents that can be used in the reaction are not limited thereto.

The reaction employed in Synthesis Schemes (S-1) to (S-5) is not limited to the Buchwald-Hartwig reaction. A Migita-Kosugi-Stille coupling reaction using an organotin compound, a coupling reaction using a Grignard reagent, an Ullmann reaction using copper or a copper compound, or the like can be used.

In the case where the compound 2 and the compound 3 have different structures in Synthesis Scheme (S-1), it is preferable that the compound 1 and the compound 2 be reacted to form a coupling product and then the coupling product and the compound 3 be reacted. In the case where the compound 1 is reacted with the compound 2 and the compound 3 in different stages, it is preferable that the compound 1 be a dihalogen compound and $X^{10}$ and $X^{11}$ be different halogens and selectively subjected to amination reactions one by one.

Furthermore, in Synthesis Scheme (S-2), it is preferable that the compound 4 and the compound 5 be reacted to form a coupling product and then the coupling product and the compound 6 be reacted.

In Synthesis Scheme (S-5), it is preferable that the compound 1 and the compound 7 be reacted to form a coupling product and then the coupling product and the compound 8 be reacted.

The methods of synthesizing the compounds that is one embodiment of the present invention are described above; however, the present invention is not limited thereto, and another synthesis method may be employed.

Embodiment 2

In this embodiment, examples of light-emitting devices for which a compound of one embodiment of the present invention is preferably used will be described. As illustrated in FIG. 1A, the light-emitting device has a structure in which an EL layer 103 is positioned between a pair of electrodes, a first electrode 101 (corresponding to an anode in FIG. 1A) and a second electrode 102 (corresponding to a cathode in FIG. 1A). The EL layer 103 includes at least a light-emitting layer 113. In addition, functional layers, such as a hole-injection layer 111, a hole-transport layer 112, an electron-transport layer 114, and an electron-injection layer 115, can be provided.

Figure 1B:
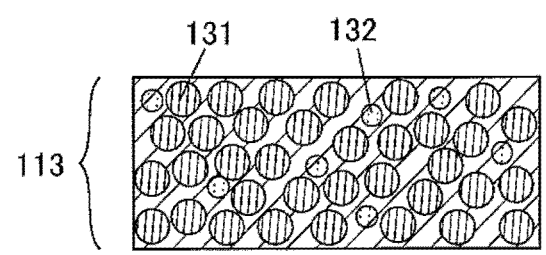
FIG. 1B illustrates a light-emitting layer.

The light-emitting layer 113 contains a light-emitting substance (a guest material) and a host material. In the light-emitting device, voltage application between the pair of electrodes causes injection of electrons and holes from the cathode and the anode, respectively, into the EL layer 103; thus, current flows. At this time, when carriers (electrons and holes) are recombined in the light-emitting layer 113, excitons are generated and excitation energy of the excitons is converted into light emission, whereby light emission can be obtained from the light-emitting device. Note that as illustrated in FIG. 1B, the light-emitting layer 113 in this embodiment contains a compound 132, which is an energy acceptor and functions as a light-emitting substance (a guest material), and a compound 131, which is an energy donor and functions as a host material. In this embodiment, the case where the compound of one embodiment of the present invention is used as a light-emitting substance (a guest material) is described. Note that the light-emitting layer 113 may contain a plurality of compounds functioning as a host material.

Figure 2A:
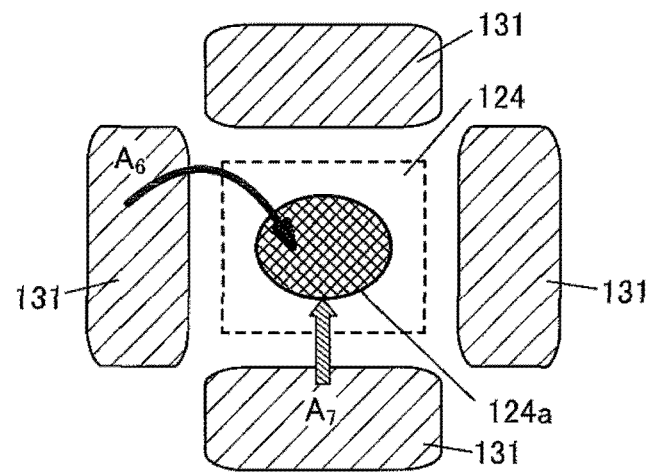
FIG. 2A is a conceptual diagram of energy transfer of a general guest material and a host material.
Figure 2B:
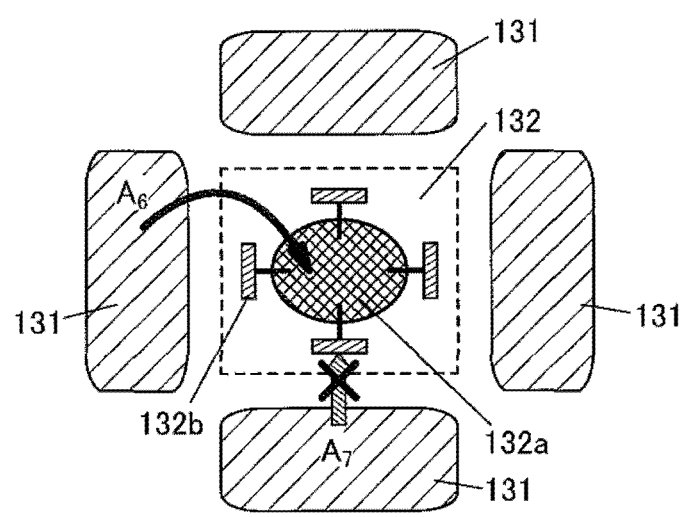
FIG. 2B is a conceptual diagram of energy transfer of a compound of one embodiment of the present invention (guest material) and a host material.

As to the excitons generated by the carrier recombination, the proportion of generation of singlet excitons is 25%, and the proportion of generation of triplet excitons is 75%; thus, it is preferable to make not only singlet excitons but also triplet excitons contribute to the light emission in order to improve the emission efficiency of the light-emitting device. Here, the concept of energy transfer that occurs between the guest material and the host material in the light-emitting layer 113 is described with reference to FIGS. 2A and 2B. Note that FIG. 2A illustrates a structure of a general guest material (a fluorescent substance) and a concept of energy transfer between the guest material and the host material when the general guest material is used. FIG. 2B illustrates a structure of the compound 132 of one embodiment of the present invention and a concept of energy transfer between the guest material and the host material when the compound 132 is used as a guest material.

FIG. 2A illustrates a state where the compound 131 serving as a host material and a fluorescent substance 124 serving as a guest material are present. Note that the fluorescent substance 124 is a general fluorescent substance, and includes a luminophore 124a but does not include a protective group.

FIG. 2B illustrates a state where the compound 131 serving as a host material and the compound (fluorescent substance) 132, which is one embodiment of the present invention, are present. Note that the compound 132 is a fluorescent substance which functions as an energy acceptor in the light-emitting device, and includes a luminophore 132a and a protective group 132b. Note that the protective group 132b has a function of making the luminophore 132a and the compound (host material) 131 away from each other by keeping a distance with which energy transfer from the compound (host material) 131 to the luminophore 132a based on the Dexter mechanism is less likely to occur.

As illustrated in FIGS. 2A and 2B, in the light-emitting layer 113, the compound 131, which serves as a host material, and the fluorescent substance 124 and the compound (fluorescent substance) 132, which serve as guest materials, are close to each other. The distance between the luminophore 124*a* and the compound 131 is short when the fluorescent substance 124 does not include a protective group, and thus energy transfer based on the Förster mechanism (Route $A_6$ in FIG. 2A) and energy transfer based on the Dexter mechanism (Route $A_7$ in FIG. 2A) both can occur as the energy transfer from the compound 131 to the fluorescent substance 124, as illustrated in FIG. 2A. In the case where the guest material is a fluorescent material, even when the triplet excitation energy transfer from the host material to the guest material is caused by the Dexter mechanism and the triplet excited state of the guest material is generated, non-radiative decay of the triplet excitation energy occurs, which might be a factor of reducing the emission efficiency of the light-emitting device.

In contrast, in FIG. 2B, since the compound (fluorescent substance) 132 serving as a guest material includes the protective group 132*b*, the distance between the luminophore 132*a* and the compound 131 serving as a host material can be long. This can inhibit energy transfer (Route $A_7$) by the Dexter mechanism.

Here, the luminophore 124*a* included in the fluorescent substance 124 illustrated in FIG. 2A and the luminophore 132*a* included in the compound (fluorescent substance) 132 illustrated in FIG. 2B are described. The luminophore (124*a*, 132*a*) refers to an atomic group (skeleton) that causes light emission in a fluorescent substance. The luminophore (124*a*, 132*a*) generally has a π bond and preferably includes an aromatic ring, more preferably includes a condensed aromatic ring or a condensed heteroaromatic ring. Examples of the condensed aromatic ring or the condensed heteroaromatic ring included in the luminophore (124*a*, 132*a*) include a phenanthrene ring, a stilbene ring, an acridone ring, a phenoxazine ring, and a phenothiazine ring. Specific examples are a naphthalene ring, an anthracene ring, a fluorene ring, a chrysene ring, a triphenylene ring, tetracene ring, a pyrene ring, a perylene ring, a quinoline ring, a benzimidazole ring, a quinazoline ring, a carbazole ring, an acridine ring, a coumalin ring, a quinacridone ring, a naphthobisbenzofuran ring, a dibenzofuran ring, a dibenzothiophene ring, an indenocarbazole ring, an indolocarbazole ring, and a dibenzo carbazole ring. Note that an anthracene skeleton is particularly preferable as the luminophore 132*a* included in the compound 132 of one embodiment of the present invention.

The protective group 132*b* included in the compound (fluorescent substance) 132 illustrated in FIG. 2B preferably has a higher T1 level than the luminophore 132*a* and the compound 131 serving as a host material have. Note that a specific example of the protective group 132*b* included in the compound 132 of one embodiment of the present invention is preferably a cycloalkyl group having a bridge structure and having 7 to 10 carbon atoms. In addition, specific examples thereof include an alkyl group having 3 to carbon atoms, a substituted or unsubstituted cycloalkyl group having 3 to 10 carbon atoms, and a trialkylsilyl group having 3 to 12 carbon atoms. The protective group 132*b* as described above leads to a bulky structure; accordingly, the distance between the luminophore 132*a* of the compound 132 serving as a guest material and the compound 131 serving as a host material can be long.

Next, a structure of the light-emitting layer of the light-emitting device of one embodiment of the present invention will be described.

<Structure Example 1 of Light-Emitting Layer>

Figure 3A:
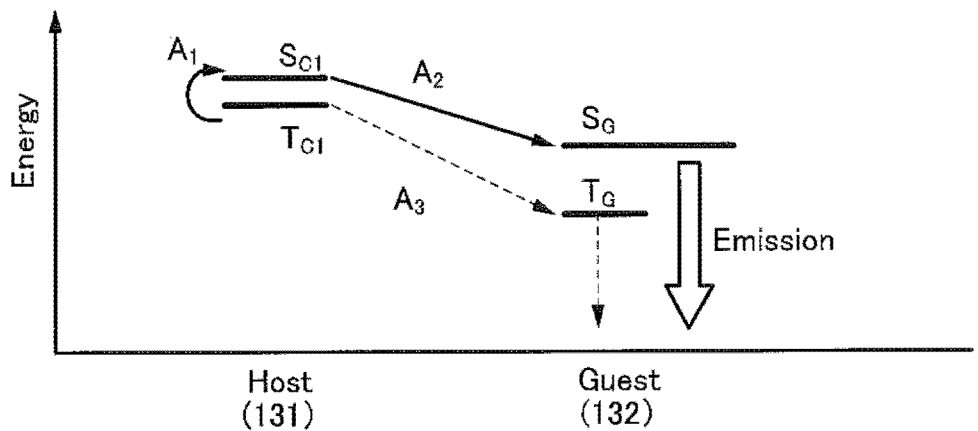
FIGS. 3A to 3C are each a conceptual diagram of energy transfer between compounds in a light-emitting layer.

This structure example shows the light-emitting layer 113 in the light-emitting device, which includes the compound 131 serving as a host material and the compound 132 serving as a light-emitting substance (guest material). A TADF material is used as the compound 131, and a fluorescent substance is used as the compound 132 serving as the light-emitting substance (guest material). Thus, it is preferable that a compound of one embodiment of the present invention be used as the compound 132 that is a fluorescent substance. FIG. 3A shows an example of the correlation of energy levels in the light-emitting layer 113 in this structure example. The following explains what terms and numerals in FIG. 3A represent:

Host (131): the compound 131;
Guest (132): the compound 132;
$T_{C1}$: the T1 level of the compound 131;
$S_{C1}$: the S1 level of the compound 131;
$S_G$: the S1 level of the compound 132; and
$T_G$: the T1 level of the compound 132.

In this structure example, the compound 131 is a TADF material and thus has a function of converting triplet excitation energy into singlet excitation energy by upconversion (Route $A_1$ in FIG. 3A). The singlet excitation energy of the compound 131 is rapidly transferred to the compound 132 (Route $A_2$ in FIG. 3A). At this time, the preferable relation between the $S_{C1}$ of the compound 131 and the $S_G$ of the compound 132 is $S_{C1} \geq S_G$. Note that the $S_{C1}$ is energy with a wavelength of the line obtained by extrapolating a tangent to the fluorescent spectrum of the compound 131 at a tail on the short wavelength side, and $S_G$ is energy with a wavelength of the absorption edge of the absorption spectrum of the compound 132.

As described above, by energy transfer of the triplet excitation energy generated in the compound 131 to the S1 level of the compound 132 serving as a guest material through Route $A_1$ and Route $A_2$, the compound 132 can emit light efficiently and the emission efficiency of the light-emitting device can be increased. In Route $A_2$, the compound 131 serves as an energy donor and the compound 132 serves as an energy acceptor. Note that in the light-emitting layer 113 in the light-emitting device of this structure example, the above routes might compete with a route through which the triplet excitation energy generated in the compound 131 is transferred to the T1 level of the compound 132 (Route $A_3$ in FIG. 3A). When such energy transfer (Route $A_3$) occurs, the compound 132 that is a fluorescent substance cannot make the triplet excitation energy contribute to light emission, which reduces the emission efficiency of the light-emitting device.

In general, as mechanisms of the intermolecular energy transfer, the Förster mechanism (dipole-dipole interaction) and the Dexter mechanism (electron exchange interaction) are known. The Dexter mechanism is generated dominantly when the distance between the compound serving as an energy donor and the compound serving as an energy acceptor is 1 nm or less. Therefore, when the concentration of the compound serving as an energy acceptor is increased, the Dexter mechanism is likely to be generated. Accordingly, when the compound 132 serving as an energy acceptor is a fluorescent material having a low triplet excitation energy level and the concentration of the compound 132 is high as in this structure example, as to the triplet excitation energy of the compound 131 serving as an energy donor, energy transfer by the Dexter mechanism through Route $A_3$ and non-radiative decay of the triplet excitation energy after the energy transfer are dominant. Therefore, in order to suppress the energy transfer through Route $A_3$, it is important to make the distance between the compound 131 and the compound 132 long enough not to cause the energy transfer by the Dexter mechanism.

The T1 level ($T_G$) of the compound 132 serving as an energy acceptor is derived from the luminophore included in the compound 132 in many cases. Therefore, it is important to increase the distance between the compound 131 and the luminophore included in the compound 132 in order to suppress energy transfer through Route $A_3$ in the light-emitting layer 113.

In general, as an example of a method of lengthening the distance between an energy donor and a luminophore included in an energy acceptor, lowering the concentration of the energy acceptor in the mixed film is given. However, lowering the concentration of the energy acceptor inhibits not only energy transfer from the energy donor to the energy acceptor based on the Dexter mechanism but also energy transfer by the Förster mechanism. In that case, the emission efficiency or reliability of the light-emitting device declines because Route $A_2$ is based on the Förster mechanism. In contrast, the compound of one embodiment of the present invention includes a luminophore and a protective group in its structure. In the case where the compound of one embodiment of the present invention serves as the energy acceptor in the light-emitting layer 113, the protective group has a function of lengthening the distance between another energy donor and the luminophore. Thus, in the case where the compound of one embodiment of the present invention is used as the compound 132, the distance between the compound 132 and the compound 131 can be long. When the distance between the energy donor and the energy acceptor is less than or equal to 1 nm, the Dexter mechanism is dominant. When the distance is greater than or equal to 1 nm and less than or equal to 10 nm, the Förster mechanism is dominant. For this reason, the protective group is preferably a bulky substituent ranging from 1 nm to 10 nm from the luminophore. As the protective group included in the compound of one embodiment of the present invention, the above-described protective group is preferably used. With the use of the compound of one embodiment of the present invention as the compound 132, even when the concentration of the compound 132 is increased, the rate of energy transfer by the Förster mechanism can be increased while the energy transfer by the Dexter mechanism is suppressed. In other words, singlet excitation energy transfer (Route $A_2$) from the S1 level ($S_{C1}$) of the compound 131 to the S1 level ($S_G$) of the compound 132 is likely to occur while triplet excitation energy transfer (Route $A_3$: energy transfer by the Dexter mechanism) from the compound 131 to the T1 level ($T_G$) of the compound 132 is less likely to occur. Thus, the emission efficiency of the light-emitting device can be increased while a decrease in emission efficiency due to energy transfer through Route $A_3$ can be suppressed. By increasing the rate of energy transfer by the Förster mechanism, the excitation lifetime of the energy acceptor in the light-emitting layer is shortened, leading to an improvement in reliability of the light-emitting device. Specifically, the concentration of the compound 132 in the light-emitting layer 113 is preferably greater than or equal to 2 wt % and less than or equal to 50 wt %, more preferably greater than or equal to 5 wt % and less than or equal to 30 wt %, further more preferably greater than or equal to 5 wt % and less than or equal to 20 wt % of the compound 131 serving as an energy donor.

<Structure Example 2 of Light-Emitting Layer>

Figure 3B:
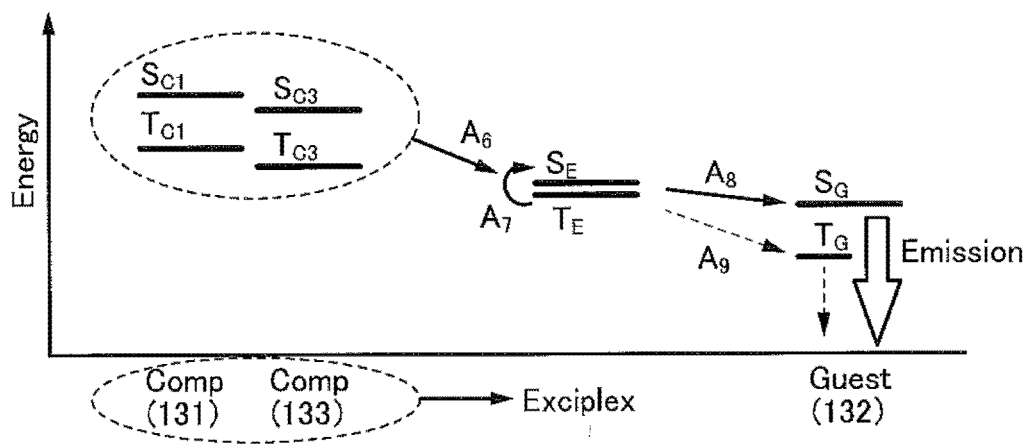

This structure example shows the light-emitting layer 113 in the light-emitting device, which includes the compound 131, the compound 132, and a compound 133. A combination of the compound 131 and the compound 133 forms an exciplex. A fluorescent substance (ExEF) is used as the compound 132 serving as the light-emitting substance (guest material). Thus, it is preferable that a compound of one embodiment of the present invention be used as the compound 132 that is a fluorescent substance. FIG. 3B shows an example of the correlation of energy levels in the light-emitting layer 113 in this structure example. The following explains what terms and numerals in FIG. 3B represent:

Comp (131): the compound 131;
Comp (133): the compound 133;
Guest (132): the compound 132;
$SC_1$: the S1 level of the compound 131;
$T_{C1}$: the T1 level of the compound 131;
$S_{C3}$: the S1 level of the compound 133;
$T_{C3}$: the T1 level of the compound 133;
$S_G$: the S1 level of the compound 132;
$T_G$: the T1 level of the compound 132;
$S_E$: the S1 level of the exciplex; and
$T_E$: the T1 level of the exciplex.

Although any combination of the compound 131 and the compound 133 that can form an exciplex is acceptable, it is preferable that one of them be a compound having a hole-transport property and the other be a compound having an electron-transport property. In that case, a donor-acceptor exciplex is easily formed; thus, efficient formation of an exciplex is possible. When the compounds 131 and 133 are a combination of a compound having a hole-transport property and a compound having an electron-transport property, the carrier balance can be easily controlled depending on the mixing ratio. Specifically, the weight ratio of the compound having a hole-transport property to the compound having an electron-transport property is preferably within a range of 1:9 to 9:1. Since the carrier balance can be easily controlled with the above composition, a carrier recombination region can also be controlled easily.

For the combination of host materials for forming an exciplex efficiently, it is preferable that the HOMO level of one of the compounds 131 and 133 be higher than that of the other compound and the LUMO level of the one of the compounds be higher than that of the other compound. Note that the HOMO level of the compound 131 may be equivalent to that of the compound 133, or the LUMO level of the compound 131 may be equivalent to that of the compound 133.

Note that the LUMO levels and the HOMO levels of the compounds can be derived from the electrochemical characteristics (the reduction potentials and the oxidation potentials) of the compounds that are measured by cyclic voltammetry (CV).

As illustrated in FIG. 3B, the S1 level ($S_E$) and the T1 level ($T_E$) of the exciplex formed by the compound 131 and the compound 133 are energy levels adjacent to each other (see Route $A_6$ in FIG. 3B).

Since the excitation energy levels ($S_E$ and $T_E$) of the exciplex are lower than the S1 levels ($S_{C1}$ and $S_{C3}$) of the substances (the compounds 131 and 133) that form the exciplex, an excited state can be formed with lower excitation energy. Accordingly, the driving voltage of the light-emitting device can be reduced.

Since the S1 level ($S_E$) and the T1 level ($T_E$) of the exciplex are adjacent to each other, reverse intersystem crossing occurs easily; the exciplex has a TADF property. Thus, the exciplex has a function of converting triplet excitation energy into singlet excitation energy by upconversion (Route $A_7$ in FIG. 3B). The singlet excitation energy of the exciplex can be rapidly transferred to the compound 132 (Route $A_8$ in FIG. 3B). At this time, $S_E \geq S_G$ is preferable. In Route $A_8$, the exciplex serves as an energy donor, and the compound 132 serves as an energy acceptor. Specifically, $S_E \geq S_G$ is preferably satisfied when $S_E$ is energy with a wavelength of the line obtained by extrapolating a tangent to the fluorescent spectrum of the exciplex at a tail on the short wavelength side, and $S_G$ is energy with a wavelength of the absorption edge of the absorption spectrum of the compound 132.

In order to improve the TADF property, it is preferable that the T1 levels of both of the compounds 131 and 133, that is, $T_{C1}$ and $T_{C3}$ be higher than or equal to $T_E$. As the index for such $T_{C1}$ and $T_{C3}$, the emission peak wavelengths of the phosphorescent spectra of the compound 131 and the compound 133 on the shortest wavelength side are each preferably less than or equal to the maximum emission peak wavelength of the exciplex. When the level of energy with a wavelength of the line obtained by extrapolating a tangent to the fluorescent spectrum of the exciplex at a tail on the short wavelength side is $S_E$, the level of energy with a wavelength of the line obtained by extrapolating a tangent to the phosphorescent spectrum of the compound 131 at a tail on the short wavelength side is $T_{C1}$, and the level of energy with a wavelength of the line obtained by extrapolating a tangent to the phosphorescent spectrum of the compound 133 at a tail on the short wavelength side is $T_{C3}$, $S_E - T_{C1} \leq 0.2$ eV and $S_E - T_{C3} \leq 0.2$ eV are preferably satisfied.

The triplet excitation energy generated in the light-emitting layer 113 is transferred to the S1 level of the compound 132 serving as a guest material through Route $A_6$ and Route $A_8$, whereby the compound 132 can emit light. Thus, the use of a combination of materials that form an exciplex in the light-emitting layer 113 can increase the emission efficiency of the fluorescent light-emitting device. However, the above routes might compete with a route through which the triplet excitation energy generated in the light-emitting layer 113 is transferred to the T1 level of the compound 132 (Route $A_9$ in FIG. 3B). When such energy transfer (Route $A_9$) occurs, the compound 132 that is a fluorescent substance cannot make the triplet excitation energy contribute to light emission, which reduces the emission efficiency of the light-emitting device.

In order to suppress such energy transfer (Route $A_9$ in FIG. 313), as described in the structure example 1, it is important that the distance between the compound 132 and the exciplex formed by the compound 131 and the compound 133 be long, and that the distance between the exciplex and the luminophore included in the compound 132 be long.

The compound of one embodiment of the present invention includes a luminophore and a protective group in its structure. In the case where the compound of one embodiment of the present invention serves as the energy acceptor in the light-emitting layer 113, the protective group has a function of lengthening the distance between another energy donor and the luminophore. Thus, in the case where the compound of one embodiment of the present invention is used as the compound 132 in this structure example, the distance between the compound 132 and an exciplex formed by the compound 131 and the compound 133 can be long even when the concentration of the compound 132 is increased; accordingly, the rate of energy transfer by the Förster mechanism can be increased while energy transfer by the Dexter mechanism can be suppressed. With the use of the compound of one embodiment of the present invention as the compound 132, triplet excitation energy transfer (Route $A_6$ and Route $A_8$ in FIG. 3B) from the exciplex to the S1 level ($S_G$) of the compound 132 is likely to occur while triplet excitation energy transfer (Route $A_9$: energy transfer by the Dexter mechanism) from the exciplex to the T1 level ($T_G$) of the compound 132 is less likely to occur. Thus, the emission efficiency of the light-emitting device can be increased while a decrease in emission efficiency due to energy transfer through Route $A_9$ can be suppressed. Furthermore, the reliability of the light-emitting device can be improved.

Note that in this specification, Route $A_6$, Route $A_7$, and Route $A_8$, which are described above, are also referred to as exciplex-singlet energy transfer (ExSET) or exciplex-enhanced fluorescence (ExEF). In other words, in the light-emitting layer 113 in this specification, excitation energy is supplied from the exciplex to the fluorescent material.

<Structure Example 3 of Light-Emitting Layer>

Figure 3C:
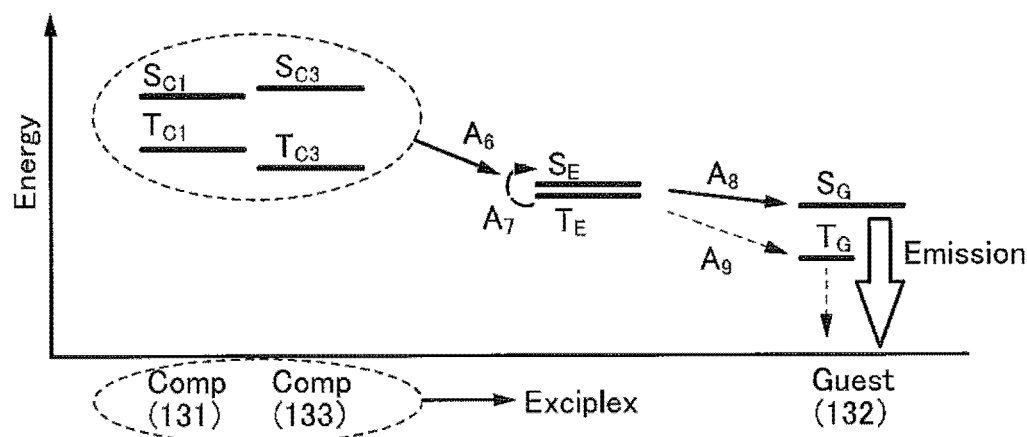

This structure example shows the light-emitting layer 113 in the light-emitting device, which includes the compound 131, the compound 132, and a compound 133. A combination of the compound 131 and the compound 133 forms an exciplex. A fluorescent substance (ExEF) is used as the compound 132 serving as the light-emitting substance (guest material). In addition, this structure example is different from the structure example 2 in that the compound 133 is a phosphorescent material. It is preferable that a compound of one embodiment of the present invention be used as the compound 132 that is a fluorescent substance. FIG. 3C shows an example of the correlation of energy levels in the light-emitting layer 113 in this structure example. Note that terms and numerals in FIG. 3C are the same as those in FIG. 3B and thus the description thereof is omitted.

In this structure example, a compound containing a heavy atom is used as one of compounds that form an exciplex. Thus, intersystem crossing between a singlet state and a triplet state is promoted. Consequently, an exciplex capable of transition from a triplet excited state to a singlet ground state (that is, capable of emitting phosphorescence) can be formed. In this case, unlike in the case of a typical exciplex, the triplet excitation energy level ($T_E$) of the exciplex is the level of an energy donor; thus, $T_E$ is preferably higher than or equal to the singlet excitation energy level ($S_G$) of the compound 132 serving as a light-emitting material. Specifically, $T_E \geq S_G$ is preferably satisfied when $T_E$ is energy with a wavelength of the line obtained by extrapolating a tangent to the emission spectrum of the exciplex containing a heavy atom at a tail on the short wavelength side and $S_G$ is energy with a wavelength of the absorption edge of the absorption spectrum of the compound 132.

With such correlation of energy levels, the triplet excitation energy of the formed exciplex can be transferred from the triplet excitation energy level of the exciplex ($T_E$) to the singlet excitation energy level of the compound 132 ($S_G$). Note that it is sometimes difficult to clearly distinguish fluorescence and phosphorescence from each other in an emission spectrum because the S1 level and the T1 level ($S_E$ and $T_E$) of the exciplex are adjacent to each other. In that case, fluorescence and phosphorescence can sometimes be distinguished from each other by the emission lifetime.

Note that the phosphorescent material used in the above structure preferably contains a heavy atom such as Ir, Pt, Os, Ru, or Pd. In contrast, in this structure example, the phosphorescent material serves as an energy donor; thus, the quantum yield does not matter. That is, energy transfer from the triplet excitation energy level of the exciplex to the singlet excitation energy level of the guest material is acceptable as long as it is allowable transition. The energy transfer from the phosphorescent material or the exciplex formed using the phosphorescent material to the guest material is preferred, in which case energy transfer from the triplet excitation energy level of the energy donor to the singlet excitation energy level of the guest material (energy acceptor) is allowable transition.

Thus, in the light-emitting layer 113 of the light-emitting device in this structure, the triplet excitation energy of the exciplex is transferred to the S1 level ($S_G$) of the guest material through Route $A_8$ (without passing through Route $A_7$ in FIG. 3C), as illustrated in FIG. 3C. That is, triplet excitation energy and singlet excitation energy can be transferred to the S1 level of the guest material through Route $A_6$ and Route $A_8$. In Route $A_8$, the exciplex serves as an energy donor and the compound 132 serves as an energy acceptor. Note that in the light-emitting layer 113 in the light-emitting device of this structure example, the above routes might compete with a route through which the triplet excitation energy of the exciplex is transferred to the T1 level of the compound 132 (Route $A_9$ in FIG. 3C). When such energy transfer (Route $A_9$) occurs, the compound 132 that is a fluorescent substance cannot make the triplet excitation energy contribute to light emission, which reduces the emission efficiency of the light-emitting device.

In order to suppress such energy transfer (Route $A_9$), as described in the structure example 1, it is important that the distance between the compound 131 and the compound 132 and the distance between the compound 131 and the luminophore included in the compound 132 be long.

The compound of one embodiment of the present invention includes a luminophore and a protective group in its structure. In the case where the compound of one embodiment of the present invention serves as the energy acceptor in the light-emitting layer 113, the protective group has a function of lengthening the distance between another energy donor and the luminophore. Thus, in the case where the compound of one embodiment of the present invention is used as the compound 132 in this structure example, the distance between the compound 132 and an exciplex formed by the compound 131 and the compound 133 can be long even when the concentration of the compound 132 is increased; accordingly, the rate of energy transfer by the Förster mechanism can be increased while energy transfer by the Dexter mechanism can be suppressed. With the use of the compound of one embodiment of the present invention as the compound 132, triplet excitation energy transfer (Route $A_6$ and Route $A_8$) from the exciplex to the S1 level ($S_G$) of the compound 132 is likely to occur while triplet excitation energy transfer (Route $A_9$: energy transfer by the Dexter mechanism) from the exciplex to the T1 level ($T_G$) of the compound 132 is less likely to occur. Thus, the emission efficiency of the light-emitting device can be increased while a decrease in emission efficiency due to energy transfer through Route $A_9$ can be suppressed. Furthermore, the reliability of the light-emitting device can be improved.

<Structure Example 4 of Light-Emitting Layer>

Figure 4A:
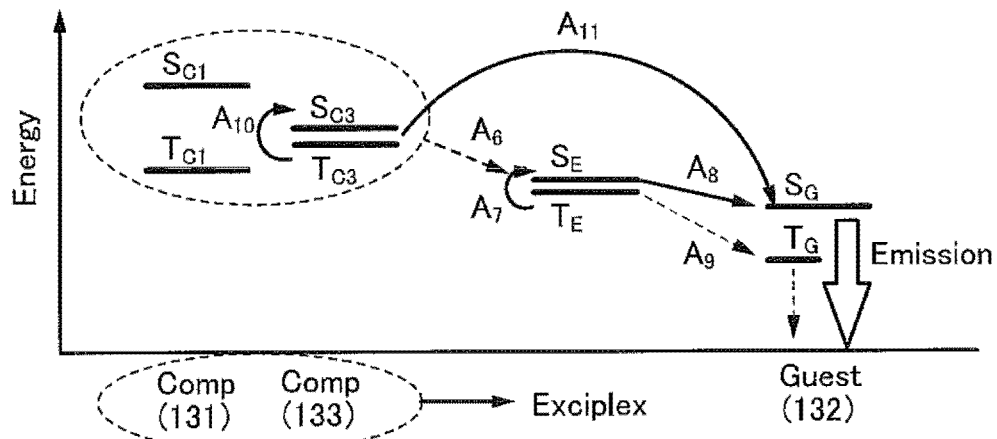
FIGS. 4A to 4C are each a conceptual diagram of energy transfer between compounds in a light-emitting layer.

This structure example shows the light-emitting layer 113 in the light-emitting device, which includes three kinds of substances: the compound 131, the compound 132, and the compound 133. A combination of the compound 131 and the compound 133 forms an exciplex. A fluorescent substance (ExEF) is used as the compound 132 serving as the light-emitting substance (guest material). It is preferable that a compound of one embodiment of the present invention be used as the compound 132 that is a fluorescent substance. Note that this structure example is different from the above structure example 3 in that the compound 133 is a TADF material. FIG. 4A shows an example of the correlation of energy levels in the light-emitting layer 113 in this structure example. Note that terms and numerals in FIG. 4A are the same as those in FIG. 3B and thus the description thereof is omitted.

Since the compound 133 is the TADF material in this structure example, the compound 133 that does not form an exciplex has a function of converting triplet excitation energy into singlet excitation energy by upconversion (Route $A_{10}$ in FIG. 4A). Accordingly, the singlet excitation energy of the compound 133 is rapidly transferred to the compound 132 (Route $A_{11}$ in FIG. 4A). At this time, $S_{C3} \geq S_G$ is preferably satisfied.

Therefore, in the light-emitting layer 113 of the light-emitting device in this structure example, a path in which triplet excitation energy is transferred to the compound 132 serving as a guest material through Route $A_6$ to Route $A_8$ in FIG. 4A and a path in which the triplet excitation energy is transferred to the compound 132 through Route $A_{10}$ and Route $A_{11}$ in FIG. 4A) exist, as in the structure example 3. In this way, there are a plurality of paths through each of which the triplet excitation energy is transferred to the compound 132 that is a fluorescent compound, which can further increase the emission efficiency. In Route $A_8$, the exciplex serves as an energy donor and the compound 132 serves as an energy acceptor. In Route $A_{11}$, the compound 133 serves as an energy donor and the compound 132 serves as an energy acceptor: Note that in the light-emitting layer 113 in the light-emitting device of this structure example, the above routes might compete with a route through which the triplet excitation energy of the exciplex is transferred to the T1 level of the compound 132 (Route $A_9$ in FIG. 4A). When such energy transfer (Route $A_9$) occurs, the compound 132 that is a fluorescent substance cannot make the triplet excitation energy contribute to light emission, which reduces the emission efficiency of the light-emitting device.

In order to suppress such energy transfer (Route $A_9$), as described in the structure example 1, it is important that the distance between the compound 132 and the exciplex formed by the compound 131 and the compound 133 be long, that is, the distance between the exciplex formed by the compound 131 and the compound 133 and the luminophore included in the compound 132 be long.

The compound of one embodiment of the present invention includes a luminophore and a protective group in its structure. In the case where the compound of one embodiment of the present invention serves as the energy acceptor in the light-emitting layer 113, the protective group has a function of lengthening the distance between another energy donor and the luminophore. Thus, in the case where the compound of one embodiment of the present invention is used as the compound 132 in this structure example, the distance between the compound 132 and an exciplex formed by the compound 131 and the compound 133 can be long even when the concentration of the compound 132 is increased; accordingly, the rate of energy transfer by the Förster mechanism can be increased while energy transfer by the Dexter mechanism can be suppressed. With the use of the compound of one embodiment of the present invention as the compound 132, triplet excitation energy transfer (Route $A_6$ and Route $A_8$) from the exciplex to the S1 level ($S_G$) of the compound 132 and triplet excitation energy transfer (Route $A_{10}$ and Route $A_{11}$) from the exciplex to the S1 level ($S_G$) of the compound 132 are likely to occur while triplet excitation energy transfer (Route $A_9$: energy transfer by the Dexter mechanism) from the exciplex to the T1 level ($T_G$) of the compound 132 is less likely to occur. Thus, the emission efficiency of the light-emitting device can be increased while a decrease in emission efficiency due to energy transfer through Route $A_9$ can be suppressed. Furthermore, the reliability of the light-emitting device can be improved.

<Structure Example 5 of Light-Emitting Layer>

Figure 4B:
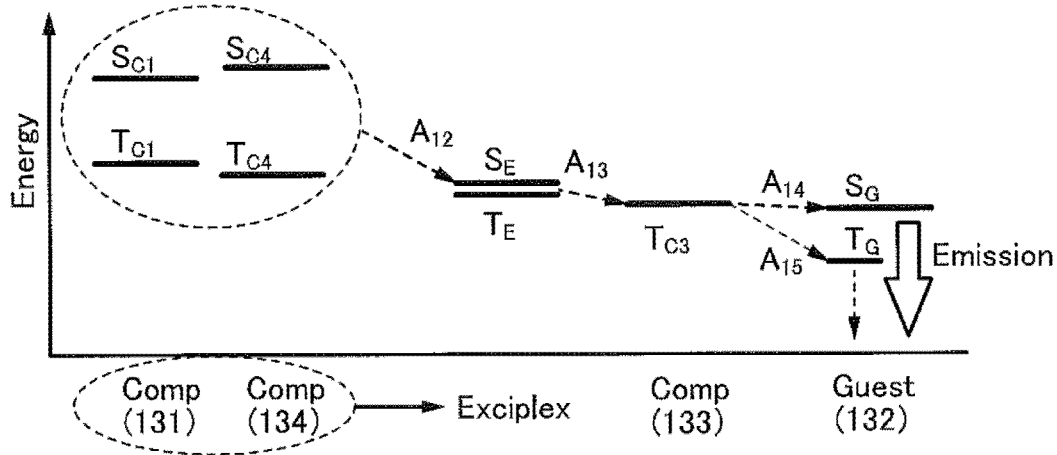

This structure example shows the light-emitting layer 113 in the light-emitting device, which includes four kinds of substances: the compound 131, the compound 132, the compound 133, and the compound 134. The compound 133 has a function of converting triplet excitation energy into light emission, and the case where a phosphorescent substance is used as the compound 133 is described. A combination of the compound 131 and the compound 134 forms an exciplex. A fluorescent substance is used as the compound 132 serving as the light-emitting substance (guest material). It is preferable that a compound of one embodiment of the present invention be used as the compound 132 that is a fluorescent substance. FIG. 4B shows an example of the correlation of energy levels in the light-emitting layer 113 in this structure example. Note that terms and numerals in FIG. 413 are similar to those in FIG. 3B and the other terms and numerals are as follows:

$S_{C4}$: the S1 level of the compound 134; and
$T_{C4}$: the T1 level of the compound 134.

In this structure example, the compound 131 and the compound 134 form an exciplex. The S1 level ($S_E$) and the T1 level ($T_E$) of the exciplex are adjacent to each other (see Route $A_{12}$ in FIG. 4B). Note that when the exciplex formed by the two kinds of substances through the above path loses excitation energy, the two kinds of substances exist as the original different substances.

Since the excitation energy levels ($S_E$ and $T_E$) of the exciplex are lower than the S1 levels ($S_{C1}$ and $S_{C4}$) of the substances (the compounds 131 and 134) that form the exciplex, an excited state can be formed with lower excitation energy. Accordingly, the driving voltage of the light-emitting device can be reduced.

Since the compound 133 is a phosphorescent material, intersystem crossing between a singlet state and a triplet state is allowed. Hence, both the singlet excitation energy and the triplet excitation energy of the exciplex are rapidly transferred to the compound 133 (Route $A_{13}$). At this time, $T_E \geq T_{C3}$ is preferably satisfied.

The triplet excitation energy of the compound 133 is converted into the singlet excitation energy of the compound 132 (Route $A_{14}$). At this time, it is preferable that the relation $T_E \geq T_{C3} \geq S_G$ be satisfied as shown in FIG. 4B because energy is transferred efficiently from the compound 133 to the compound 132. Specifically, $T_{C3} \geq S_G$ is preferably satisfied when $T_{C3}$ is energy with a wavelength of the line obtained by extrapolating a tangent to the phosphorescent spectrum of the compound 133 at a tail on the short wavelength side, and $S_G$ is energy with a wavelength of the absorption edge of the absorption spectrum of the compound 132. In Route $A_{14}$, the compound 133 serves as an energy donor and the compound 132 serves as an energy acceptor.

In this structure example, although any combination of the compound 131 and the compound 134 that can form an exciplex is acceptable, it is preferable that one of them be a compound having a hole-transport property and the other be a compound having an electron-transport property.

For the combination of host materials for forming an exciplex efficiently, it is preferable that the HOMO level of one of the compounds 131 and 134 be higher than that of the other compound and the LUMO level of the one of the compounds be higher than that of the other compound.

The correlation of energy levels of the compounds 131 and 134 is not limited to that shown in FIG. 4B. That is, the singlet excitation energy level ($S_{C1}$ of the compound 131 may be higher or lower than the singlet excitation energy level ($S_{C4}$) of the compound 134. The triplet excitation energy level ($T_{C1}$) of the compound 131 may be higher or lower than the triplet excitation energy level ($T_{C4}$) of the compound 134.

In the light-emitting device in this structure example, the compound 131 preferably includes a π-electron deficient skeleton. Such a composition lowers the LUMO level of the compound 131, which is suitable for forming an exciplex.

In the light-emitting device in this structure example, the compound 131 preferably includes a π-electron rich skeleton. Such a composition increases the HOMO level of the compound 131, which is suitable for forming an exciplex.

The compound of one embodiment of the present invention includes a luminophore and a protective group in its structure. In the case where the compound of one embodiment of the present invention serves as the energy acceptor in the light-emitting layer 113, the protective group has a function of lengthening the distance between another energy donor and the luminophore. Thus, in the case where the compound of one embodiment of the present invention is used as the compound 132, the distance between the compound 133 and the compound 132 can be long. With the use of the compound of one embodiment of the present invention as the compound 132, triplet excitation energy transfer (Route $A_{14}$) from the compound 133 to the S1 level ($S_G$) of the compound 132 is likely to occur while triplet excitation energy transfer (Route $A_{15}$: energy transfer by the Dexter mechanism) from the compound 133 to the T1 level ($T_G$) of the compound 132 is less likely to occur. Thus, the emission efficiency of the light-emitting device can be increased while a decrease in emission efficiency due to energy transfer through Route $A_{15}$ can be suppressed.

In this structure example, by increasing the concentration of the compound 132 serving as an energy acceptor, the rate of energy transfer by the Förster mechanism can be increased while the energy transfer by the Dexter mechanism is suppressed. By increasing the rate of energy transfer by the Förster mechanism, the excitation lifetime of the energy acceptor in the light-emitting layer is shortened, leading to an improvement in reliability of the light-emitting device. Specifically, the concentration of the compound 132 in the light-emitting layer 113 is preferably greater than or equal to 2 wt % and less than or equal to 50 wt %, more preferably greater than or equal to 5 wt % and less than or equal to 30 wt %, further more preferably greater than or equal to 5 wt % and less than or equal to 20 wt % of the compound 133 serving as an energy donor.

Note that in this specification, Route Are and Route $A_{13}$, which are described above, are also referred to as exciplex-triplet energy transfer (ExTET). That is, in the light-emitting layer 113 in this specification, excitation energy is supplied from the exciplex to the compound 133.

<Structure Example 6 of Light-Emitting Layer>

Figure 4C:
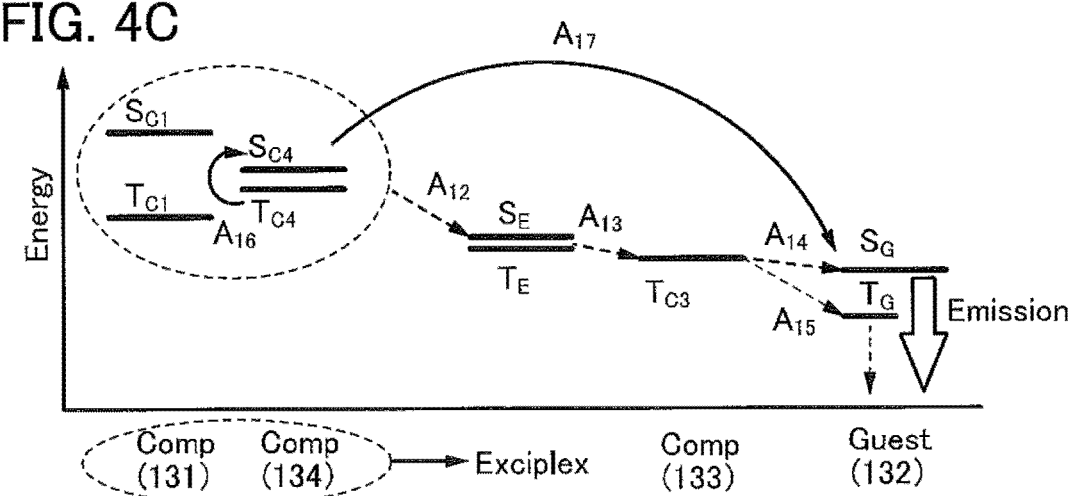

This structure example shows the light-emitting layer 113 in the light-emitting device, which includes four kinds of substances: the compound 131, the compound 132, the compound 133, and the compound 134. The compound 133 has a function of converting triplet excitation energy into light emission, and the case where a phosphorescent substance is used as the compound 133 is described. A combination of the compound 131 and the compound 134 forms an exciplex. A fluorescent substance is used as the compound 132 serving as the light-emitting substance (guest material). It is preferable that a compound of one embodiment of the present invention be used as the compound 132 that is a fluorescent substance. Note that this structure example is different from the above structure example 5 in that the compound 134 is a TADF material. FIG. 4C shows an example of the correlation of energy levels in the light-emitting layer 113 in this structure example. Note that terms and numerals in FIG. 4C are the same as those in FIG. 3B and FIG. 4B and thus the description thereof is omitted.

Since the compound 134 is the TADF material in this structure example, the compound 134 that does not form an exciplex has a function of converting triplet excitation energy into singlet excitation energy by upconversion (Route $A_{16}$ in FIG. 4C). Accordingly, the singlet excitation energy of the compound 134 is rapidly transferred to the compound 132 (Route $A_{17}$ in FIG. 4C). At this time, $S_{C4} \geq S_G$ is preferably satisfied. Specifically, $S_{C4} \geq S_G$ is preferably satisfied when $S_{C4}$ is energy with a wavelength of the line obtained by extrapolating a tangent to the fluorescent spectrum of the compound 134 at a tail on the short wavelength side, and $S_G$ is energy with a wavelength of the absorption edge of the absorption spectrum of the compound 132.

Therefore, in the light-emitting layer 113 of the light-emitting device in this structure example, a path in which triplet excitation energy is transferred to the compound 132 serving as a guest material through Route $A_{12}$ to Route $A_{14}$ in FIG. 4C and a path in which the triplet excitation energy is transferred to the compound 132 through Route $A_{16}$ and Route $A_{17}$ in FIG. 4C) exist, as in the structure example 5. In this way, there are a plurality of paths through each of which the triplet excitation energy is transferred to the compound 132 that is a fluorescent compound, which can further increase the emission efficiency. In Route $A_{14}$, the compound 133 serves as an energy donor and the compound 132 serves as an energy acceptor. In Route $A_{17}$, the compound 134 serves as an energy donor and the compound 132 serves as an energy acceptor. Note that in the light-emitting layer 113 in the light-emitting device of this structure example, the above routes might compete with a route through which the triplet excitation energy of the compound 133 is transferred to the T1 level of the compound 132 (Route $A_{15}$ in FIG. 4C). When such energy transfer (Route $A_{15}$) occurs, the compound 132 that is a fluorescent substance cannot make the triplet excitation energy contribute to light emission, which reduces the emission efficiency of the light-emitting device.

In order to suppress such energy transfer (Route $A_{15}$), as described in the structure example 1, it is important that the distance between the compound 133 and the compound 132, that is, the distance between the compound 133 and the luminophore included in the compound 132 be long.

The compound of one embodiment of the present invention includes a luminophore and a protective group in its structure. In the case where the compound of one embodiment of the present invention serves as the energy acceptor in the light-emitting layer 113, the protective group has a function of lengthening the distance between another energy donor and the luminophore. Thus, in the case where the compound of one embodiment of the present invention is used as the compound 132 in this structure example, the distance between the compound 133 and the compound 132 can be long even when the concentration of the compound 132 is increased; accordingly, the rate of energy transfer by the Förster mechanism can be increased while energy transfer by the Dexter mechanism can be suppressed. With the use of the compound of one embodiment of the present invention as the compound 132, triplet excitation energy transfer (Route $A_{12}$, Route $A_{13}$, and Route $A_{14}$) from the exciplex to the S1 level ($S_G$) of the compound 132 and triplet excitation energy transfer (Route $A_{16}$ and Route $A_{17}$) from the compound 133 to the S1 level ($S_G$) of the compound 132 are likely to occur while triplet excitation energy transfer (Route $A_{15}$: energy transfer by the Dexter mechanism) from the compound 133 to the T1 level ($T_G$) of the compound 132 is less likely to occur. Thus, the emission efficiency of the light-emitting device can be increased while a decrease in emission efficiency due to energy transfer through Route $A_{15}$ can be suppressed. Furthermore, the reliability of the light-emitting device can be improved.

<Structure Example 7 of Light-Emitting Layer>

Figure 5A:
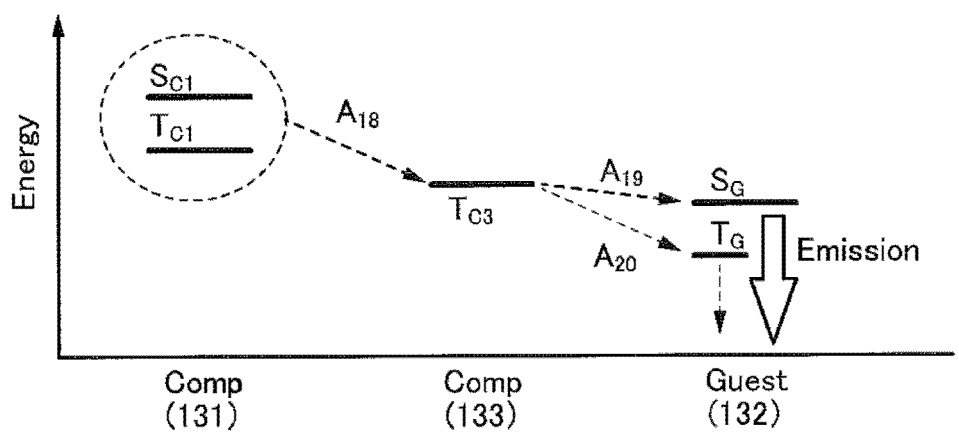
FIGS. 5A and 5B are each a conceptual diagram of energy transfer between compounds in a light-emitting layer.

This structure example shows the light-emitting layer 113 in the light-emitting device, which includes the compound 131, the compound 132, and the compound 133. The compound 133 has a function of converting triplet excitation energy into light emission, and the case where a phosphorescent substance is used as the compound 133 is described. A fluorescent substance is used as the compound 132 serving as the light-emitting substance (guest material). It is preferable that a compound of one embodiment of the present invention be used as the compound 132 that is a fluorescent substance. FIG. 5A shows an example of the correlation of energy levels in the light-emitting layer 113 in this structure example. The following explains what terms and numerals in FIG. 5A represent:

Comp (131): the compound 131;
Comp (133): the compound 133;
Guest (132): the compound 132;
$S_{C1}$: the S1 level of the compound 131;
$T_{C1}$: the T1 level of the compound 131;
$T_{C3}$: the T1 level of the compound 133;
$T_G$: the T1 level of the compound 132; and
$S_G$: the S1 level of the compound 132.

In this structure example, carrier recombination occurs mainly in the compound 131, whereby singlet excitons and triplet excitons are generated. When a phosphorescent substance having a relation $T_{C3} \geq T_{C1}$ is selected as the compound 133, singlet excitation energy and triplet excitation energy generated in the compound 131 can be transferred to the $T_{C3}$ level of the compound 133 (Route $A_{18}$ in FIG. 5A). Some of the carriers can be recombined also in the compound 133.

Note that the phosphorescent substance used in the above structure preferably contains a heavy atom such as Ir, Pt, Os, Ru, or Pd. A phosphorescent substance is preferably used as the compound 133, in which case energy transfer from the triplet excitation energy level of the energy donor to the singlet excitation energy level of the guest material (energy acceptor) is allowable transition. Thus, the triplet excitation energy of the compound 133 can be transferred to the S1 level ($S_G$) of the guest material through the path of Route $A_{19}$. In Route $A_{19}$, the compound 133 serves as an energy donor and the compound 132 serves as an energy acceptor. In that case, $T_{C3} \geq S_G$ is preferably satisfied because the excitation energy of the compound 133 is efficiently transferred to the singlet excited state of the compound 132 serving as a guest material. Specifically, $T_{C3} \geq S_G$ is preferably satisfied when $T_{C3}$ is the level of energy with a wavelength of the line obtained by extrapolating a tangent to the phosphorescent spectrum of the compound 133 at a tail on the short wavelength side and $S_G$ is the level of energy with a wavelength of the absorption edge of the absorption spectrum of the compound 132. Note that in the light-emitting layer 113 in the light-emitting device of this structure example, the above routes might compete with a route through which the triplet excitation energy of the compound 133 is transferred to the T1 level of the compound 132 (Route $A_{20}$ in FIG. 5A). When such energy transfer (Route $A_{20}$) occurs, the compound 132 that is a fluorescent substance cannot make the triplet excitation energy contribute to light emission, which reduces the emission efficiency of the light-emitting device.

In order to suppress such energy transfer (Route $A_{20}$), as described in the structure example 1, it is important that the distance between the compound 133 and the compound 132, that is, the distance between the compound 133 and the luminophore included in the compound 132 be long.

The compound of one embodiment of the present invention includes a luminophore and a protective group in its structure. In the case where the compound of one embodiment of the present invention serves as the energy acceptor in the light-emitting layer 113, the protective group has a function of lengthening the distance between another energy donor and the luminophore. Thus, in the case where the compound of one embodiment of the present invention is used as the compound 132 in this structure example, the distance between the compound 133 and the compound 132 can be long even when the concentration of the compound 132 is increased; accordingly, the rate of energy transfer by the Förster mechanism can be increased while energy transfer by the Dexter mechanism can be suppressed. With the use of the compound of one embodiment of the present invention as the compound 132, triplet excitation energy transfer (Route $A_{19}$) from the compound 133 to the S1 level ($S_G$) of the compound 132 is likely to occur while triplet excitation energy transfer (Route $A_{20}$: energy transfer by the Dexter mechanism) from the compound 133 to the T1 level ($T_G$) of the compound 132 is less likely to occur. Thus, the emission efficiency of the light-emitting device can be increased while a decrease in emission efficiency due to energy transfer through Route $A_{20}$ can be suppressed. Furthermore, the reliability of the light-emitting device can be improved.

<Structure Example 8 of Light-Emitting Layer>

Figure 5B:
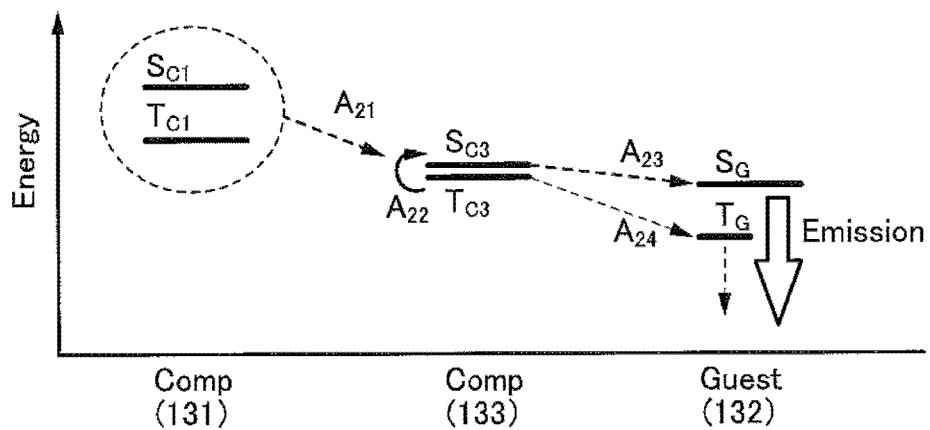

This structure example shows the light-emitting layer 113 in the light-emitting device, which includes the compound 131, the compound 132, and the compound 133. The compound 133 has a function of converting triplet excitation energy into light emission, and the case where a TADF material is used as the compound 133 is described. A fluorescent substance is used as the compound 132 serving as the light-emitting substance (guest material). It is preferable that a compound of one embodiment of the present invention be used as the compound 132 that is a fluorescent substance. FIG. 5B shows an example of the correlation of energy levels in the light-emitting layer 113 in this structure example. Note that terms and numerals in FIG. 5B are similar to those in FIG. 5A and the other terms and numerals are as follows:

$S_{C3}$: the S1 level of the compound 133.

In this structure example, carrier recombination occurs mainly in the compound 131, whereby singlet excitons and triplet excitons are generated. When a TADF material having a relation $S_{C3} \leq S_{C1}$ and $T_{C3} \leq T_{C1}$ is selected as the compound 133, singlet excitation energy and triplet excitation energy generated in the compound 131 can be transferred to the $S_{C3}$ and $T_{C3}$ levels of the compound 133 (Route $A_{21}$ in FIG. 5B). Some of the carriers can be recombined also in the compound 133.

Since the compound 133 is the TADF material, the compound 133 has a function of converting triplet excitation energy into singlet excitation energy by upconversion (Route $A_{22}$ in FIG. 5B). Accordingly, the singlet excitation energy of the compound 133 can be rapidly transferred to the compound 132 (Route $A_{23}$ in FIG. 5B). At this time, $S_{C3} \geq S_G$ is preferably satisfied. Specifically, $S_{C3} \geq S_G$ is preferably satisfied when $S_{C3}$ is energy with a wavelength of the line obtained by extrapolating a tangent to the fluorescent spectrum of the compound 133 at a tail on the short wavelength side, and $S_G$ is energy with a wavelength of the absorption edge of the absorption spectrum of the compound 132.

Therefore, in the light-emitting layer 113 of the light-emitting device in this structure example, triplet excitation energy generated in the compound 133 can be converted into fluorescence of the compound 132 by passing through Route $A_{21}$, Route $A_{22}$, and Route $A_{23}$ in FIG. 5B. In Route $A_{23}$, the compound 133 serves as an energy donor and the compound 132 serves as an energy acceptor. Note that in the light-emitting layer 113 in the light-emitting device of this structure example, the above routes might compete with a route through which the triplet excitation energy of the compound 133 is transferred to the T1 level of the compound 132 (Route $A_{24}$ in FIG. 5B). When such energy transfer (Route $A_{24}$) occurs, the compound 132 that is a fluorescent substance cannot make the triplet excitation energy contribute to light emission, which reduces the emission efficiency of the light-emitting device.

In order to suppress such energy transfer (Route $A_{24}$), as described in the structure example 1, it is important that the distance between the compound 133 and the compound 132, that is, the distance between the compound 133 and the luminophore included in the compound 132 be long.

The compound of one embodiment of the present invention includes a luminophore and a protective group in its structure. In the case where the compound of one embodiment of the present invention serves as the energy acceptor in the light-emitting layer 113, the protective group has a function of lengthening the distance between another energy donor and the luminophore. Thus, in the case where the compound of one embodiment of the present invention is used as the compound 132 in this structure example, the distance between the compound 133 and the compound 132 can be long even when the concentration of the compound 132 is increased; accordingly, the rate of energy transfer by the Förster mechanism can be increased while energy transfer by the Dexter mechanism can be suppressed. With the use of the compound of one embodiment of the present invention as the compound 132, triplet excitation energy transfer (Route $A_{23}$) from the compound 133 to the S1 level ($S_G$) of the compound 132 is likely to occur while triplet excitation energy transfer (Route $A_{24}$: energy transfer by the Dexter mechanism) from the compound 133 to the T1 level ($T_G$) of the compound 132 is less likely to occur. Thus, the emission efficiency of the light-emitting device can be increased while a decrease in emission efficiency due to energy transfer through Route $A_{24}$ can be suppressed. Furthermore, the reliability of the light-emitting device can be improved.

Embodiment 3

In this embodiment, light-emitting devices of embodiments of the present invention will be described.

<Structure Example of Light-Emitting Device>

Figure 6A:
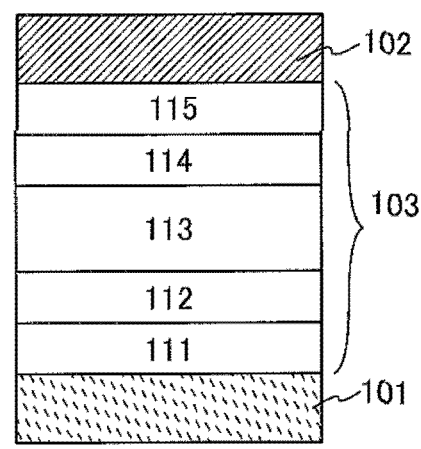
FIGS. 6A and 6B illustrate a structure of a light-emitting device.

FIG. 6A illustrates an example of a light-emitting device including an EL layer that includes a light-emitting layer between a pair of electrodes. Specifically, an EL layer 103 is provided between a first electrode 101 and a second electrode 102. For example, in the case where the first electrode 101 is an anode, the EL layer 103 has a structure in which a hole-injection layer 111, a hole-transport layer 112, a light-emitting layer 113, an electron-transport layer 114, and an electron-injection layer 115 are stacked as functional layers in this order. The light-emitting layer 113 includes a host material and guest materials. A third organic compound 123 is used as the host material, and a first organic compound 121 (fluorescent substance) that has a function of converting singlet excitation energy into light emission and a second organic compound 122 (phosphorescent substance or TADF material) that has a function of converting triplet excitation energy into light emission are used as the guest materials.

Embodiments of the present invention also include light-emitting devices having other structures, such as a light-emitting device that can be driven at low voltage by having a structure (a tandem structure) where a plurality of EL layers are provided between a pair of electrodes and a charge-generation layer is provided between the EL layers, and a light-emitting device having a micro-optical resonator (microcavity) structure between a pair of electrodes and thus having improved optical characteristics. The charge-generation layer has a function of injecting electrons into one of the adjacent EL layers and injecting holes into the other of the EL layers when a voltage is applied between the first electrode 101 and the second electrode 102.

At least one of the first electrode 101 and the second electrode 102 of the light-emitting device is a light-transmitting electrode (e.g., a transparent electrode or a transflective electrode). In the case where the light-transmitting electrode is a transparent electrode, the transparent electrode has a visible light transmittance higher than or equal to 40%. In the case where the light-transmitting electrode is a transflective electrode, the transflective electrode has a visible light reflectance higher than or equal to 20% and lower than or equal to 80%, preferably higher than or equal to 40% and lower than or equal to 70%. These electrodes preferably have a resistivity of $1\times10^{-2}$ Ωcm or less.

Furthermore, when one of the first electrode 101 and the second electrode 102 is a reflective electrode in the light-emitting device of one embodiment of the present invention, the visible light reflectance of the reflective electrode is higher than or equal to 40% and lower than or equal to 100%, preferably higher than or equal to 70% and lower than or equal to 100%. This electrode preferably has a resistivity of $1\times10^{-2}$ Ωcm or less.

First Electrode and Second Electrode

As materials for the first electrode 101 and the second electrode 102, any of the following materials can be used in an appropriate combination as long as the above functions of the electrodes can be fulfilled. For example, a metal, an alloy, an electrically conductive compound, a mixture of these, and the like can be used as appropriate. Specifically, an In—Sn oxide (also referred to as ITO), an In—Si—Sn oxide (also referred to as ITSO), an In—Zn oxide, or an In—W—Zn oxide can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table that is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

For formation of these electrodes, a sputtering method or a vacuum evaporation method can be used.

<Hole-Injection Layer>

The hole-injection layer 111 injects holes from the first electrode 101 serving as an anode to the EL layer 103 and contains an organic acceptor material or a material with a high hole-injection property.

The organic acceptor material allows holes to be generated in another organic compound whose HOMO level is close to the LUMO level of the organic acceptor material when charge separation is caused between the organic acceptor material and the organic compound. Thus, as the organic acceptor material, a compound having an electron-withdrawing group (a halogen group or a cyano group), such as a quinodimethane derivative, a chloranil derivative, and a hexaazatriphenylene derivative, can be used. Examples of the organic acceptor material include 7,7,8,8-tetracyano-2,3,5,6-tetrafluoroquinodimethane (abbreviation: F$_4$-TCNQ), 3,6-difluoro-2,5,7,7,8,8-hexacyanoquinodimethane, chloranil, 2,3,6,7,10,11-hexacyano-1,4,5,8,9,12-hexaazatriphenylene (abbreviation: HAT-CN), and 1,3,4,5,7,8-hexafluorotetracyano-naphthoquinodimethane (abbreviation: F6-TCNNQ). Among organic acceptor materials, HAT-CN, which has a high acceptor property and stable film quality against heat, is particularly favorable. Besides, a [3]radialene derivative, which has a very high electron-accepting property, is preferred; specific examples include α,α',α''-1,2,3-cyclopropanetriylidenetris[4-cyano-2,3,5,6-tetrafluorobenzeneacetonitrile], α,α',α''-1,2,3-cyclopropanetriylidenetris[2,6-dichloro-3,5-difluoro-4-(trifluoromethyl)benzeneacetonitrile], and α,α',α''-1,2,3-cyclopropanetriylidenetris[2,3,4,5,6-pentafluorobenzeneacetonitrile].

Examples of the material having a high hole-injection property are transition metal oxides such as a molybdenum oxide, a vanadium oxide, a ruthenium oxide, a tungsten oxide, and a manganese oxide, Other examples are phthalocyanine-based compounds such as phthalocyanine (abbreviation: H$_2$Pc) and copper phthalocyanine (abbreviation: CuPc), and the like.

Other examples are aromatic amine compounds, which are low molecular compounds, such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N,N-bis(3-methylphenyl)amino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcathazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples are high-molecular compounds (e.g., oligomers, dendrimers, and polymers) such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)

methacrylamide] (abbreviation: PTPDMA), poly[N,N'-bis(4-butylphenyl)-N,N'-bis(phenyl)benzidine] (abbreviation: Poly-TPD), and the like. Alternatively, a high-molecular compound to which acid is added, such as poly(3,4-ethylenedioxythiophene)/poly(styrenesulfonic acid) (abbreviation: PEDOT/PSS) or polyaniline/poly(styrenesulfonic acid) (abbreviation: PAni/PSS), can be used.

Alternatively, as the material having a high hole-injection property, a composite material containing a hole-transport material and an acceptor material (electron-accepting material) can be used. In that case, the acceptor material extracts electrons from a hole-transport material, so that holes are generated in the hole-injection layer 111 and the holes are injected into the light-emitting layer 113 through the hole-transport layer 112. Note that the hole-injection layer 111 may be formed to have a single-layer structure using a composite material containing a hole-transport material and an acceptor material (electron-accepting material), or a layered structure of a layer containing a hole-transport material and a layer containing an acceptor material (electron-accepting material).

The hole-transport material preferably has a hole mobility of greater than or equal to $1 \times 10^{-6}$ cm$^2$/Vs in the case where the square root of the electric field strength [V/cm] is 600. Note that other substances can also be used as long as the substances have a hole-transport property higher than an electron-transport property.

As the hole-transport material, materials having a high hole-transport property, such as a π-electron rich heteroaromatic compound (e.g., a carbazole derivative and a furan derivative) and an aromatic amine (a compound having an aromatic amine skeleton), are preferable.

Examples of the above carbazole derivative (a compound having a carbazole skeleton) include a bicarbazole derivative (e.g., a 3,3'-bicarbazole derivative) and an aromatic amine having a carbazolyl group.

Specific examples of the bicarbazole derivative (e.g., a 3,3'-bicarbazole derivative) are 3,3'-bis(9-phenyl-9H-carbazole) (abbreviation: PCCP), 9,9'-bis(1,1'-biphenyl-4-yl)-3,3'-bi-9H-carbazole, 9,9'-bis(1,1'-biphenyl-3-yl)-3,3'-bi-9H-carbazole, 9-(1,1'-biphenyl-3-yl)-9'-(1,1'-biphenyl-4-yl)-9H,9'H-3,3'-bicarbazole (abbreviation: mBPCCBP), 9-(2-naphthyl)-9'-phenyl-9H,9'H-3,3'-bicarbazole (abbreviation: βNCCP), and the like.

Specific examples of the above aromatic amine having a carbazolyl group include 4-phenyl-4'-(9-phenyl-9H-carbazol-3-yl)triphenylamine (abbreviation: PCBA1BP), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N"-triphenyl-N,N',N"-tris(9-phenylcarbazol-3-ye benzene-1,3,5-triamine (abbreviation: PCA3B), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 2-[N-(9-phenylcarbazol-3-yl)-N-phenylamino]spiro-9,9'-bifluorene (abbreviation: PCASF), N-[4-(9H-carbazol-9-yl)phenyl]-N-(4-phenyl)phenylaniline (abbreviation: YGA1BP), N,N'-bis[4-(carbazol-9-yl)phenyl]-N,N'-diphenyl-9,9-dimethylfluorene-2,7-diamine (abbreviation: YGA2F), and 4,4',4"-tris(carbazol-9-yl)triphenylamine (abbreviation: TCTA).

Other examples of the carbazole derivative include 3-[4-(9-phenanthryl)-phenyl]-9-phenyl-9H-carbazole (abbreviation: PCPPn), 3-[4-(1-naphthyl)-phenyl]-9-phenyl-9H-carbazole (abbreviation: PCPN), 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA).

Specific examples of the above furan derivative (the compound having a furan skeleton) include compounds having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV), 4,4',4"-(benzene-1,3,5-triyl)tri(dibenzofuran) (abbreviation: DBF3P-II), and 4-{3-[3-(9-phenyl-9H-fluoren-9-yl)phenyl]phenyl}dibenzofuran (abbreviation: mmDBFFLBi-II).

Specific examples of the above aromatic amine include 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 2,7-bis[N-(4-diphenylaminophenyl)-N-phenylamino]-spiro-9,9'-bifluorene (abbreviation: DPA2SF), 4,4',4"-tris[N-(1-naphthyl)-N-phenylamino]triphenylamine (abbreviation: 1'-TNATA), 4,4',4"-tris(N,N-diphenylamino)triphenylamine (abbreviation: TDATA), 4,4',4"-tris[N-(3-methylphenyl)-N-phenylamino]triphenylamine (abbreviation: m-MTDATA), N,N'-di(p-tolyl)-N,N-diphenyl-p-phenylenediamine (abbreviation: DTDPPA), 4,4'-bis[N-(4-diphenylaminophenyl)-N-phenylamino]biphenyl (abbreviation: DPAB), 4,4'-bis(N-{4-[N,N-bis(3-methylphenylamino]phenyl}-N-phenylamino)biphenyl (abbreviation: DNTPD), and 1,3,5-tris[N-(4-diphenylaminophenyl)-N-phenylamino]benzene (abbreviation: DPA3B).

As the hole-transport material, a high-molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-AP-phenylamino}phenyl)methacrylamide] (abbreviation:

PTPDMA), or poly[N,N'-bis(4-butylphenyl)-N,N'-bis(phenyl)benzidine] (abbreviation: Poly-TPD) may be used.

Note that the hole-transport material is not limited to the above examples, and any of a variety of known materials may be used alone or in combination as the hole-transport material.

As the acceptor material used for the hole-injection layer 111, an oxide of a metal belonging to any of Group 4 to Group 8 of the periodic table can be used. As specific examples, molybdenum oxide, vanadium oxide, niobium oxide, tantalum oxide, chromium oxide, tungsten oxide, manganese oxide, and rhenium oxide can be given. Among these, molybdenum oxide is especially preferable since it is stable in the air, has a low hygroscopic property, and is easy to handle. It is also possible to use any of the above organic acceptor materials.

The hole-injection layer 111 can be formed by any of known deposition methods such as a vacuum evaporation method.

<Hole-Transport Layer>

The hole-transport layer 112 transports holes injected from the first electrode 101 through the hole-injection layer 111, to the light-emitting layer 113. The hole-transport layer 112 contains a hole-transport material. Thus, the hole-transport layer 112 can be formed using a hole-transport material that can be used for the hole-injection layer 111.

Note that in the light-emitting device of one embodiment of the present invention, the same organic compound as that for the hole-transport layer 112 is preferably used for the light-emitting layer 113. This is because the use of the same organic compounds for the hole-transport layer 112 and the light-emitting layer 113 allows efficient hole transport from the hole-transport layer 112 to the light-emitting layer 113.

<Light-Emitting Layer>

The light-emitting layer 113 contains a light-emitting substance. The light-emitting layer 113 in the light-emitting device of one embodiment of the present invention includes a host material and guest materials. The third organic compound 123 is used as the host material, and the first organic compound 121 (fluorescent substance) that has a function of converting singlet excitation energy into light emission and the second organic compound 122 (phosphorescent substance or TADF material) that has a function of converting triplet excitation energy into light emission are used as the guest materials. Note that a light-emitting substance which can be used in the light-emitting layer 113 is not particularly limited as long as the above condition is satisfied, and a substance whose emission color is blue, violet, bluish violet, green, yellowish green, yellow, orange, red, or the like can be used as appropriate.

Note that two or more kinds of organic compounds may be used as host materials used for the light-emitting layer 113; alternatively, an exciplex formed by these compounds may be used. It is preferable that a substance that has an energy gap larger than that of the first organic compound 121 and that of the second organic compound 122, which are used as the guest material, be used as the third organic compound 123 used as the host material. It is preferable that the lowest singlet excitation energy level (S1 level) of the third organic compound 123 be higher than the S1 level of the first organic compound 121 and that the lowest triplet excitation energy level (T1 level) of the third organic compound 123 be higher than the T1 level of the first organic compound 121. It is preferable that the T1 level of the third organic compound 123 be higher than the T1 level of the second organic compound 122.

An organic compound such as the hole-transport material that can be used in the hole-transport layer 112 or an electron-transport material that can be used in the electron-transport layer 114 described later, or an exciplex formed by two or more kinds of organic compounds can be used as the one or more kinds of organic compounds as long as requirements for the host material used in the light-emitting layer are satisfied. An exciplex whose excited state is formed by two or more kinds of organic compounds has an extremely small difference between the S1 level and the T1 level and functions as a TADF material capable of converting triplet excitation energy into singlet excitation energy. As an example of a combination of the two or more kinds of organic compounds forming an exciplex, it is preferable that one of the two or more kinds of organic compounds have a π-electron deficient heteroaromatic ring and the other have a π-electron rich heteroaromatic ring. A phosphorescent substance such as an iridium-, rhodium-, or platinum-based organometallic complex or a metal complex may be used as one of the combination forming an exciplex.

Note that the first organic compound 121 and the second organic compound 122, which are used as the guest materials of the light-emitting layer 113, preferably exhibit different emission colors. Alternatively, complementary emission colors may be combined to obtain white light emission.

The material described in Embodiment 2 can be used as the first organic compound 121, which is the first guest material of the light-emitting layer 113 and has a function of converting singlet excitation energy into light emission, in the combination satisfying requirements for the guest materials used in the light-emitting layer. Examples of the second organic compound 122, which is the second guest material of the light-emitting layer 113 and has a function of converting triplet excitation energy into light emission, include a substance that emits phosphorescence (phosphorescent material) and a thermally activated delayed fluorescent (TADF) material that exhibits thermally activated delayed fluorescence. Any of these materials can be used similarly in the combination satisfying the requirements for the guest materials used in the light-emitting layer. The lowest singlet excitation energy level (S1 level) of the first organic compound 121 is higher than the T1 level of the second organic compound 122. That is, a peak wavelength in the emission spectrum of light emitted from the second organic compound 122 is longer than that in the emission spectrum of light emitted from the first organic compound 121.

A phosphorescent substance is a compound that emits phosphorescence but does not emit fluorescence at a temperature higher than or equal to a low temperature (e.g., 77 K) and lower than or equal to room temperature (i.e., higher than or equal to 77 K and lower than or equal to 313 K). The phosphorescent substance preferably contains a metal element with large spin-orbit interaction, and can be an organometallic complex, a metal complex (platinum complex), or a rare earth metal complex, for example. Specifically, the phosphorescent substance preferably contains a transition metal element. It is particularly preferable that the phosphorescent substance contain a platinum group element (ruthenium (Ru), rhodium (Rh), palladium (Pd), osmium (Os), iridium (h), or platinum (Pt)), especially iridium, in which case the probability of direct transition between the singlet ground state and the triplet excited state can be increased.

As examples of a phosphorescent material which emits blue or green light and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-κN$^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic complexes in which a phenylpyridine derivative having an electron-withdrawing group is a ligand, such as bis[2-(4',6'-difluorophenyl)pyridinato-N,C$^2$']iridium(III) tetrakis(1-pyrazolyl)borate (abbreviation: FIr6), bis[2-(4',6'-difluorophenyl)pyridinato-N,C$^2$']iridium(III) picolinate (abbreviation: FIrpic), bis{2-[3',5'-bis(trifluoromethyl)phenyl]pyridinato-N,C$^2$'}iridium(III) picolinate (abbreviation: [Ir(CF$_3$ppy)$_2$(pic)]), and bis[2-(4',6'-difluorophenyl)pyridinato-N,C$^2$']iridium(III) acetylacetonate (abbreviation: FIr(acac)) can be given.

As examples of a phosphorescent substance which emits green or yellow light and whose emission spectrum has a peak wavelength at greater than or equal to 495 nm and less than or equal to 590 nm, the following substances can be given.

Examples of the phosphorescent substance include organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-κN$^3$]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazino)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^2$')iridium(III) (abbreviation: [Ir(ppy)$_3$]), bis(2-phenylpyridinato-N,C$^2$')iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^2$')iridium(III) (abbreviation: [Ir(pq)$_3$]), bis(2-phenylquinolinato-N,C$^2$')iridium(III) acetylacetonate (abbreviation: [Ir(pq)$_2$(acac)]), bis[2-(2-pyridinyl-κN)phenyl-κC][2-(4-phenyl-2-pyridinyl-κN)phenyl-κC]iridium(III) (abbreviation: [Ir(ppy)$_2$(4dppy)]), and bis[2-(2-pyridinyl-κN)phenyl-κC][2-(4-methyl-5-phenyl-2-pyridinyl-κN)phenyl-κC]; organometallic complexes such as bis(2,4-diphenyl-1,3-oxazolato-N,C$^2$')iridium(III) acetylacetonate (abbreviation: [Ir(dpo)$_2$(acac)]), bis{2-[4'-(perfluorophenyl)phenyl]pyridinato-N,C$^2$'}iridium(III) acetylacetonate (abbreviation: [Ir(p-PF-ph)$_2$(acac)]), and bis(2-phenylbenzothiazolato-N,C$^2$')iridium(III) acetylacetonate (abbreviation: [Ir(bt)$_2$(acac)]); and a rare earth metal complex such as tris(acetylacetonato)(monophenanthroline)terbium(III) (abbreviation: [Tb(acac)$_3$(Phen)]).

As examples of a phosphorescent substance which emits yellow or red light and whose emission spectrum has a peak wavelength at greater than or equal to 570 nm and less than or equal to 750 nm, the following substances can be given.

Examples include organometallic complexes having a pyrimidine skeleton, such as (diisobuyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and (dipivaloylmethanato)bis[4,6-di(naphthalen-1-yl)pyrimidinato]iridium(III) (abbreviation: [Ir(d1npm)$_2$(dpm)]); organometallic complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylinethanato)iridium(III) (abbreviation: [Ir(tppr)$_2$(dpm)]), bis{4,6-dimethyl-2-[3-(3,5-dimethylphenyl)-5-phenyl-2-pyrazinyl-κN]phenyl-κC}(2,6-dimethyl-3,5-heptanedionato-κ$^2$O,O')iridium(III) (abbreviation: [Ir(dmdppr-P)$_2$(dibm)]), bis{(4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ$^2$O,O')iridium(III) (abbreviation: [Ir(dmdppr-dmCP)$_2$(dpm)]), bis[2-(5-(2,6-dimethylphenyl)-3-(3,5-dim ethylphenyl)-2-pyrazinyl-κN)-4,6-dimethylphenyl-κC](2,2',6,6'-tetramethyl-3,5-heptanedionato-κ$^2$O,O')iridium(III) (abbreviation: [Ir(dmdppr-dmp)$_2$(dpm)]), (acetylacetonato)bis[2-methyl-3-phenylquinoxalinato-N,C$^2$']iridium(III) (abbreviation: [Ir(mpq)$_2$(acac)]), (acetylacetonato)bis(2,3-diphenylquinoxalinato-N,C$^2$')iridium(III) (abbreviation: [Ir(dpq)$_2$(acac)]), and (acetylacetonato)bis[2,3-bis(4-fluorophenyl)quinoxalinato]iridium(III) (abbreviation: [Ir(Fdpq)$_2$(acac)]); organometallic complexes having a pyridine skeleton, such as tris(1-phenylisoquinolinato-N,C$^2$')iridium(III) (abbreviation: [Ir(piq)$_3$])bis(1-phenylisoquinolinato-N,C$^2$')iridium(III) acetylacetonate (abbreviation: [Ir(piq)$_2$(acac)]), and bis[4,6-dimethyl-2-(2-quinolinyl-κN)phenyl-κC](2,4-pentanedionato-κ$^2$O,O')iridium(III) (abbreviation: [Ir(dmpqn)$_2$(acac)]); a platinum complex such as 2,3,7,8,12,13,17,18-octaethyl-21H,23H-porphyrin platinum(II) (abbreviation: [PtOEP]); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]).

Any of materials described below can be used as the TADF material. The TADF material is a material that has a small difference between its S1 and T1 levels (preferably less than or equal to 0.2 eV), that can up-convert a triplet excited state into a singlet excited state (reverse intersystem crossing) using a little thermal energy, and that efficiently exhibits light emission (fluorescence) from the singlet excited state. The thermally activated delayed fluorescence is efficiently obtained under the condition where the difference in energy between the triplet excited energy level and the singlet excited energy level is greater than or equal to 0 eV and less than or equal to 0.2 eV, preferably greater than or equal to 0 eV and less than or equal to 0.1 eV. Note that delayed fluorescence by the TADF material refers to light emission having the same spectrum as normal fluorescence and an extremely long lifetime. The lifetime is $1\times10^{-6}$ seconds or longer, preferably $1\times10^{-3}$ seconds or longer.

Examples of the TADF material include fullerene, a derivative thereof, an acridine derivative such as proflavine, and eosin. Other examples include a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: $SnF_2$(Proto IX)), a mesoporphyrin-tin fluoride complex (abbreviation: $SnF_2$(Meso IX)), a hematoporphyrin-tin fluoride complex (abbreviation: $SnF_2$(Hemato IX)), a coproporphyrin tetramethyl ester-tin fluoride complex (abbreviation: $SnF_2$(Copro III-4Me)), an octaethylporphyrin-tin fluoride complex (abbreviation: $SnF_2$(OEP)), an etioporphyrin-tin fluoride complex (abbreviation: $SnF_2$(Etio I)), and an octaethylporphyrin-platinum chloride complex (abbreviation: $PtCl_2OEP$).

[Chemical Formulae 26]

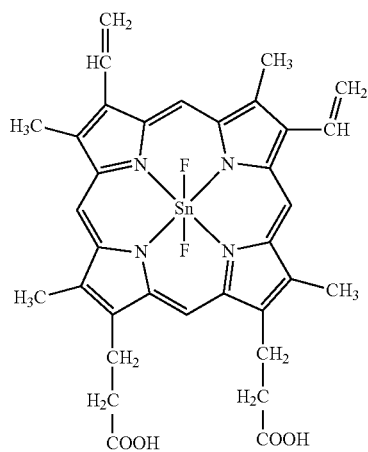

SnF$_2$(Proto IX)

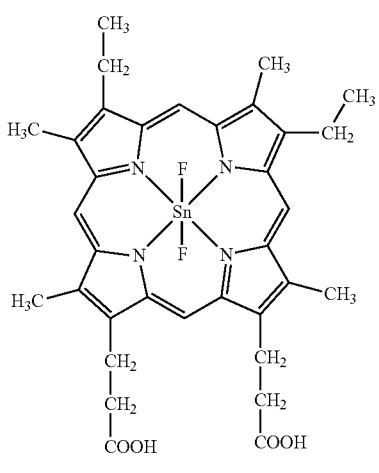

SnF$_2$(Meso IX)

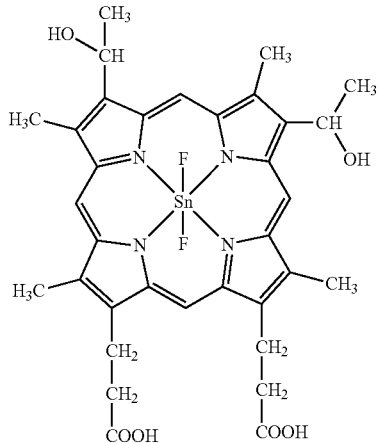

SnF$_2$(Hemato IX)

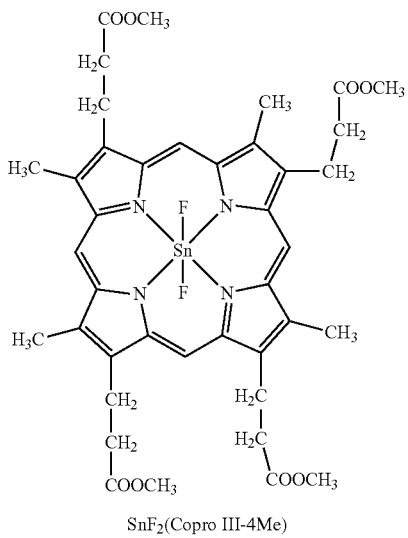

SnF$_2$(Copro III-4Me)

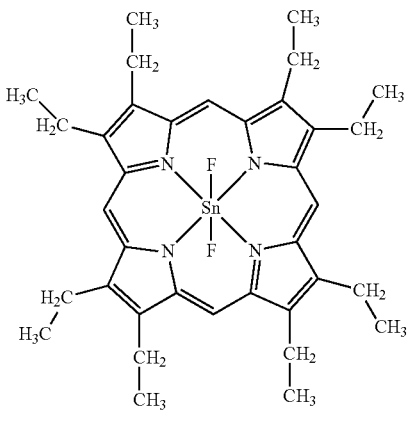

SnF$_2$(OEP)

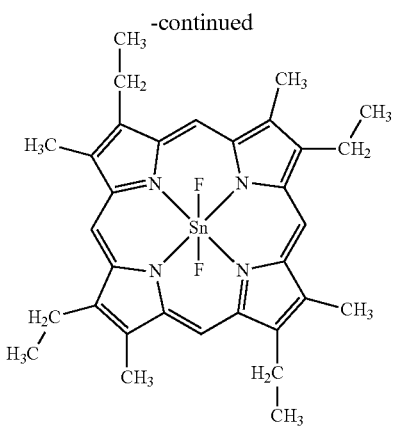

SnF₂(Etio I)

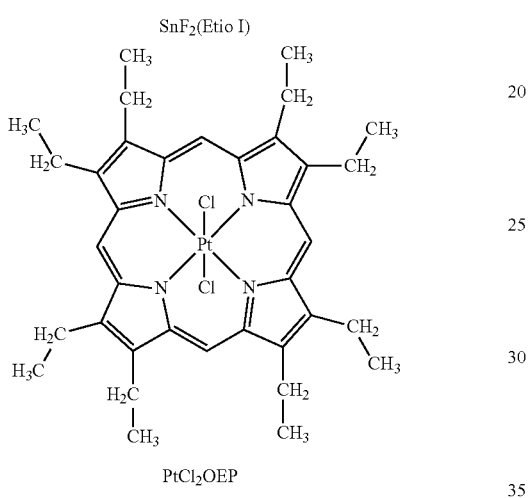

PtCl₂OEP

Alternatively, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), 10-phenyl-10H,10'H-spiro[acridin-9,9'-anthracen]-10'-one (abbreviation: ACRSA), 4-(9'-phenyl-3,3'-bi-9H-carbazol-9-yl)benzofuro[3,2-d]pyrimidine (abbreviation: 4PCCzBfpm), 4-[4-(9'-phenyl-3,3'-bi-9H-carbazol-9-yl)phenyl]benzofuro[3,2-d]pyrimidine (abbreviation: 4PCCzPBfpm), or 9-[3-(4,6-diphenyl-1,3,5-triazin-2-yl)phenyl]-9'-phenyl-2,3'-bi-9H-carbazole (abbreviation: mPCCzPTzn-02) may be used.

Note that a substance in which a π-electron rich heteroaromatic ring is directly bonded to a π-electron deficient heteroaromatic ring is particularly preferable because both the donor property of the π-electron rich heteroaromatic ring and the acceptor property of the π-electron deficient heteroaromatic ring are improved and the energy difference between the singlet excited state and the triplet excited state becomes small.

[Chemical Formula 27]

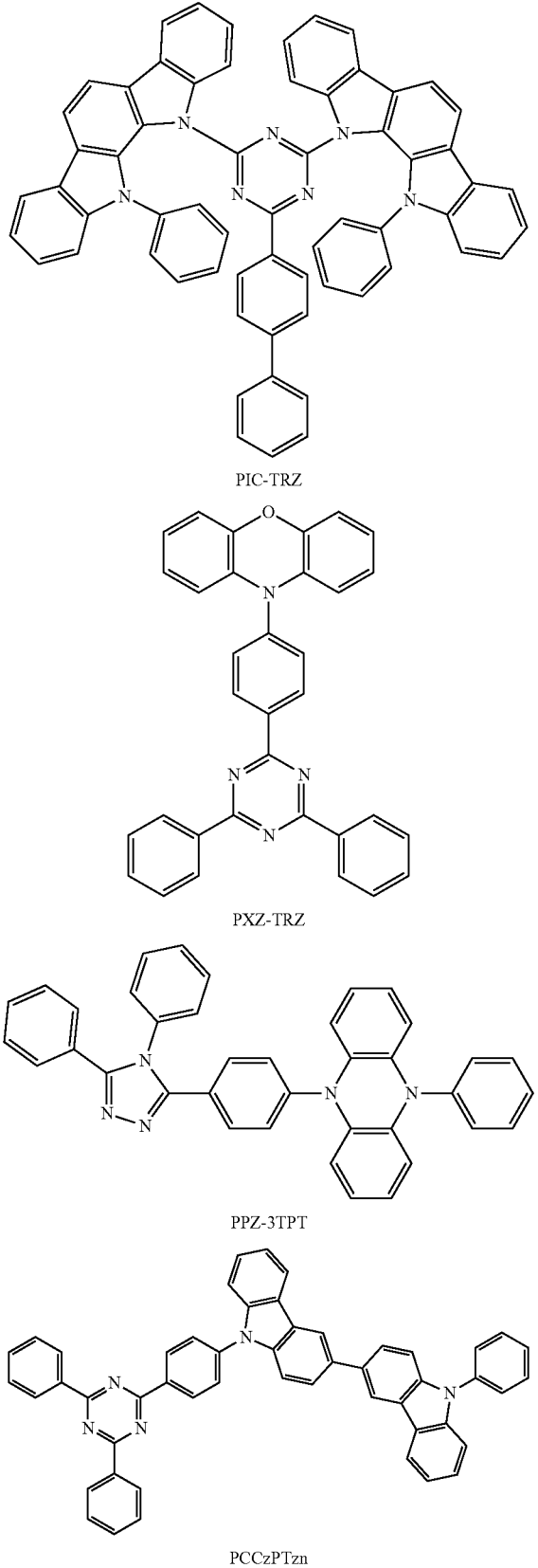

PIC-TRZ

PXZ-TRZ

PPZ-3TPT

PCCzPTzn

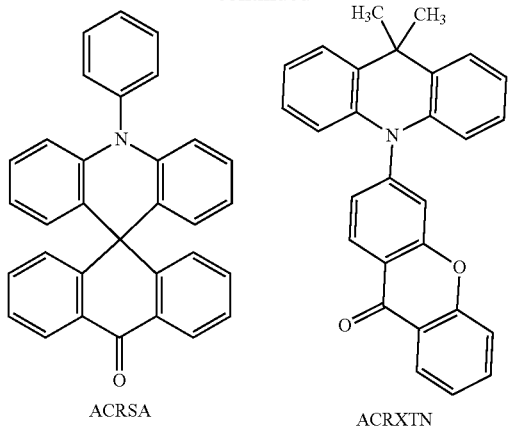

ACRSA

ACRXTN

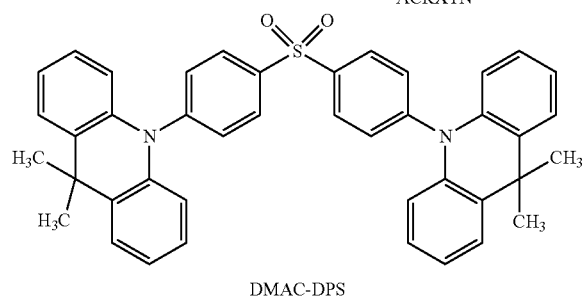

DMAC-DPS

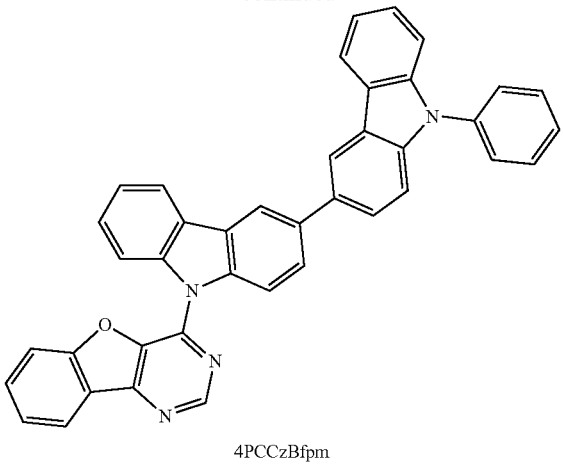 [SMILES: c1ccc(-n2c3ccccc3c3cc(-c4ccc5c(c4)c4ccccc4n5-c4ncnc5c4oc4ccccc45)ccc32)cc1]

4PCCzBfpm

Other than the above-described substances, a nano-structure of a transition metal compound having a perovskite structure can be given as au example of the second organic compound 122, which is a material having a function of converting triplet excitation energy into light emission. In particular, a nano-structure of a metal-halide perovskite material is preferable. The nano-structure is preferably a nanoparticle or a nanorod.

Other than the above-described substances, the following substances which emit fluorescence (fluorescent substances) can be given as examples of the light-emitting substance converting singlet excitation energy into light emission, which can be used as the light-emitting layer 113: a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of pyrene derivatives include N,N'-bis(3-methylphenyl)-N,N'-bis[3-(9-phenyl-9H-flu oren-9-yl)phenyl]pyrene-1,6-diamine (abbreviation: 1,6mMemFLPAPrn), N,N'-diphenyl-N,N'-bis[4-(9-phenyl-9H-fluoren-9-yl)phenyl]pyrene-1,6-diamine (abbreviation: 1,6FLPAPrn), N,N-bis(dibenzofuran-2-yl)-N,N'-diphenylpyrene-1,6-diamine (abbreviation: 1,6FrAPrn), N,N'-bis(dibenzothiophen-2-yl)-N,N'-diphenylpyrene-1,6-diamine (abbreviation: 1,6ThAPrn), N,N'-(pyrene-1,6-diyl)bis([N-phenylbenzo[b]naphtho[1,2-d] furan)-6-amine] (abbreviation: 1,6BnfAPrn), N,N'-(pyrene-1,6-diyl)bis[(N-phenylbenzo[b]naphtho[1,2-d]furan)-8-amine] (abbreviation: 1,6BnfAPrn-02), and N,N'-(pyrene-1,6-diyl)bis[(6,N-diphenylbenzo[b]naphtho[1,2-d]furan)-8-amine] (abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-antbryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10- phenyl-9-anthryl)phenyl]-4'-(9-phenyl-9H-carbazol-3-yl)triphenylamine (abbreviation: PCBAPBA), perylene, 2,5,8,11-tetra(tert-butyl)perylene (abbreviation: TBP), N,N'-(2-cert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), or the like.

Examples of the third organic compound 123, which is the host material of the light-emitting layer 113, include condensed polycyclic aromatic compounds such as an anthracene derivative, a tetracene derivative, a phenanthrene derivative, a pyrene derivative, a chrysene derivative, and a dibenzo[g,p]chrysene derivative.

Specific examples of the above compound include 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), 3-[4-(1-naphthyl)-phenyl]-9-phenyl-9H-carbazole (abbreviation: PCPN), 9,10-diphenylanthracene (abbreviation: DPAnth), N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 6,12-dimethoxy-5,11-diphenylchrysene, N,N,N',N',N'',N'',N''',N'''-octaphenyldibenzo[g,p]chrysene-2,7,10,15-tetraamine (abbreviation: DBC1), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthy)anthracene (abbreviation: t-BuDNA), 9,9'-bianthryl (abbreviation: BANT), 9,9'-(stilbene-3,3'-diyOdiphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), 5,12-diphenyltetracene, and 5,12-bis(biphenyl-2-yl)tetracene.

Other than the above-described examples, an aromatic amine, a carbazole derivative, a dibenzothiophene derivative, a dibenzofuran derivative, a zinc- or aluminum-based metal complex, an oxadiazole derivative, a triazole derivative, a benzimidazole derivative, a quinoxaline derivative, a dibenzoquinoxaline derivative, a pyrimidine derivative, a pyrazine derivative, a triazine derivative, a pyridine derivative, a bipyridine derivative, a phenanthroline derivative, or the like can be used as the third organic compound 123, which is the host material of the light-emitting layer 113.

Specific examples thereof include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), triazole derivatives such as 3-(4-biphenylyl)-4-phenyl-5-(4-tert-butylphenyl)-1,2,4-triazole (abbreviation: TAZ) and 3-(4-tert-butylphenyl)-4-(4-ethylphenyl)-5-(4-biphenylyl)-1,2,4-triazole (abbreviation: p-EtTAZ), 2,2',2''-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), 4,4'-bis(5-methylbenzoxazol-2-yl)stilbene (abbreviation: BzOS), bathophenanthroline (abbreviation: Bphen), bathocuproine (abbreviation: BCP), 2,9-bis(naphthalen-2-yl)-4,7-diphenyl-1,10-phenanthroline (abbreviation: NBphen), and quinoxaline derivatives and dibenzoquinoxaline derivatives, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[a]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Other examples include pyrimidine derivatives such as 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 9,9'-(pyrimidine-4,6-diyldi-3,1-phenylene)bis(9H-carbazole) (abbreviation: 4,6mCzP2Pm), triazine derivatives such as 2-{4-[3-(N-phenyl-9H-carbazol-3-yl)-9H-carbazol-9-yl]phenyl}-4,6-diphenyl-1,3,5-triazine (abbreviation: PCCzPTzn) and 9-[3-(4,6-diphenyl-1,3,5-triazin-2-yl)phenyl]-9'-phenyl-2,3'-bi-9H-carbazole (abbreviation: mPCCzPTzn-02), and pyridine derivatives such as 3,5-bis[3-(9H-carbazol-9-yl)phenyl]pyridine (abbreviation: 35DCzPPy) and 1,3,5-tri[3-(3-pyridyephenyl]benzene (abbreviation: TmPyPB).

Further alternatively, a high-molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioetylfluorene-2,7-diyl)-co-(2,2'-bipyridine-6,6-diyl)] (abbreviation: PF-BPy) can be used.

<Electron-Transport Layer>

The electron-transport layer 114 transports electrons injected from the second electrode 102 through the electron-injection layer 115, to the light-emitting layer 113. Note that the electron-transport layer 114 contains an electron-transport material. It is preferable that the electron-transport material contained in the electron-transport layer 114 be a substance with an electron mobility of higher than or equal to $1 \times 10^{-6}$ cm$^2$/Vs in the case where the square root of the electric field strength [V/cm] is 600. Note that any other substance can also be used as long as the substance transports electrons more easily than it transports holes. The electron-transport layers 114, 114a, and 114b each function even with a single-layer structure; however, when the electron-transport layer 114 has a stacked layer structure including two or more layers as needed, the device characteristics can be improved.

Examples of an organic compound that can be used for the electron-transport layer 114 include materials having a high electron-transport property (electron-transport materials), such as an organic compound having a structure where an aromatic ring is fused to a furan ring of a furodiazine skeleton, a metal complex having a quinoline skeleton, a metal complex having a benzoquinoline skeleton, a metal complex having an oxazole skeleton, a metal complex having a thiazole skeleton, an oxadiazole derivative, a triazole derivative, an imidazole derivative, an oxazole derivative, a thiazole derivative, a phenanthroline derivative, a quinoline derivative having a quinoline ligand, a benzoquinoline derivative, a quinoxaline derivative, a dibenzoquinoxaline derivative, a pyridine derivative, a bipyridine derivative, a pyrimidine derivative, and a π-electron deficient heteroaromatic compound (e.g., a nitrogen-containing heteroaromatic compound).

Specific examples of the electron-transport material include metal complexes having a quinoline skeleton or a benzoquinoline skeleton, such as 2-[3'-(dibenzothiophen-4-yl)biphenyl-3-yl]dibenzo[f,h]quinoxaline (abbreviation: 2mDBTBPDBq-II), 2-[3'-(dibenzothiophen-4-yl)biphenyl-3-yl]dibenzo[f,h]quinoxaline (abbreviation: 2mDBTBPDBq-II), 5-[3-(4,6-diphenyl-1,3,5-triazin-2-yl)phenyl]-7,7-dimethyl-5H,7H-indeno[2,1-b]carbazole (abbreviation: mINc(II)PTzn), 4-[3-(dibenzothiophen-4-yl)phenyl]-8-(naphthalen-2-yl)-[1]benzofuro[3,2-d]pyrimidine (abbreviation: 8βN-4mDBtPBfpm), 3,8-bis[3-(dibenzothiophen-4-yl)phenyl]benzofuro[2,3-b]pyrazine (abbreviation: 3,8mDBtP2Bfpr), 4,8-bis[3-(dibenzothiophen-4-yl)phenyl]-[I]benzofuro[3,2-d]pyrimidine (abbreviation: 4,8mDBtP2Bfpm), 9-[(3'-dibenzothiophen-4-yl)biphenyl-3-yl]naphtho[1',2':4,5]furo[2,3-b]pyrazine (abbreviation: 9mDBtBPNfpr), 8-[3'-(dibenzothiophen-4-yl) (1,1'-biphenyl-3-yl)]naphtho[1',2':4,5]furo[3,2-d]pyrimidine (abbreviation: 8mDBtBPNfpm), 8-[(2,2'-binaphthalen)-6-yl]-4-[3-(dibenzothiophen-4-yl)phenyl-[1]benzofuro[3,2-d]pyrimidine (abbreviation: 8(βN2)-4mDBtPBfpm), tris(8-quinolinolato)aluminum(III) (abbreviation: Alq$_3$), tris(4-methyl-8-quinolinolato)aluminum (abbreviation: Almq$_3$), bis(10-hydroxybenzo[h]quinolinato)beryllium (abbreviation: BeBq$_2$), bis(2-methyl-8-quinolinolato)(4-phenylphenolato)aluminum(III) (abbreviation: BAlq), and bis(8-quinolinolato)zinc(II) (abbreviation: Znq), and metal complexes having an oxazole skeleton or a thiazole skeleton, such as bis[2-(2-benzoxazolyl)phenolato]zinc(II) (abbreviation: ZnPBO), and bis[2-(2-benzothiazolyl)phenolato]zinc(II) (abbreviation: ZnBTZ).

Other than the metal complexes, it is possible to use oxadiazole derivatives such as PBD, OXD-7, and CO11, triazole derivatives such as TAZ and p-EtFAZ, imidazole derivatives (including benzimidazole derivatives) such as TPBI and inDBTBIm-II, an oxazole derivative such as BzOs, phenanthroline derivatives such as Bphen, BCP, and NBphen, quinoxaline derivatives and dibenzoquinoxaline derivatives, such as 2mDBTPDBg-II, 2mDBTBPDBq-II, 2mCzBPDBq, 2CzPDBq-III, 7mDBTPDBq-II, and 6mDBTPDBq-II, pyridine derivatives such as 35DCzPPy and TmPyPB, pyrimidine derivatives such as 4,6mPnP2Pm, 4,6mDBTP2Pm-II, and 4,6mCzP2Pm, and triazine derivatives such as PCCzPTzn and mPCCzPTzn-02.

It is also possible to use high-molecular compounds such as PPy, PF-Py, and PF-BPy.

<Electron-Injection Layer>

The electron-injection layer 115 is a layer for increasing the efficiency of electron injection from the second electrode (cathode) 102 and is preferably formed using a material whose value of the LUMO level has a small difference (0.5 eV or less) from the work function of a material of the second electrode (cathode) 102. Thus, the electron-injection layer 115 can be formed using an alkali metal, an alkaline earth metal, or a compound thereof, such as lithium, cesium, lithium fluoride (LiF), cesium fluoride (CsF), calcium fluoride (CaF$_2$), 8-(quinolinolato)-lithium (abbreviation: Liq), 2-(2-pyridyl)phenolatolithium (abbreviation: LiPP), 2-(2-pyridyl)-3-pyridinolato lithium (abbreviation: LiPPy), 4-phenyl-2-(2-pyridyl)phenolato lithium (abbreviation: LiPPP), lithium oxide (LiO$_x$), or cesium carbonate. A rare earth metal compound like erbium fluoride (ErF$_3$) can also be used.

Figure 6B:
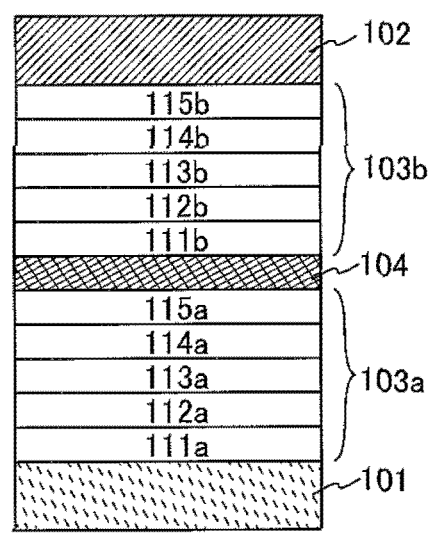

When a charge-generation layer 104 is provided between two EL layers (103a and 103b) as in the light-emitting device in FIG. 6B, a structure in which a plurality of EL layers are stacked between the pair of electrodes (the structure is also referred to as a tandem structure) can be obtained. Note that in this embodiment, functions and materials of the hole-injection layer 111, the hole-transport layer 112, the light-emitting layer 113, the electron-transport layer 114, and the electron-injection layer 115 that are illustrated in FIG. 6A are the same as those of hole-injection layers 111a and 111b, hole-transport layers 112a and 112b, light-emitting layers 113a and 113b, electron-transport layers 114a and 114b, and electron-injection layers 115a and 115b that are illustrated in FIG. 6B.

<Charge-Generation Layer>

In the light-emitting device in FIG. 6B, the charge-generation layer 104 has a function of injecting electrons into the EL layer 103a and injecting holes into the EL layer 103b when a voltage is applied between the first electrode (anode) 101 and the second electrode (cathode) 102. The charge-generation layer 104 may have either a structure in which an electron acceptor (acceptor) is added to a hole-transport material or a structure in which an electron donor (donor) is added to an electron-transport material. Alternatively, both of these layers may be stacked. Note that forming the charge-generation layer 104 with the use of any of the above materials can inhibit an increase in driving voltage caused by the stack of the EL layers.

In the case where the charge-generation layer 104 has a structure in which an electron acceptor is added to a hole-transport material, any of the materials described in this embodiment can be used as the hole-transport material. As the electron acceptor, it is possible to use 7,7,8,8-tetracyano-2,3,5,6-tetrafluoroquinodimethane (abbreviation: F$_4$-TCNQ), chloranil, and the like. Other examples include oxides of metals that belong to Group 4 to Group 8 of the periodic table. Specific examples are vanadium oxide, niobium oxide, tantalum oxide, chromium oxide, molybdenum oxide, tungsten oxide, manganese oxide, and rhenium oxide.

In the case where the charge-generation layer 104 has a structure in which an electron donor is added to an electron-transport material, any of the materials described in this embodiment can be used as the electron-transport material. As the electron donor, it is possible to use an alkali metal, an alkaline earth metal, a rare earth metal, metals that belong to Group 2 and Group 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may be used as the electron donor.

Although FIG. GB illustrates the structure in which two EL layers 103 are stacked, three or more EL layers may be stacked with charge-generation layers each provided between two adjacent EL layers.

<Substrate>

The light-emitting device described in this embodiment can be formed over any of a variety of substrates. Note that the type of substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film.

Examples of the glass substrate include a barium borosilicate glass substrate, an aluminoborosilicate glass substrate, and a soda lime glass substrate. Examples of the flexible substrate, the attachment film, and the base material film include plastics typified by polyethylene terephthalate (PET), polyethylene naphthalate (PEN), and polyether sulfone (FES); a synthetic resin such as an acrylic resin; polypropylene; polyester; polyvinyl fluoride; polyvinyl chloride; polyamide; polyimide; an aramid resin; an epoxy resin; an inorganic vapor deposition film; and paper.

For fabrication of the light-emitting device in this embodiment, a vacuum process such as an evaporation method or a solution process such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers included in the EL layers (the hole-injection layers 111, 111a, and 111b, the hole-transport layers 112, 112a, and 112b, the light-emitting layers 113, 113; and 113b, the electron-transport layers 114, 114a, and 114b, and the electron-injection layers 115, 115a, and 115b) and the charge-generation layers 104, 104a, and 104b of the light-emitting device can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, microcontact printing, or nanoimprint lithography), or the like.

Note that materials that can be used for the functional layers included in the EL layers 103, 103a, and 103b (the hole-injection layers 111, 111a, and 111b, the hole-transport layers 112, 112; and 112b, the light-emitting layers 113, 113a, and 113b, the electron-transport layers 114, 114; and 114b, and the electron-injection layers 115, 115a, and 115b) and the charge-generation layers 104, 104; and 104b of the light-emitting device described in this embodiment are not limited to the above materials, and other materials can be used in combination as long as the functions of the layers are fulfilled. For example, a high-molecular compound (e.g., an oligomer, a dendrimer, and a polymer), a middle molecular compound (a compound between a low molecular compound and a high-molecular compound with a molecular weight of 400 to 4000), or an inorganic compound (e.g., a quantum dot material) can be used. The quantum dot material may be a colloidal quantum dot material, an alloyed quantum dot material, a core-shell quantum dot material, a core quantum dot material, or the like.

The structures described in this embodiment can be used in combination with any of the structures described in the other embodiments, as appropriate.

Embodiment 4

Figure 7A:
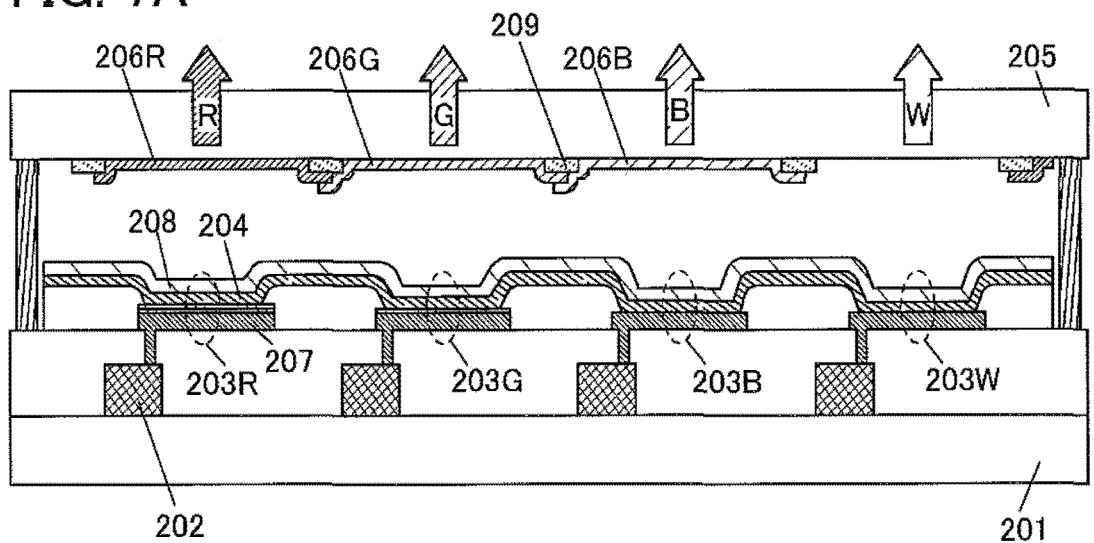
FIGS. 7A to 7C illustrate a light-emitting apparatus.

In this embodiment, a light-emitting apparatus of one embodiment of the present invention will be described. Note that a light-emitting apparatus illustrated in FIG. 7A is an active-matrix light-emitting apparatus in which transistors (FETs) 202 over a first substrate 201 are electrically connected to light-emitting devices (203R, 203G, 203B, and 203W). The light-emitting devices (203R, 203G, 203B, and 203W) include a common EL layer 204 and each have a microcavity structure in which the optical path length between electrodes is adjusted according to a desired emission color of the light-emitting device. The light-emitting apparatus is a top-emission light-emitting apparatus in which light is emitted from the EL layer 204 through color filters (206R, 206G, and 206B) formed on a second substrate 205.

The light-emitting apparatus illustrated in FIG. 7A is fabricated such that a first electrode 207 functions as a reflective electrode and a second electrode 208 functions as a transflective electrode that both transmits and reflects light (visible light or near-infrared light). Note that description in any of the other embodiments can be referred to as appropriate for electrode materials for the first electrode 207 and the second electrode 208.

Figure 7B:
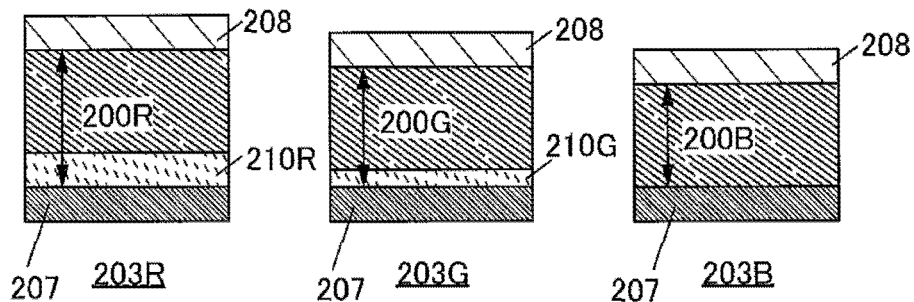

In the case where the light-emitting device 203R functions as a red light-emitting device, the light-emitting device 203G functions as a green light-emitting device, the light-emitting device 203B functions as a blue light-emitting device, and the light-emitting device 203W functions as a white light-emitting device in FIG. 7A, for example, a gap between the first electrode 207 and the second electrode 208 in the light-emitting device 203R is adjusted to have an optical path length 200R, a gap between the first electrode 207 and the second electrode 208 in the light-emitting device 203G is adjusted to have an optical path length 200G, and a gap between the first electrode 207 and the second electrode 208 in the light-emitting device 203B is adjusted to have an optical path length 20013 as illustrated in FIG. 7B. Note that optical adjustment can be performed in such a manner that a conductive layer 210R is stacked over the first electrode 207 in the light-emitting device 203R and a conductive layer 210G is stacked over the first electrode 207 in the light-emitting device 203G as illustrated in FIG. 7B.

The second substrate 205 is provided with the color filters (206R, 206G, and 206B), Note that the color filters each transmit visible light in a specific wavelength range and blocks visible light in a specific wavelength range, Thus, as illustrated in FIG. 7A, the color filter 206R that transmits only light in the red wavelength range is provided in a position overlapping with the light-emitting device 203R, whereby red light emission can be obtained from the light-emitting device 203R. Furthermore, the color filter 206G that transmits only light in the green wavelength range is provided in a position overlapping with the light-emitting device 203G, whereby green light emission can be obtained from the light-emitting device 203G. Moreover, the color filter 2068 that transmits only light in the blue wavelength range is provided in a position overlapping with the light-emitting device 203B, whereby blue light emission can be obtained from the light-emitting device 203B. Note that the light-emitting device 203W can emit white light without a color filter. Note that a black layer (black matrix) 209 may be provided at an end portion of each color filter. The color filters (206R, 206G, and 206B) and the black layer 209 may be covered with an overcoat layer formed using a transparent material.

Figure 7C:
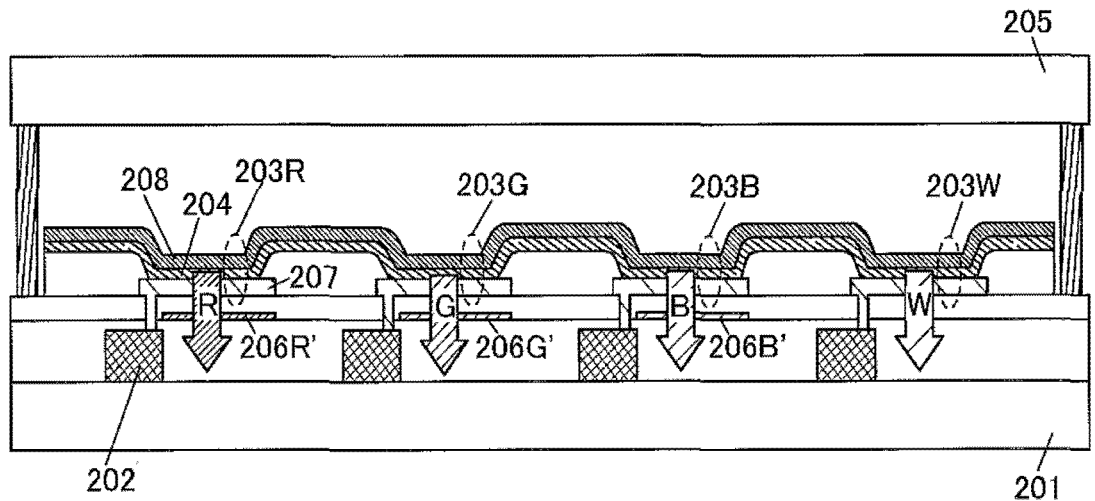

Although the light-emitting apparatus in FIG. 7A has a structure hi which light is extracted from the second substrate 205 side (top emission structure), a structure in which light is extracted from the first substrate 201 side where the FETs 202 are formed (bottom emission structure) may be employed as illustrated in FIG. 7C. In the case of a bottom-emission light-emitting apparatus, the first electrode 207 is formed as a transflective electrode and the second electrode 208 is formed as a reflective electrode. As the first substrate 201, a substrate having at least a light-transmitting property is used. As illustrated in FIG. 7C, color filters (206R', 206G', and 206B') are provided closer to the first substrate 201 than the light-emitting devices (203R, 203G, and 203B) are.

In FIG. 7A, the light-emitting devices are the red light-emitting device, the green light-emitting device, the blue light-emitting device, and the white light-emitting device; however, the light-emitting devices of one embodiment of the present invention are not limited to the above, and a yellow light-emitting device or an orange light-emitting device may be used. Note that description in any of the other embodiments can be referred to as appropriate for materials that are used for the EL layers (a light-emitting layer, a hole-injection layer, a hole-transport layer, an electron-transport layer, an electron-injection layer, a charge-generation layer, and the like) to fabricate each of the light-emitting devices. In that case, a color filter needs to be appropriately selected according to the emission color of the light-emitting device.

With the above structure, a light-emitting apparatus including light-emitting devices that exhibit a plurality of emission colors can be fabricated.

The structures described in this embodiment can be used in combination with any of the structures described in the other embodiments, as appropriate.

Embodiment 5

In this embodiment, a light-emitting apparatus of one embodiment of the present invention will be described.

The use of the device structure of the light-emitting device of one embodiment of the present invention allows fabrication of an active-matrix light-emitting apparatus or a passive-matrix light-emitting apparatus. Note that an active-matrix light-emitting apparatus has a structure including a combination of a light-emitting device and a transistor (FET). Thus, each of a passive-matrix light-emitting apparatus and an active-matrix light-emitting apparatus is one embodiment of the present invention. Note that any of the light-emitting devices described in other embodiments can be used in the light-emitting apparatus described in this embodiment.

In this embodiment, an active-matrix light-emitting apparatus will be described with reference to FIGS. 8A and 8B.

Figure 8A:
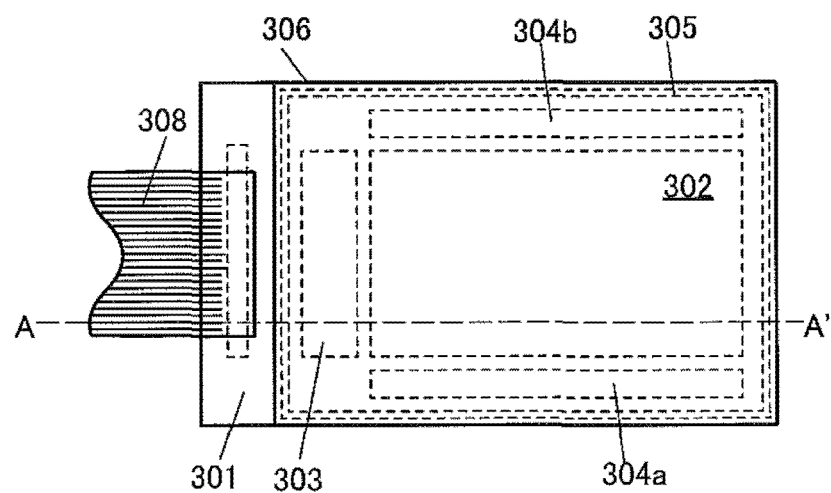
FIG. 8A is a top view illustrating a light-emitting apparatus.
Figure 8B:
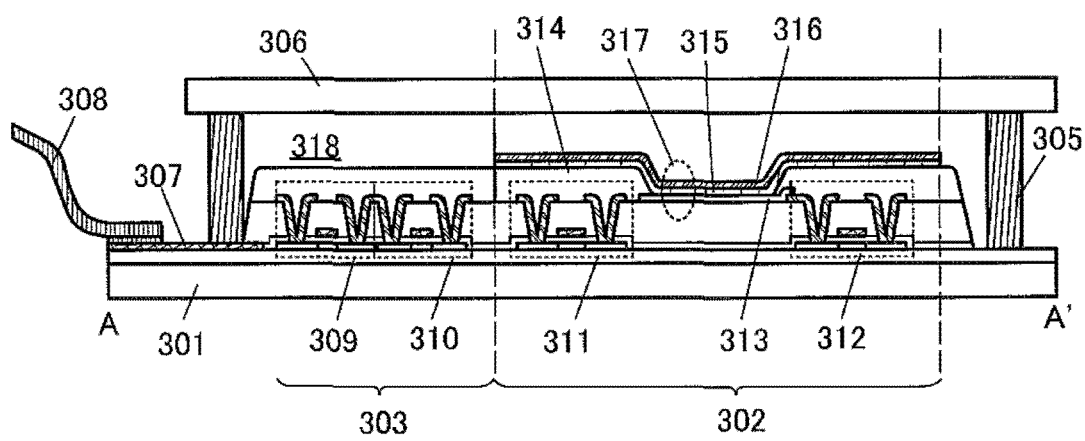
FIG. 8B is a cross-sectional view illustrating the light-emitting apparatus.

FIG. 8A is a top view illustrating the light-emitting apparatus, and FIG. 8B is a cross-sectional view taken along chain line A-A' in FIG. 8A, The active-matrix light-emitting apparatus includes a pixel portion 302, a driver circuit portion (source line driver circuit) 303, and driver circuit portions (gate line driver circuits) (304a and 304b) that are provided over a first substrate 301, The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is electrically connected to an FPC 308 that is an external input terminal. Note that the FPC 308 transmits a signal (e.g., a video signal, a clock signal, a start signal, or a reset signal) or a potential from the outside to the driver circuit portions (303, 304a, and 304b). The FPC 308 may be provided with a printed wiring board (PWB). Note that the light-emitting apparatus provided with an FPC or a PWB is included in the category of a light-emitting apparatus.

FIG. 8B illustrates a cross-sectional structure of the light-emitting apparatus.

The pixel portion 302 includes a plurality of pixels each of which includes an FET (switching FET) 311, an FET (current control FET) 312, and a first electrode 313 electrically connected to the FET 312. Note that the number of FETs included in each pixel is not particularly limited and can be set appropriately.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. A semiconductor having crystallinity is preferably used, in which case deterioration of the transistor characteristics can be inhibited.

For the semiconductor, a Group 14 element, a compound semiconductor, an oxide semiconductor, an organic semiconductor, or the like can be used, for example. As a typical example, a semiconductor containing silicon, a semiconductor containing gallium arsenide, or an oxide semiconductor containing indium can be used.

The driver circuit portion 303 includes the FET 309 and the FET 310. The driver circuit portion 303 may be formed with a circuit including transistors having the same conductivity type (either n-channel transistors or p-channel transistors) or a CMOS circuit including an n-channel transistor and a p-channel transistor. Furthermore, a driver circuit may be provided outside.

An end portion of the first electrode 313 is covered with an insulator 314. The insulator 314 can be formed using an organic compound such as a negative photosensitive resin or a positive photosensitive resin (acrylic resin), or an inorganic compound such as silicon oxide, silicon oxynitride, or silicon nitride. The insulator 314 preferably has a curved surface with curvature at an upper end portion or a lower end portion thereof. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the components of a light-emitting device 317 described in this embodiment. Although not illustrated, the second electrode 316 is electrically connected to the FPC 308 that is an external input terminal.

Although the cross-sectional view in FIG. 8B illustrates only one light-emitting device 317, a plurality of light-emitting devices are arranged in a matrix in the pixel portion 302. Light-emitting devices that emit light of three kinds of colors (R, G, and B) are selectively formed in the pixel portion 302, whereby a light-emitting apparatus capable of displaying a full-color image can be obtained. In addition to the light-emitting devices that emit light of three kinds of colors (R, G, and B), for example, light-emitting devices that emit light of white (W), yellow (Y), magenta (M), cyan (C), and the like may be formed. For example, the light-emitting devices that emit light of some of the above colors are used in combination with the light-emitting devices that emit light of three kinds of colors (R, G, and B), whereby effects such as an improvement in color purity and a reduction in power consumption can be achieved. Alternatively, a light-emitting apparatus which is capable of displaying a full-color image may be fabricated by a combination with color filters. As color filters, red (R), green (G), blue (B), cyan (C), magenta (M), and yellow (Y) color filters and the like can be used.

When the second substrate 306 and the first substrate 301 are bonded to each other with the sealant 305, the FETs (309, 310, 311, and 312) and the light-emitting device 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy resin, glass frit, or the like can be used for the sealant 305. It is preferable to use a material that is permeable to as little moisture and oxygen as possible for the sealant 305. As the second substrate 306, a substrate that can be used as the first substrate 301 can be similarly used. Thus, any of the various substrates described in the other embodiments can be appropriately used. As the substrate, a glass substrate, a quartz substrate, or a plastic substrate made of fiber-reinforced plastic (FRP), polyvinyl fluoride (PVF), polyester, an acrylic resin, or the like can be used. In the case where glass flit is used for the sealant, the first substrate 301 and the second substrate 306 are preferably glass substrates in terms of adhesion.

Accordingly, the active-matrix light-emitting apparatus can be obtained.

In the case where the active-matrix light-emitting apparatus is provided over a flexible substrate, the FETs and the light-emitting device may be directly formed over the flexible substrate; alternatively, the FETs and the light-emitting device may be formed over a substrate provided with a separation layer and then separated at the separation layer by application of heat, force, laser, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (silk, cotton, or hemp), a synthetic fiber (nylon, polyurethane, or polyester), a regenerated fiber (acetate, cupro, rayon, or regenerated polyester), or the like), a leather substrate, and a rubber substrate. With the use of any of these substrates, an increase in durability, an increase in heat resistance, a reduction in weight, and a reduction in thickness can be achieved.

The light-emitting device included in the active-matrix light-emitting apparatus may emit pulsed light (with a frequency of kHz or MHz, for example) so that the light is used for display. The light-emitting device formed using any of the above organic compounds has excellent frequency characteristics; therefore, time for driving the light-emitting device can be shortened, resulting in a reduction in power consumption. Furthermore, a reduction in driving time leads to inhibition of heat generation, so that the degree of deterioration of the light-emitting device can be reduced.

The structures described in this embodiment can be used in combination with any of the structures described in the other embodiments, as appropriate.

Embodiment 6

In this embodiment, examples of a variety of electronic devices and an automobile manufactured using the light-emitting device of one embodiment of the present invention or a light-emitting apparatus including the light-emitting device of one embodiment of the present invention will be described. Note that the light-emitting apparatus can be used mainly in a display portion of the electronic device described in this embodiment.

Electronic devices illustrated in FIGS. 9A to 9E can include a housing 7000, a display portion 7001, a speaker 7003, an LED lamp 7004, operation keys 7005 (including a power switch or an operation switch), a connection terminal 7006, a sensor 7007 (a sensor having a function of measuring force, displacement, position, speed, acceleration, angular velocity, rotational frequency, distance, light, liquid, magnetism, temperature, a chemical substance, sound, time, hardness, an electric field, current, voltage, electric power, radiation, flow rate, humidity, gradient, oscillation, odor, or infrared ray), a microphone 7008, and the like.

Figure 9A:
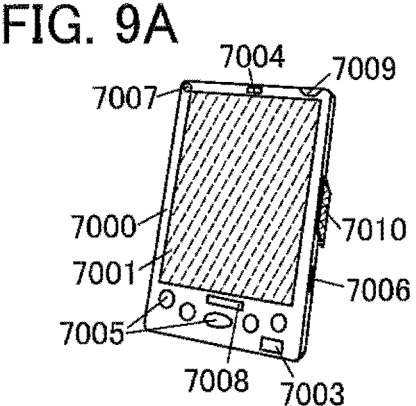
FIG. 9A illustrates a mobile computer.

FIG. 9A illustrates a mobile computer that can include a switch 7009, an infrared port 7010, and the like in addition to the above components.

Figure 9B:
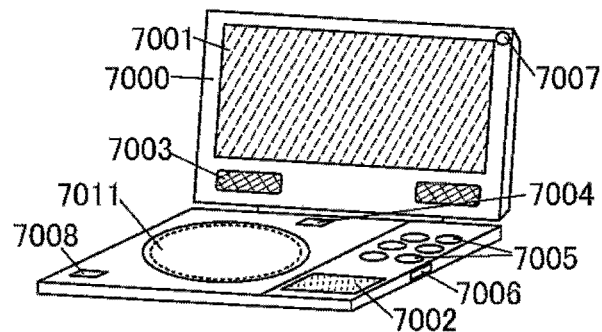
FIG. 9B illustrates a portable image reproducing device.

FIG. 9B illustrates a portable image reproducing device (e.g., a DVD player) that is provided with a recording medium and can include a second display portion 7002, a recording medium reading portion 7011, and the like in addition to the above components.

Figure 9C:
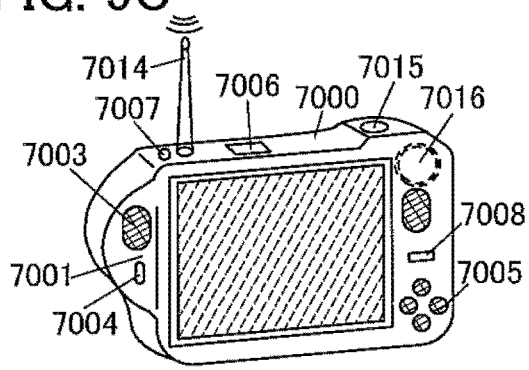
FIG. 9C illustrates a digital camera.

FIG. 9C illustrates a digital camera that has a television reception function and can include an antenna 7014, a shutter button 7015, an image receiving portion 7016, and the like in addition to the above components.

Figure 9D:
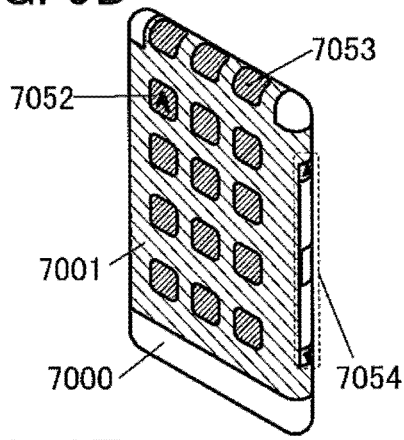
FIGS. 9D and 9E each illustrate a portable information terminal.

FIG. 9D illustrates a portable information terminal. The portable information terminal has a function of displaying information on three or more surfaces of the display portion 7001. Here, information 7052, information 7053, and information 7054 are displayed on different surfaces. For example, a user of the portable information terminal can check the information 7053 displayed such that it can be seen from above the portable information terminal, with the portable information terminal put in a breast pocket of his/her clothes. Thus, the user can see the display without taking out the portable information terminal from the pocket and decide whether to answer the call, for example.

Figure 9E:
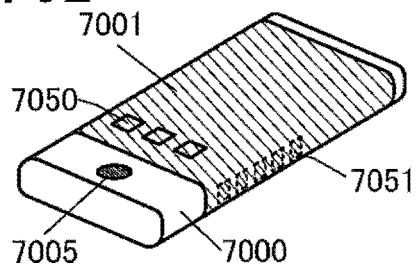

FIG. 9E illustrates a portable information terminal (e.g., a smartphone) and can include the display portion 7001, the operation key 7005, and the like in the housing 7000. Note that the portable information terminal may include a speaker, a connection terminal, a sensor, or the like. The portable information terminal can display text or image data on its plurality of surfaces. Here, three icons 7050 are displayed. Furthermore, information 7051 indicated by dashed rectangles can be displayed on another surface of the display portion 7001. Examples of the information 7051 include notification of reception of an e-mail, an SNS message, an incoming call, or the like, the title and sender of an e-mail, an SNS message, or the like, the date, the time, remaining battery, and the reception strength of an antenna. The icon 7050 or the like may be displayed at the position where the information 7051 is displayed.

Figure 9F:
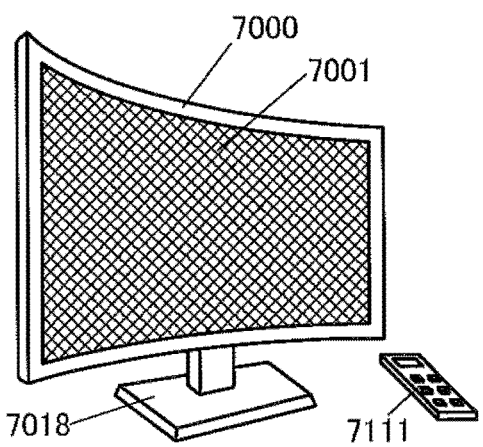
FIG. 9F illustrates a television device.

FIG. 9F illustrates a large-size television set (also referred to as TV or a television receiver) and can include the housing 7000, the display portion 7001, and the like. In addition, here, the housing 7000 is supported by a stand 7018. The television set can be operated with a separate remote controller 7111 or the like. The display portion 7001 may include a touch sensor. The television set can be operated by touching the display portion 7001 with a finger or the like. The remote controller 7111 may be provided with a display portion for displaying information output from the remote controller 7111. With operation keys or a touch panel of the remote controller 7111, channels and volume can be controlled and images displayed on the display portion 7001 can be controlled.

The electronic devices illustrated in FIGS. 9A to 9F can have a variety of functions, such as a function of displaying a variety of information (a still image, a moving image, a text image, and the like) on the display portion, a touch panel function, a function of displaying a calendar, date, time, and the like, a function of controlling processing with a variety of types of software (programs), a wireless communication function, a function of being connected to a variety of computer networks with a wireless communication function, a function of transmitting and receiving a variety of data with a wireless communication function, and a function of reading a program or data stored in a recording medium and displaying the program or data on the display portion. Furthermore, the electronic device including a plurality of display portions can have a function of displaying image data mainly on one display portion while displaying text data mainly on another display portion, a function of displaying a three-dimensional image by displaying images on a plurality of display portions with a parallax taken into account, or the like. Furthermore, the electronic device including an image receiving portion can have a function of shooting a still image, a function of shooting a moving image, a function of automatically or manually correcting a shot image, a function of storing a shot image in a recording medium (an external recording medium or a recording medium incorporated in the camera), a function of displaying a shot image on the display portion, or the like. Note that functions that can be provided for the electronic devices illustrated in FIGS. 9A to 9F are not limited to those described above, and the electronic devices can have a variety of functions.

Figure 9G:
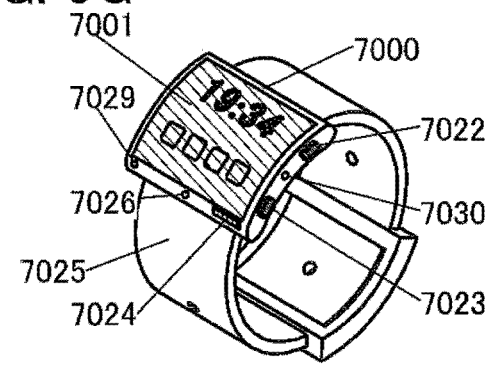
FIG. 9G illustrates a portable information terminal.

FIG. 9G illustrates a watch-type portable information terminal, which can be used as a watch-type electronic device, for example. The watch-type portable information terminal includes the housing 7000, the display portion 7001, operation buttons 7022 and 7023, a connection terminal 7024, a band 7025, a microphone 7026, a sensor 7029, a speaker 7030, and the like. The display surface of the display portion 7001 is curved, and images can be displayed on the curved display surface. Furthermore, mutual communication between the portable information terminal and, for example, a headset capable of wireless communication can be performed, and thus hands-free calling is possible with the portable information terminal. Note that the connection terminal 7024 allows mutual data transmission with another information terminal and charging. Wireless power feeding can also be employed for the charging operation.

The display portion 7001 mounted in the housing 7000 serving as a bezel includes a non-rectangular display region. The display portion 7001 can display an icon indicating time, another icon, and the like. The display portion 7001 may be a touch panel (input/output device) including a touch sensor (input device).

The watch-type electronic device illustrated in FIG. 9G can have a variety of functions, such as a function of displaying a variety of information (a still image, a moving image, a text image, and the like) on the display portion, a touch panel function, a function of displaying a calendar, date, time, and the like, a function of controlling processing with a variety of types of software (programs), a wireless communication function, a function of being connected to a variety of computer networks with a wireless communication function, a function of transmitting and receiving a variety of data with a wireless communication function, and a function of reading a program or data stored in a recording medium and displaying the program or data on the display portion.

The housing 7000 can include a speaker, a sensor (a sensor having a function of measuring force, displacement, position, speed, acceleration, angular velocity, rotational frequency, distance, light, liquid, magnetism, temperature, a chemical substance, sound, time, hardness, an electric field, current, voltage, electric power, radiation, flow rate, humidity, gradient, oscillation, odor, or infrared rays), a microphone, and the like.

Note that the light-emitting apparatus of one embodiment of the present invention can be used in the display portion of each electronic device described in this embodiment, so that a long-lifetime electronic device can be obtained.

Figure 10A:
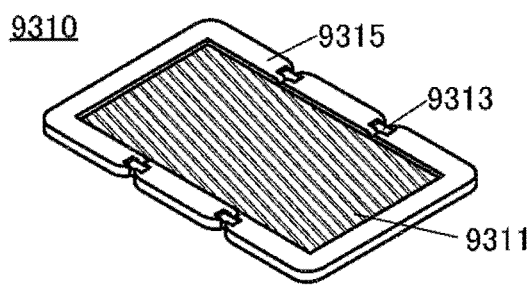
FIGS. 10A to 10C illustrate a foldable portable information terminal.
Figure 10B:
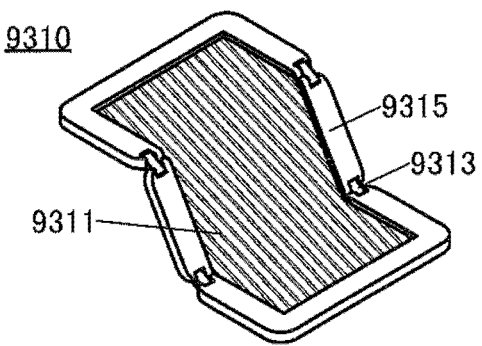
Figure 10C:
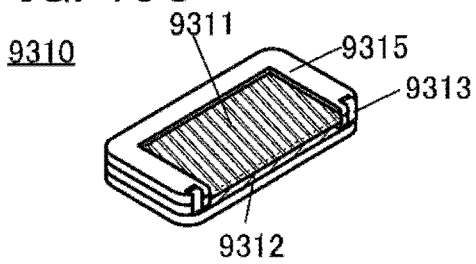

Another electronic device including the light-emitting apparatus is a foldable portable information terminal illustrated in FIGS. 10A to 10C. FIG. 10A illustrates a portable information terminal 9310 which is opened. FIG. 10B illustrates the portable information terminal 9310 which is being opened or being folded. FIG. 10C illustrates the portable information terminal 9310 which is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (input/output device) including a touch sensor (input device). By bending the display portion 9311 at a connection portion between two housings 9315 with the use of the hinges 9313, the portable information terminal 9310 can be reversibly changed in shape from an opened state to a folded state. The light-emitting apparatus of one embodiment of the present invention can be used for the display portion 9311. In addition, a long-lifetime electronic device can be obtained. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of application and the like can be smoothly performed.

Figure 11A:
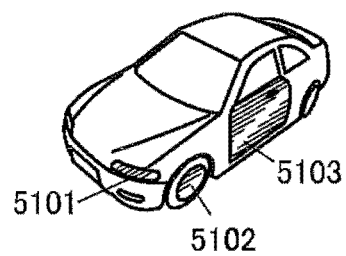
FIGS. 11A and 11B illustrate an automobile.
Figure 11B:
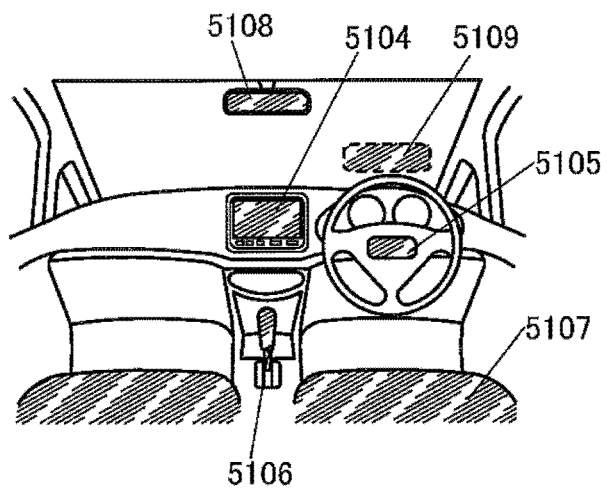

FIGS. 11A and 11B illustrate an automobile including the light-emitting apparatus. The light-emitting apparatus can be incorporated in the automobile, and specifically, can be included in lights 5101 (including lights of the rear part of the car), a wheel cover 5102, a part or whole of a door 5103, or the like on the miter side of the automobile which is illustrated in FIG. 11A. The light-emitting apparatus can also be included in a display portion 5104, a steering wheel 5105, a gear lever 5106, a seat 5107, an inner rearview mirror 5108, an windshield 5109, or the like on the inner side of the automobile which is illustrated in FIG. 11B, or in a part of a glass window.

In the above manner, the electronic devices and automobiles can be obtained using the light-emitting apparatus of one embodiment of the present invention. In that case, a long-lifetime electronic device can be obtained. Note that the light-emitting apparatus can be used for electronic devices and automobiles in a variety of fields without being limited to those described in this embodiment.

The structures described in this embodiment can be used in combination with any of the structures described in the other embodiments, as appropriate.

Embodiment 7

In this embodiment, the structure of a lighting device fabricated using the light-emitting apparatus of one embodiment of the present invention or the light-emitting device which is part of the light-emitting apparatus will be described with reference to FIG. 12 and FIG. 13.

Figure 12:
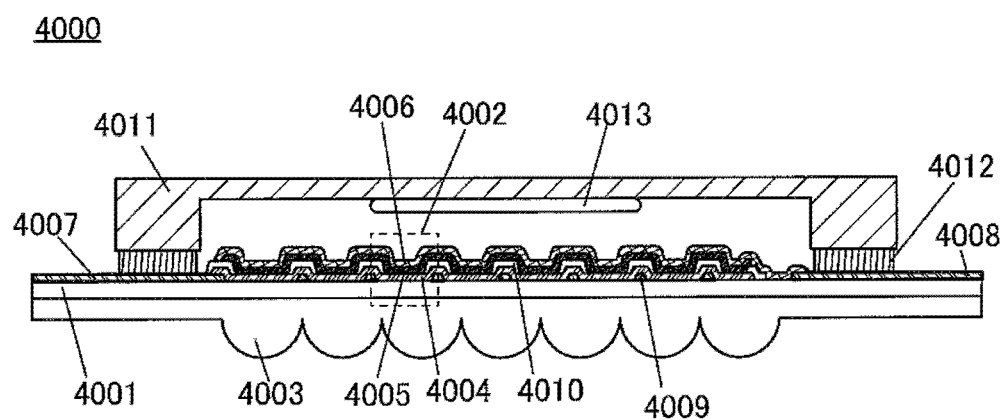
FIG. 12 illustrates a lighting device.
Figure 13:
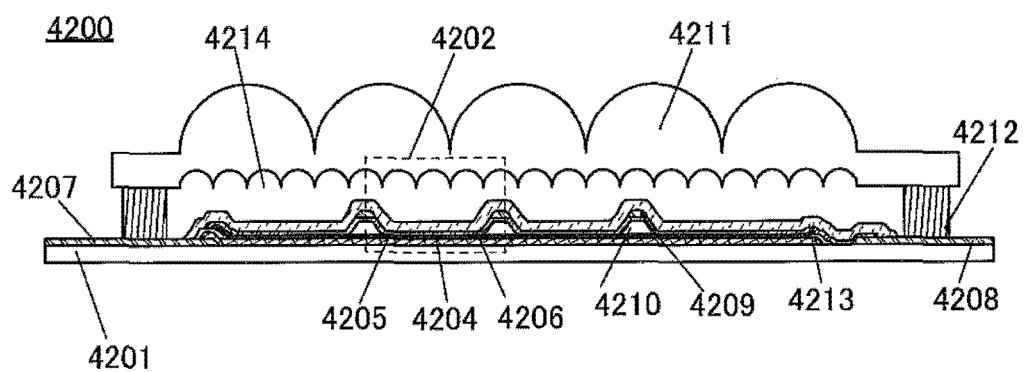
FIG. 13 illustrates a lighting device.

FIG. 12 and FIG. 13 are examples of cross-sectional views of lighting devices.

FIG. 12 illustrates a bottom-emission lighting device in which light is extracted from the substrate side, and FIG. 13 illustrates a top-emission lighting device in which light is extracted from the sealing substrate side.

A lighting device 4000 illustrated in FIG. 12 includes a light-emitting device 4002 over a substrate 4001. In addition, the lighting device 4000 includes a substrate 4003 with unevenness on the outside of the substrate 4001. The light-emitting device 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting device 4002. The substrate 4003 has the unevenness illustrated in FIG. 12, whereby the extraction efficiency of light emitted from the light-emitting device 4002 can be increased.

A lighting device 4200 illustrated in FIG. 13 includes a light-emitting device 4202 over a substrate 4201. The light-emitting device 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting device 4202. The sealing substrate 4211 has the unevenness illustrated in FIG. 13, whereby the extraction efficiency of light emitted from the light-emitting device 4202 can be increased.

Examples of such lighting devices include a ceiling light as an indoor lighting. Examples of the ceiling light include a direct-mount light and an embedded light. Such lighting devices are fabricated using the light-emitting apparatus and a housing or a cover in combination.

For another example, such lighting devices can be used for a foot light that lights a floor so that safety on the floor can be improved. A foot light can be effectively used in a bedroom, on a staircase, or on a passage, for example. In that case, the size or shape of the foot light can be changed in accordance with the area or structure of a room. The foot light can be a stationary lighting device fabricated using the light-emitting apparatus and a support in combination.

Such lighting devices can also be used for a sheet-like lighting device (sheet-like lighting). The sheet-like lighting, which is attached to a wall when used, is space-saving and thus can be used for a wide variety of uses. Furthermore, the area of the sheet-like lighting can be easily increased. The sheet-like lighting can also be used on a wall or housing having a curved surface.

Besides the above examples, when the light-emitting apparatus of one embodiment of the present invention or the light-emitting device which is part of the light-emitting apparatus is used as part of furniture in a room, a lighting device that functions as the furniture can be obtained.

As described above, a variety of lighting devices that include the light-emitting apparatus can be obtained. Note that these lighting devices are also embodiments of the present invention.

The structures described in this embodiment can be used in combination with any of the structures described in the other embodiments, as appropriate.

Example 1

Synthesis Example 1

In this example, a method of synthesizing 9,10-di(biphenyl-2-yl)-N,N'-bis(3,5-di-tert-butylphenyl)-N,N'-bis(9-phenyl-9H-carbazol-3-yl)anthracene-2,6-diamine (abbreviation: 2,6PCAPA-03), which is the compound of one embodiment of the present invention represented by Structural Formula (100) in Embodiment 1, will be described. The structure of 2,6PCAPA-03 is shown below.

[Chemical Formula 28]

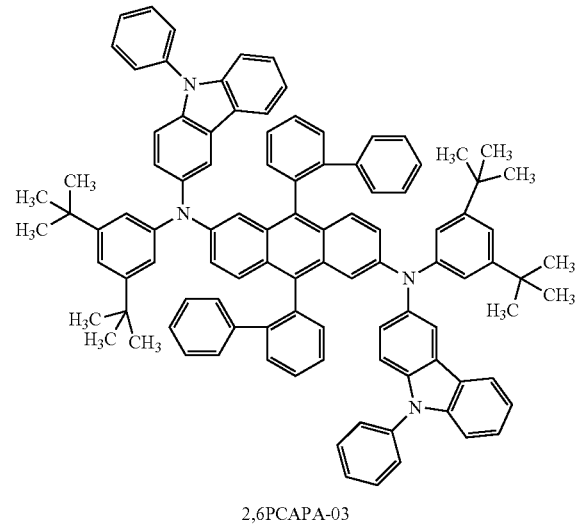

2,6PCAPA-03

Step 1: Synthesis of N-(3,5-di-tert-butylphenyl)-9-phenyl-9H-carbazol-3-amine

Into a 200-mL three-neck flask were put 3.7 g (10 mmol) of 3-iodo-9-phenylcarbazole, 2.2 g (11 mmol) of 3,5-di-tert-butylphenyl aniline, and 2.1 g (22 mmol) of sodium-t-butoxide, and the air in the flask was replaced with nitrogen. To this mixture was added 100 mL of toluene, and the mixture was degassed by being stirred under reduced pressure. To this mixture were added 0.5 mL (0.16 mmol) of tri-tert-butylphosphine (a 10 wt % hexane solution) and 90 mg (0.16 mmol) of bis(dibenzylideneacetone)palladium(0) and then, stirring was performed for 3 hours at 90° C. under a nitrogen stream.

After the stirring, 500 mL of toluene was added to the resulting mixture and then, suction filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina to give a filtrate. The obtained filtrate was concentrated to give a brown solid.

The obtained solid was purified by silica gel chromatography (hexane:toluene=7:3 as a developing solvent) to give 3.9 g of a white solid in a yield of 87%. A synthesis scheme of Step 1 is shown in (a-1) below.

[Chemical Formula 29]

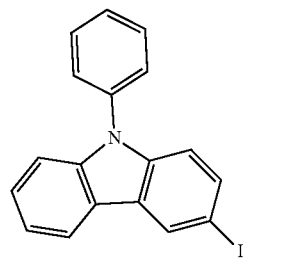

+

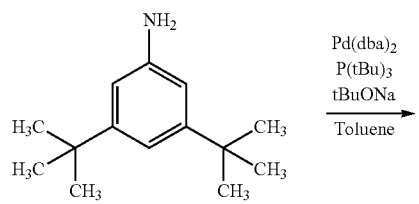

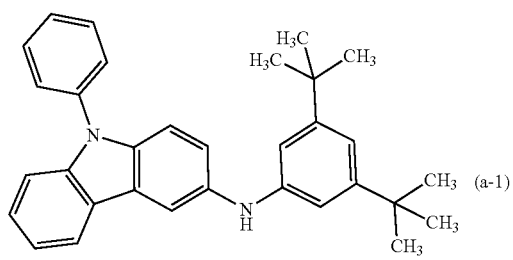

Results of $^1$H NMR measurement of the white solid obtained in Step 1 are shown below. The results indicate that N-(3,5-di-tert-butylphenyl)-9-phenyl-9H-carbazol-3-amine was obtained.

$^1$H NMR (CD$_2$Cl$_2$, 300 MHz):σ=8.05-8.02 (m, 1H), 7.92 (d, J=2.1 Hz, 1H), 7.66-7.58 (m, 4H), 7.50-7.35 (m, 4H), 7.27-7.19 (m, 2H), 6.98-6.94 (m, 3H), 5.83 (bs, 1H), 1.31 (s, 18H).

Step 2: Synthesis of 2,6PCAPA-03

Into a 200 mL three-neck flask were put 1.0 g (1.6 mmol) of 9,10-di(biphenyl-2-yl)-2,6-dibromoanthracene, 1.4 g (3.2 mmol) of N-(3,5-di-tert-butylphenyl)-9-phenyl-9H-carbazol-3-amine, 0.60 g (6.2 mmol) of sodium-tert-butoxide, and 60 mg (0.15 mmol) of 2-dicyclohexylphosphino-2',6'-dimethoxybiphenyl (abbreviation: SPhos), and the air in the flask was replaced with nitrogen. To this mixture 20 mL of xylene was added, and the resulting mixture was degassed by being stirred under reduced pressure. To this mixture was added 40 mg (70 μmol) of bis(dibenzylideneacetone)palladium(0), and stirring was performed at 150° C. for 6 hours under a nitrogen stream.

After the stirring, 500 mL of toluene was added to the resulting mixture and then, suction filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina to give a filtrate. The obtained filtrate was concentrated to give a brown solid.

This solid was purified by silica gel column chromatography (hexane:toluene=3:2 as a developing solvent) to give a target yellow solid. The obtained yellow solid was recrystallized with toluene to give 0.96 g of a target yellow solid in a yield of 45%. A synthesis scheme of Step 2 is shown in (a-2) below.

[Chemical Formula 30]

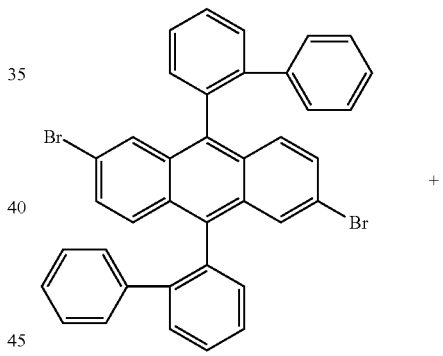

+

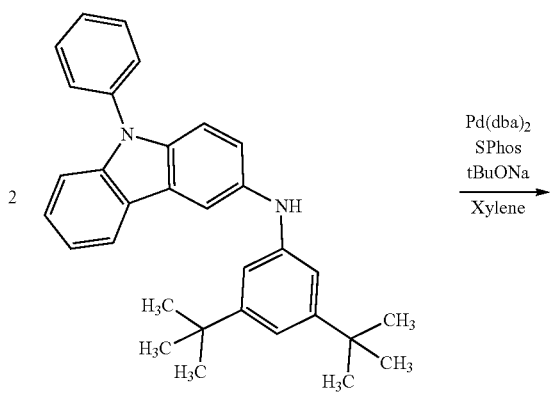

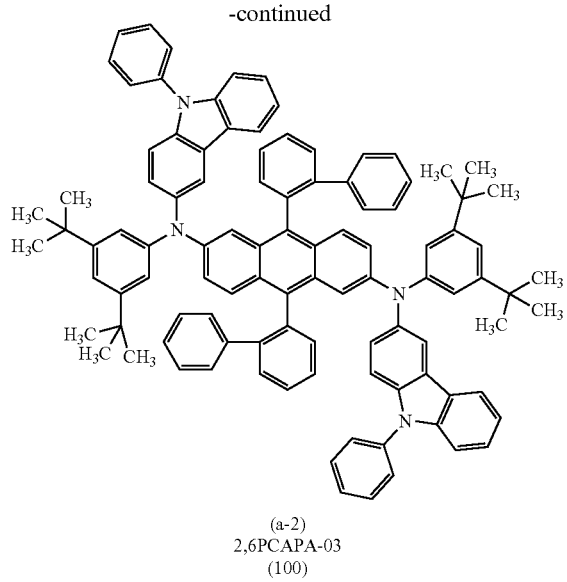

(a-2)
2,6PCAPA-03
(100)

By a train sublimation method, 0.96 g of the obtained yellow solid was purified. In the purification, the yellow solid was heated at 345° C. for 15 hours under a pressure of 3.2 Pa. After the purification, 0.91 g of a target yellow solid was obtained at a collection rate of 95%.

Figure 14:
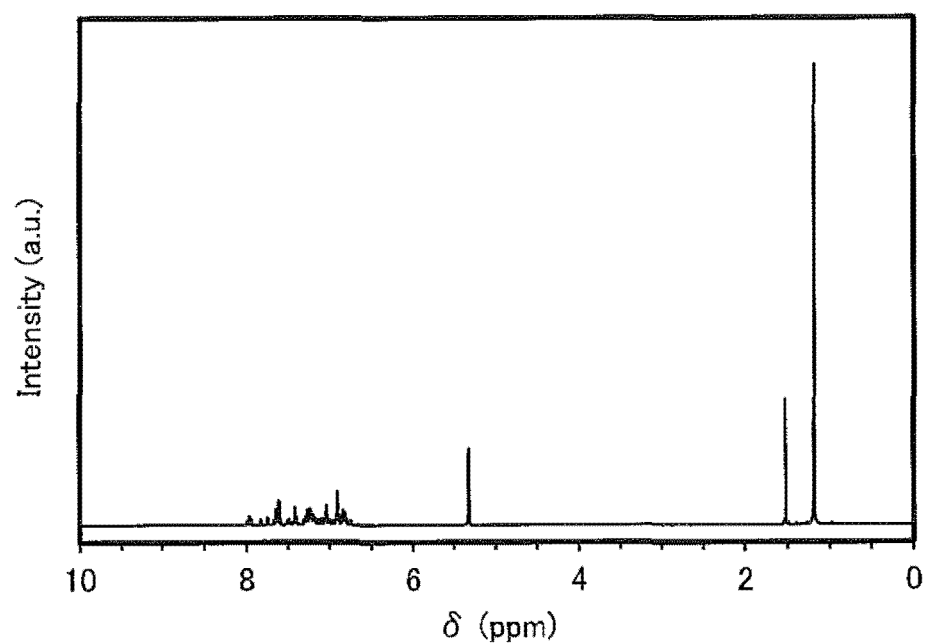
FIG. 14 is a $^1$H-NMR chart of an organic compound represented by Structural Formula (100).

Results of $^1$H NMR measurement of the yellow solid obtained in Step 2 are shown below. FIG. 14 is a $^1$H NMR chart. The results reveal that 2,6PCAPA-03 (Structural Formula (100)) was obtained.

$^1$H NMR(CD$_2$Cl$_2$, 300 MHz):σ=7.99-7.94 (m, 2H), 7.83-7.74 (m, 2H), 7.67-7.59 (m, 8H), 7.52-7.37 (m, 6H), 7.32-7.14 (m, 14H), 7.12-6.74 (m, 22H), 1.19 (s, 36H).

Figure 15:
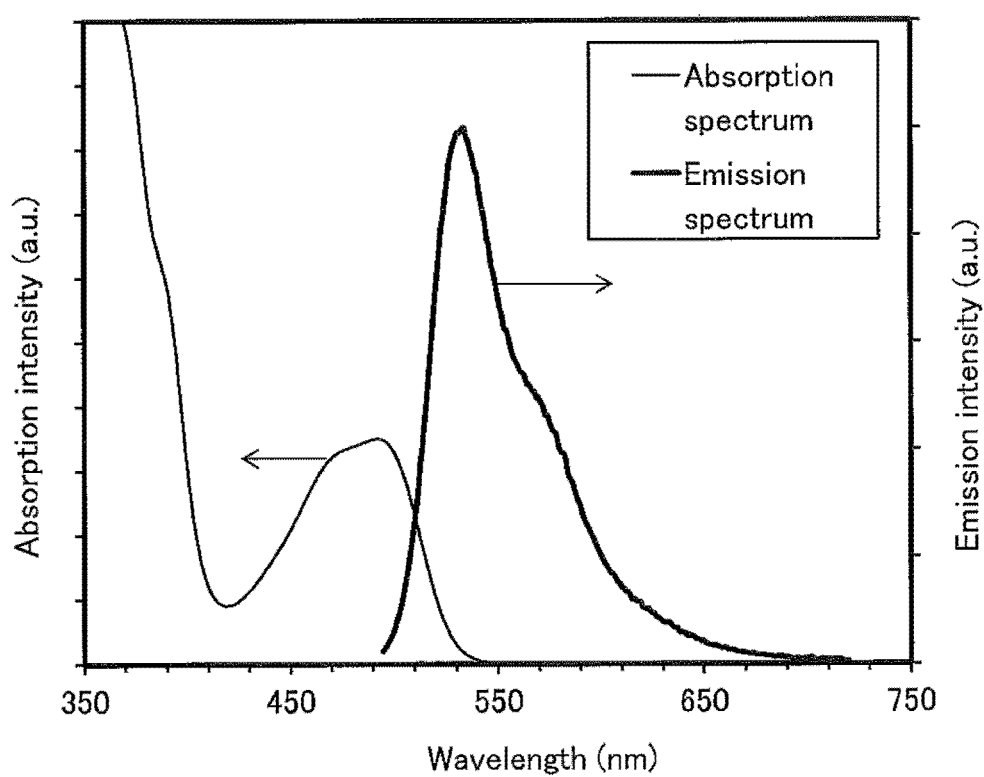
FIG. 15 shows an ultraviolet-visible absorption spectrum and an emission spectrum of the organic compound represented by Structural Formula (100).

Next, the absorption and emission spectra of 2,6PCAPA-03 in a toluene solution were measured. An ultraviolet-visible absorption spectrum (hereinafter simply referred to as an absorption spectrum) and an emission spectrum were measured. The absorption spectrum was measured with an ultraviolet-visible spectrophotometer (V-550, produced by JASCO Corporation). The emission spectrum was measured with a spectrofluorometer (FP-8600DS, produced by JASCO Corporation). FIG. 15 shows the obtained absorption and emission spectra of 2,6PCAPA-03 in the toluene solution. The horizontal axis represents wavelength and the vertical axis represents absorption intensity.

As shown in FIG. 15, 2,6PCAPA-03 in the toluene solution has an absorption peak at around 493 nm and an emission wavelength peak at 534 nm (excitation wavelength: 480 nm).

Example 2

In this example, light-emitting devices were fabricated using the compound of one embodiment of the present invention and operation characteristics thereof were measured. Light-emitting Device 1-1, Light-emitting Device 1-2, Comparative Light-emitting Device 1-a, and Comparative light-emitting Device 1-b are described in this example. Each of these light-emitting devices has a device structure illustrated in FIG. 16. A light-emitting layer 913 in this example has a structure described in Structure example 7 of the light-emitting layer in Embodiment 1, and specifically has a structure shown in Table 1. A light-emitting layer of each of Light-emitting Device 1-1 and Light-emitting Device 1-2 contains a compound of one embodiment of the present invention, 9,10-di(biphenyl-2-yl)-N,N'-bis(3,5-di-tert-butylphenyl)-N,N'-bis(9-phenyl-9H-carbazol-3-yl)anthracene-2,6-diamine (abbreviation: 2,6PCAPA-03) in addition to 3,5-bis(3-(9H-carbazol-9-yl)phenyl)pyridine (abbreviation: 35DCzPPy) and fac-tris[(2,6-diisopropylphenyl)-2-phenyl-1H-imidazole]iridium(III) (abbreviation: [Ir(iPrpim)$_3$]). The amounts of 2,6PCAPA-03 contained in Light-emitting Devices 1-1 and 1-2 are different. In Comparative Light-emitting Device 1-a which is used as a comparative example, 9,10-diphenyl-N,N'-diphenyl-N,N'-bis(9-phenyl-9H-carbazol-3-yl)anthracene-2,6-diamine (abbreviation: 2,6PCAPA) is used instead of 2,6PCAPA-03 used in the light-emitting layers of Light-emitting Devices 1-1 and 1-2. Comparative Light-emitting Device 1-b contains only 35DCzPPy and [Ir(iPrpim)$_3$] in a light-emitting layer. Chemical formulae of materials used in this example are shown below.

TABLE 1

| | First electrode 901 | Hole-injection layer 911 | Hole-transport layer 912 | Light-emitting layer 913 | Electron-transport layer 914 | Electron-injection layer 915 | Second electrode 903 |
|---|---|---|---|---|---|---|---|
| Light-emitting Device 1-1 | ITSO (70 nm) | DBT3P-II:MoOx (1:0.5 40 nm) | PCCP (20 nm) | * | 35DCzPPy (10 nm) | TmPyPB (20 nm) | LiF (1 nm) | Al (200 nm) |
| Light-emitting Device 1-2 | | | | ** | | | | |
| Comparative Light-emitting Device 1-a | | | | *** | | | | |
| Comparative Light-emitting Device 1-b | | | | ***** | | | | |

\* 35DCzPPy:[Ir(iPrpim)$_3$]:2,6PCAPA-03 (1:0.05:0.01 40 nm)

\*\* 35DCzPPy:[Ir(iPrpim)$_3$]:2,6PCAPA-03 (1:0.05:0.05 40 nm)

\*\*\* 35DCzPPy:[Ir(Prpim)$_3$]:2,6PCAPA (1:0.05:0.05 40 nm)

\*\*\*\*\* 35DCzPPy:[Ir(iPrpim)$_3$] (1:0.05 30 nm)

[Chemical Formula 31]
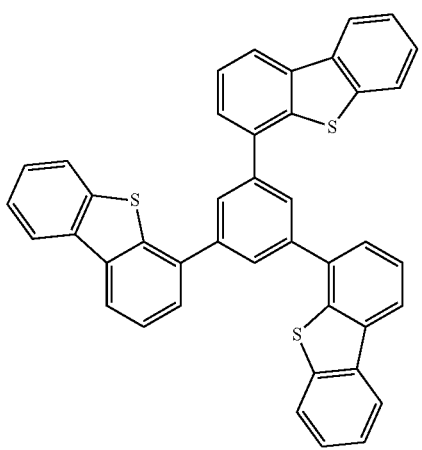
DBT3P-II
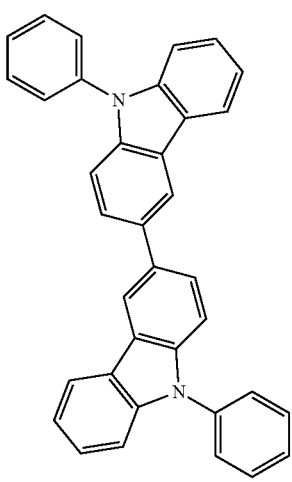
PCCP
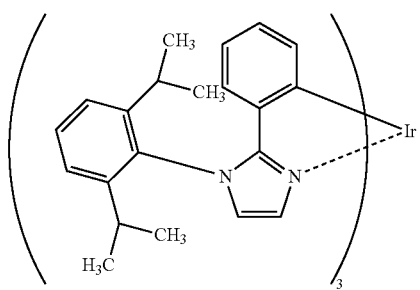
[Ir(iPrpim)₃]
(100)
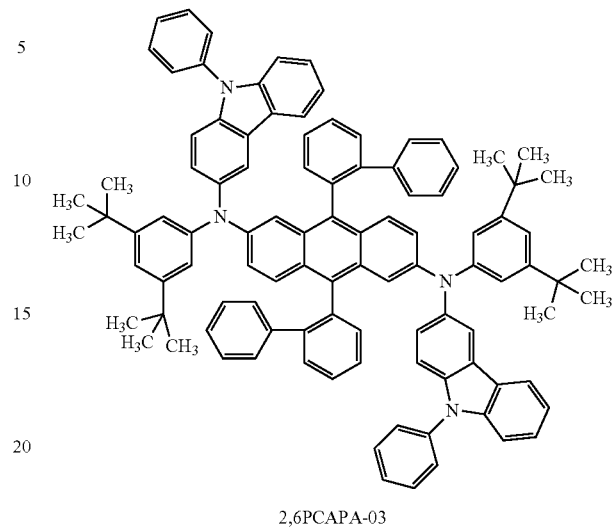
2,6PCAPA-03
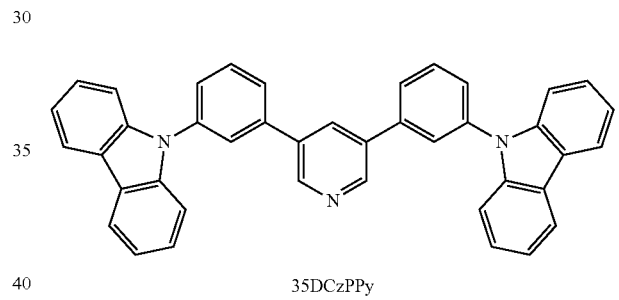
35DCzPPy
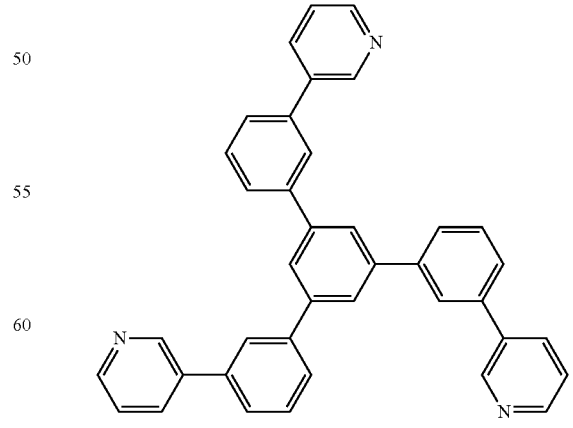
TmPyPB

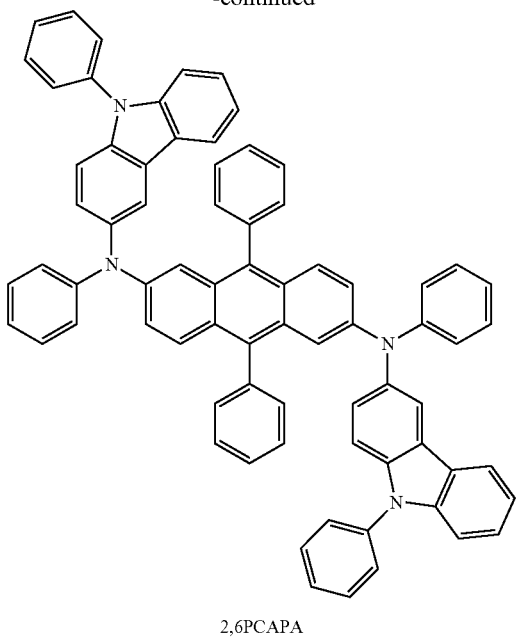

2,6PCAPA

<<Structure of Light-Emitting Devices>>

Figure 16:
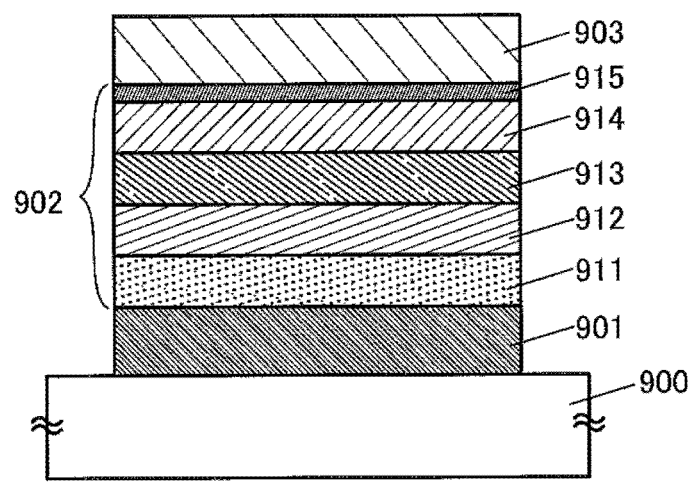
FIG. 16 illustrates a light-emitting device.

In each of the light-emitting devices described in this example, as illustrated in FIG. 16, a hole-injection layer 911, a hole-transport layer 912, a light-emitting layer 913, an electron-transport layer 914, and an electron-injection layer 915 are stacked in this order over a first electrode 901 formed over a substrate 900, and a second electrode 903 is stacked over the electron-injection layer 915.

A glass substrate was used as the substrate 900. As the first electrode 901, a film of indium tin oxide containing silicon oxide (ITSO) was used and the thickness was set to 70 nm. The electrode area of the first electrode 901 was 4 mm$^2$ (2 mm×2 mm).

As the hole-injection layer 911, a film formed by co-evaporation of 1,3,5-tri(dibenzothiophen-4-Abenzene (abbreviation: DBT3P-II) and molybdenum oxide (DBT3P-II: molybdenum oxide=1:0.5 (mass ratio)) was used and the thickness was set to 40 nm.

For the hole-transport layer 912, 3,3'-bis(9-phenyl-9H-carbazole) (abbreviation: PCCP) was used and the thickness was set to 20 nm.

For the light-emitting layer 913 of each of Light-emitting Devices 1-1 and 1-2, a film containing 35DCzPPy, [Ir(iPrpim)$_3$], and 2,6PCAPA-03 was used, and the thickness was set to 40 nm. For the light-emitting layer 913 of Comparative Light-emitting Device 1-a, a film containing 35DCzPPy, [Ir(iPrpim)$_3$], and 2,6PCAPA was used, and the thickness was set to 40 nm. For the light-emitting layer 913 of Comparative Light-emitting Device 1-b, a film containing 35DCzPPy and [Ir(iPrpim)$_3$] was used, and the thickness was set to 30 mu, Note that the weight ratios in the light-emitting layers 913 of the light-emitting devices, which are different from one another, are shown in Table 1.

As the electron-transport layer 914, a stacked film of 10-nm-thick 35DCzPPy and 20-nm-thick 1,3,5-tri[(3-pyridyl)-phenyl-3-yl] benzene (abbreviation: TmPyPB) was used.

For the electron-injection layer 915, lithium fluoride (LiF) was used and the thickness was set to 1 nm.

For the second electrode 903, aluminum was used and the thickness was set to 200 nm. In this example, the second electrode 903 functions as a cathode.

<<Operation Characteristics of Light-Emitting Devices>>

Operation characteristics of the fabricated light-emitting devices were measured. Luminance, CIE chromaticity, and electroluminescence (EL) spectra were measured with a spectroradiometer (SR-UL1R, produced by TOPCON TECHNOHOUSE CORPORATION). Note that the measurement was performed at room temperature (in an atmosphere kept at 23° C.).

Figure 17:
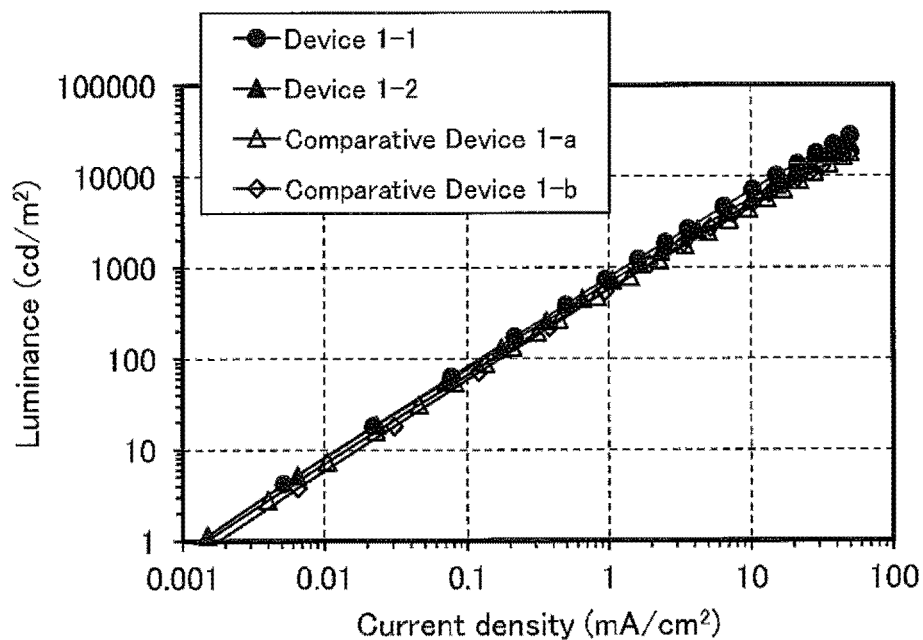
FIG. 17 shows current density-luminance characteristics of Light-emitting Devices 1-1 and 1-2 and Comparative Light-emitting Devices 1-a and 1-b.
Figure 18:
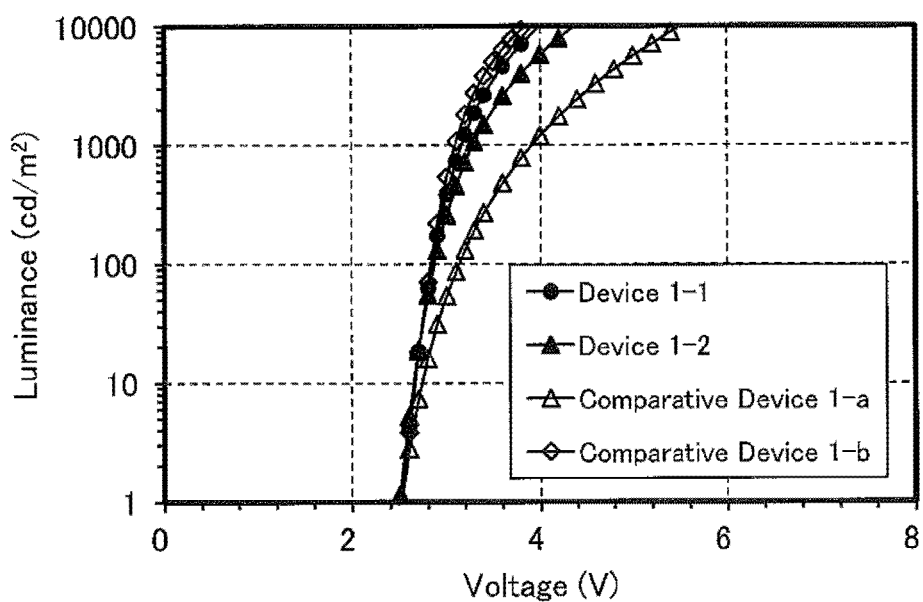
FIG. 18 shows voltage-luminance characteristics of Light-emitting Devices 1-1 and 1-2 and Comparative Light-emitting Devices 1-a and 1-b.
Figure 19:
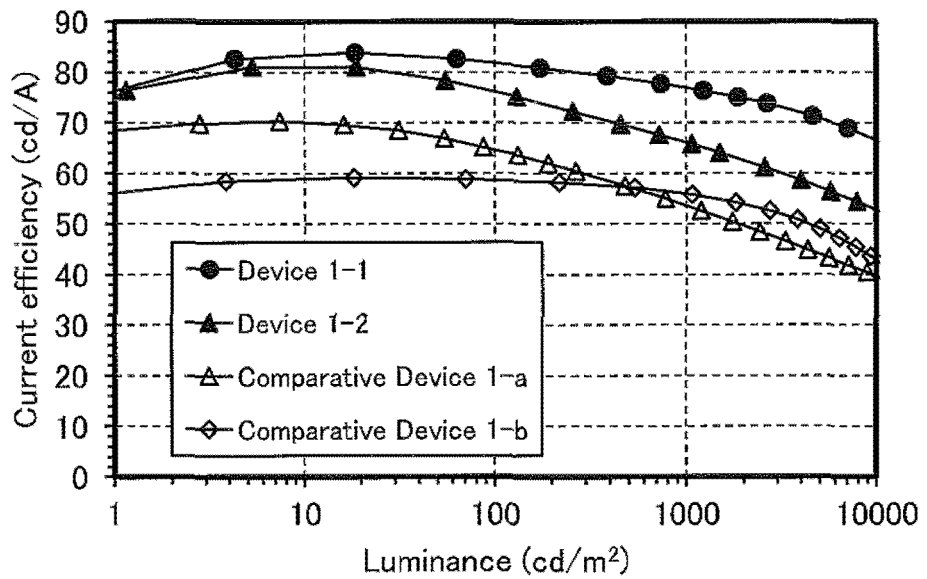
FIG. 19 shows luminance-current efficiency characteristics of Light-emitting Devices 1-1 and 1-2 and Comparative Light-emitting Devices 1-a and 1-b.
Figure 20:
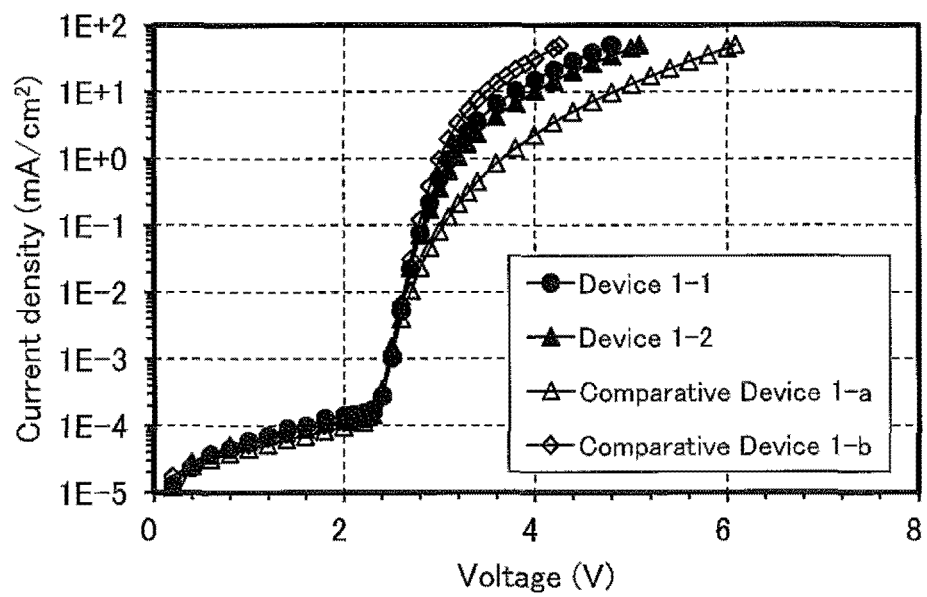
FIG. 20 shows voltage-current density characteristics of Light-emitting Devices 1-1 and 1-2 and Comparative Light-emitting Devices 1-a and 1-b.
Figure 21:
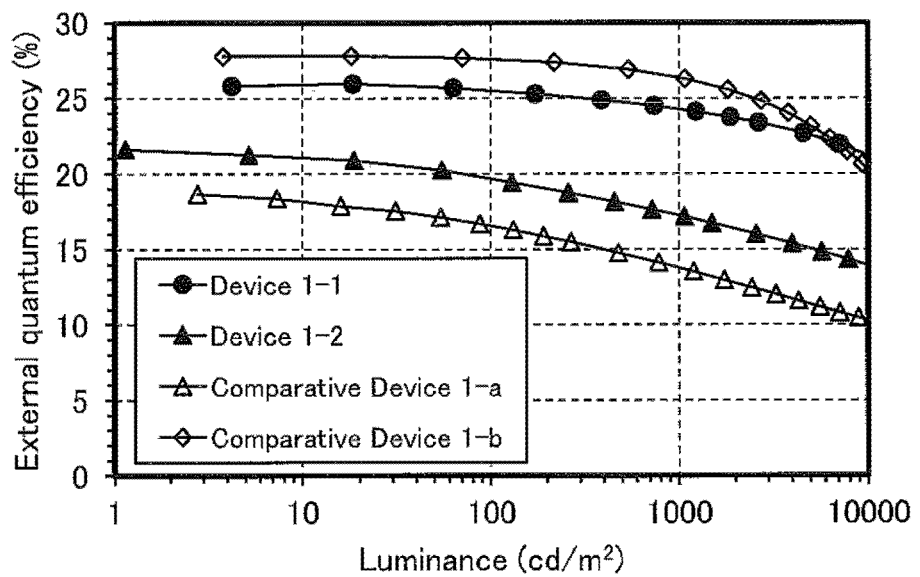
FIG. 21 shows luminance-external quantum efficiency characteristics of Light-emitting Devices 1-1 and 1-2 and Comparative Light-emitting Devices 1-a and 1-b.

As the operation characteristics of Light-emitting Devices 1-1 and 1-2 and Comparative Light-emitting Devices 1-a and 1-b fabricated in this example, FIG. 17 shows current density-luminance characteristics, FIG. 18 shows voltage-luminance characteristics, FIG. 19 shows luminance-current efficiency characteristics, FIG. 20 shows voltage-current density characteristics, and FIG. 21 shows luminance-external quantum efficiency characteristics.

Figure 22:
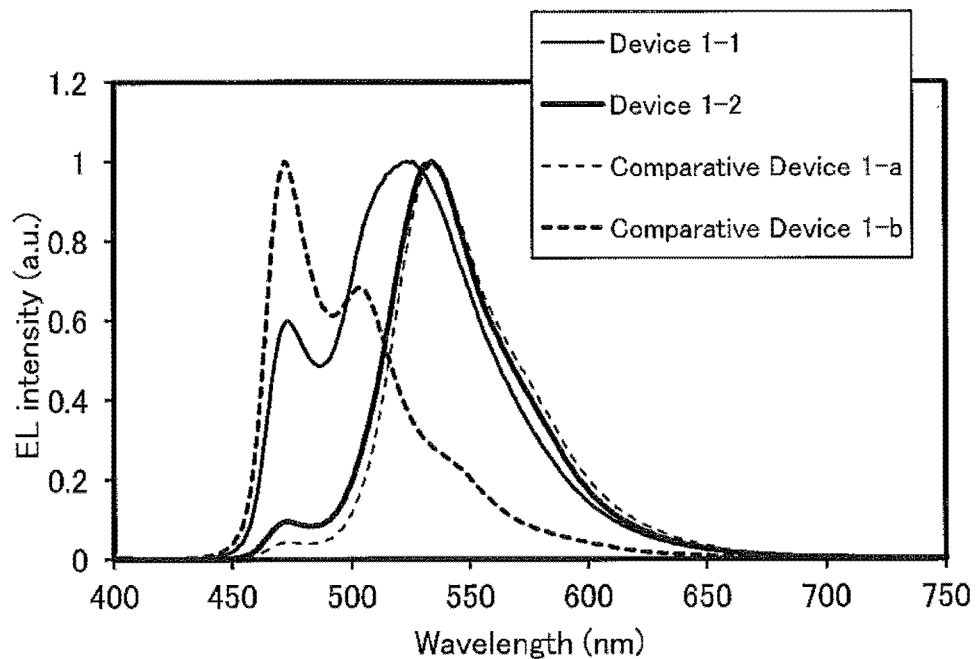
FIG. 22 shows electroluminescence spectra of Light-emitting Devices 1-1 and 1-2 and Comparative Light-emitting Devices 1-a and 1-b.

FIG. 22 shows electroluminescence spectra (EL spectra) when a current with a current density of 2.5 mA/cm$^2$ was supplied to each of the light-emitting devices.

Next, Table 2 shows the initial values of main characteristics of the light-emitting devices at around 1000 cd/m$^2$.

TABLE 2

| | Voltage (V) | Current (mA) | Current density (mA/cm$^2$) | Chromaticity x | y | Luminance (cd/m$^2$) | Current efficiency (cd/A) | Power efficiency (lm/W) | External quantum efficiency (%) |
|---|---|---|---|---|---|---|---|---|---|
| Light-emitting Device 1-1 | 3.2 | 0.064 | 1.6 | 0.25 | 0.54 | 1200 | 76 | 75 | 24 |
| Light-emitting Device 1-2 | 3.3 | 0.065 | 1.6 | 0.32 | 0.62 | 1100 | 66 | 63 | 17 |
| Comparative Light-emitting Device 1-a | 4.0 | 0.091 | 2.3 | 0.34 | 0.62 | 1200 | 53 | 41 | 14 |
| Comparative Light-emitting Device 1-b | 3.1 | 0.077 | 1.9 | 0.16 | 0.36 | 1100 | 56 | 57 | 26 |

Light-emitting Devices 1-1 and 1-2 are different from Comparative Light-emitting Device 1-b in that 2,6PCAPA-03, the compound of one embodiment of the present invention, is additionally contained in the light-emitting layer. As shown in FIG. 22, the EL spectrum of Comparative Light-emitting Device 1-b exhibited light-blue light emission having a peak wavelength of 472 nm and originating from a phosphorescent substance, [Ir(iPrpim)₃]. The EL spectrum of Light-emitting Device 1-1 exhibited both light emission having a peak wavelength of around 530 nm and originating from 2,6PCAPA-03 and light emission having a peak wavelength of around 472 mu and originating from [Ir(iPrpim)₃]. The EL spectrum of Light-emitting Device 1-2 exhibited green light emission having a peak wavelength of around 530 nm and originating from 2,6PCAPA-03. This indicates that in Light-emitting Devices 1-1 and 1-2,2,6PCAPA-03, which is a fluorescent substance, receives excitation energy and emits light. The EL spectrum of Light-emitting Device 1-2 having a high concentration of the fluorescent substance exhibited light emission mostly originating from 2,6PCAPA-03. This indicates that the fluorescent substance having a higher concentration of the fluorescent substance is more likely to receive excitation energy and emit light. The above results show that Light-emitting Device 1-2 shows a high external quantum efficiency of 20% or higher despite the light emission originating from the fluorescent substance. The generation probability of singlet excitons which are generated by recombination of carriers (holes and electrons) injected from the pair of electrodes is at most 25%, and thus the external quantum efficiency of a fluorescent element in the case where the light extraction efficiency to the outside is 30% is at most 7.5%. Meanwhile, Light-emitting Device 1-2 has an external quantum efficiency of more than 7.5%. This is because, in addition to light emission derived from singlet excitons generated by recombination of carriers (holes and electrons) injected from a pair of electrodes, light emission derived from energy transfer from triplet excitons can be obtained from the fluorescent substance.

Thus, it is found that the compound of one embodiment of the present invention, 2,6PCAPA-03, can prevent deactivation of triplet excitation energy, which becomes problematic particularly when the concentration is high, and emits light efficiently in the light-emitting layers of the light-emitting devices. When Light-emitting Device 1-2 and Comparative Light-emitting Device 1-a were compared, the external quantum efficiency of Comparative Light-emitting Device 1-a, which included 2,6PCAPA in the light-emitting layer at the same concentration of 2,6PCAPA-03 in Light-emitting Device 1-2, was lower than that of Light-emitting Device 1-2. This means that 2,6PCAPA-03 (which includes a protective group) used in Light-emitting Device 1-2 can suppress triplet excitation energy transfer from the host due to the Dexter mechanism and convert both singlet excitation energy and triplet excitation energy into light emission efficiently, as compared with 2,6PCAPA (which does not include a protective group) used in Comparative Light-emitting Device 1-a, which significantly influences the external quantum efficiency.

Figure 23:
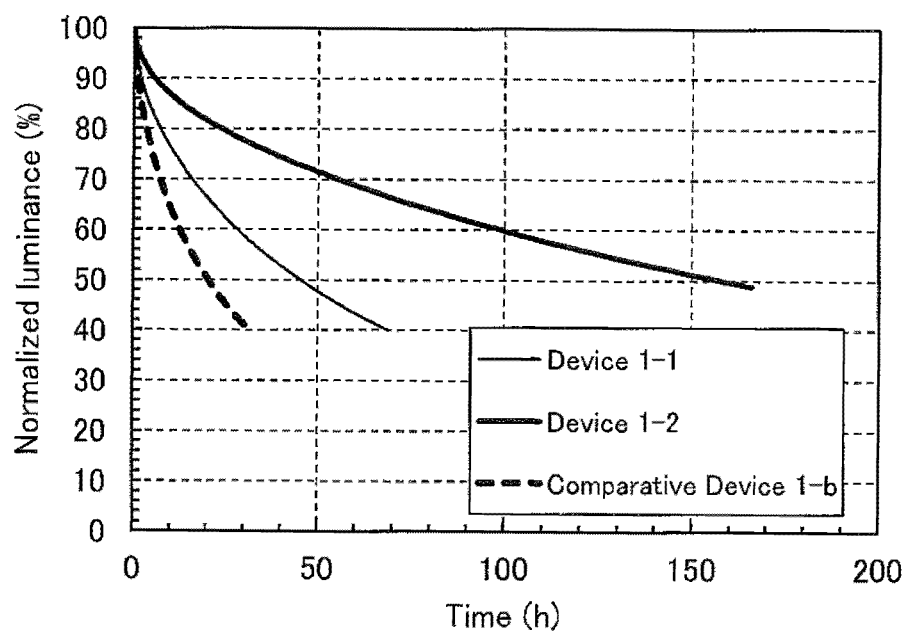
FIG. 23 shows reliability measurement results of Light-emitting Devices 1-1 and 1-2 and Comparative Light-emitting Devices 1-a and 1-b.

Driving tests of Light-emitting Devices 1-1 and 1-2 and Comparative Light-emitting Device 1-b at a constant current density of 12.5 mA/cm 2 were performed. FIG. 23 shows the results. The results show that an increase in the concentration of 2,6PCAPA-03 improves the reliability while high emission efficiency is achieved. This means that by increasing the concentration of a guest in the light-emitting layer, excitation energy in the light-emitting layer can be efficiently converted into light emission of the guest and non-radiative deactivation can be inhibited. In other words, it is suggested that an increase in the concentration of the guest can prevent energy transfer from the host to the guest due to the Dexter mechanism and can increase the rate of the energy transfer from the host to the guest due to the Förster mechanism. Therefore, the light-emitting device including the compound of one embodiment of the present invention has high emission efficiency and high reliability.

Example 3

Synthesis Example 2

In this example, a method of synthesizing 9,10-di(biphenyl-2-yl)-N,N'-bis[3,5-bis-(2-adamantyl)phenyl]-N,N'-bis(dibenzofuran-3-yl)anthracene-2,6-diamine (abbreviation: 2,6FrAPA), which is a compound of one embodiment of the present invention represented by Structural Formula (112) in Embodiment 1, will be described. The structure of 2,6FrAPA is shown below.

[Chemical Formula 32]

(112)

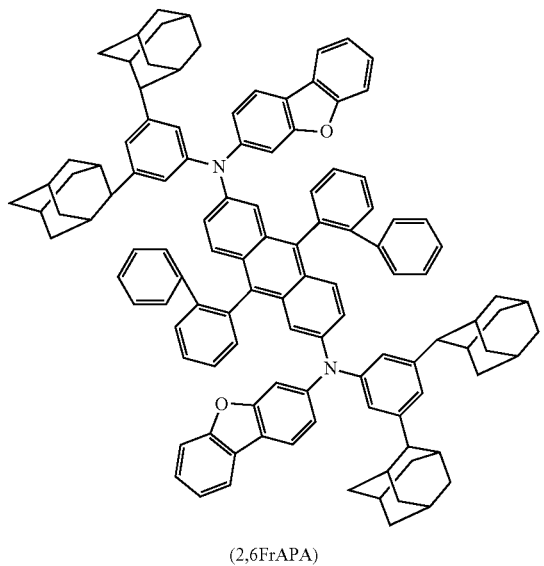

(2,6FrAPA)

The compound 2,6FrAPA shown above can be synthesized in a similar manner using 3,5-bis(2-adamantyl)phenyl trifluoromethansulfonate and di benzo[b,d] furan-3-amine instead of 3-iodo-9-phenylcarbazole and 3,5-di-tert-butylphenylaniline used in Step 1 of Example 1 by the methods shown in Synthesis Schemes (b-1) and (b-2). The compound emits green light.

[Chemical Formula 33]
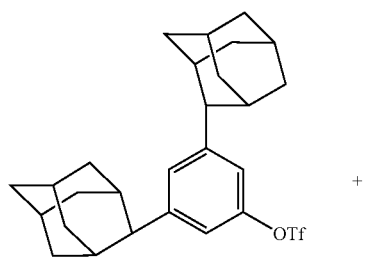
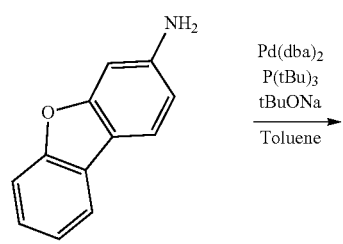
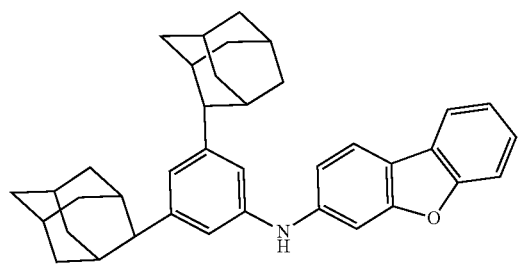
(b-1)
[Chemical Formula 34]
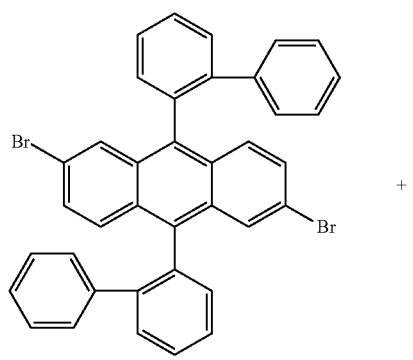
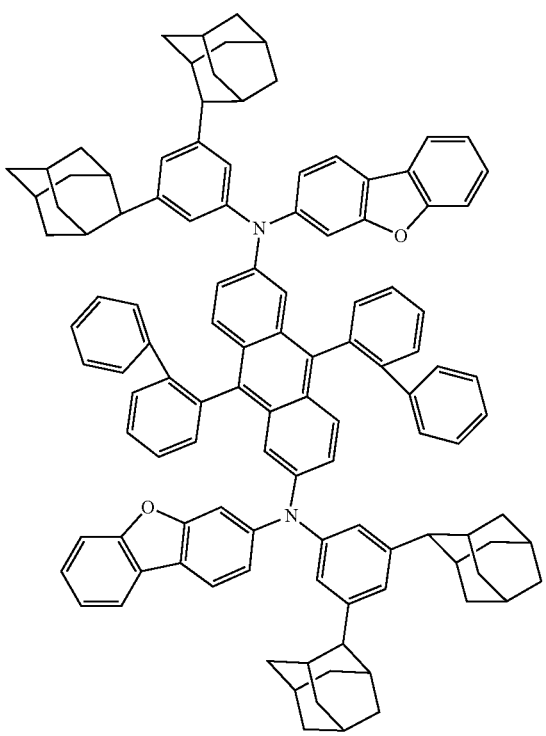
(b-2)
(2,6FrAPA)
(112)
Thus, the compound of one embodiment of the present invention represented by Structure Formula (112), 2,6FrAPA can be obtained.
This application is based on Japanese Patent Application Serial No. 2019-239346 filed with Japan Patent Office on Dec. 27, 2019, the entire contents of which are hereby incorporated by reference.

What is claimed is:

1. A compound represented by General formula (G1):

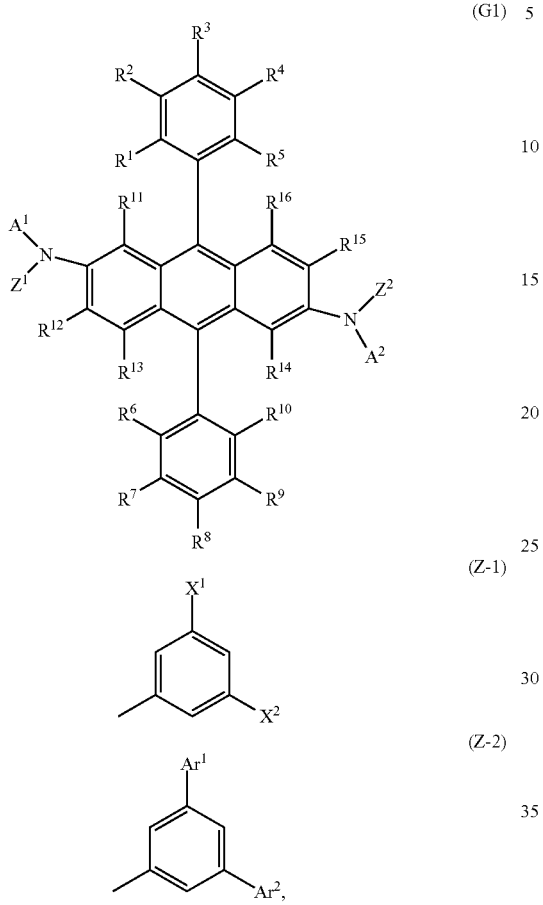

wherein in General Formula (G1), each of $A^1$ and $A^2$ independently represents a substituted or unsubstituted condensed heteroaromatic ring having 3 to 30 carbon atoms, or a structure represented by General Formula (Z-1) or General Formula (Z-2); and each of $Z^1$ and $Z^2$ independently has a structure represented by General Formula (Z-1) or (Z-2), wherein in General Formula (Z-1), each of $X^1$ and $X^2$ independently represents any one of an alkyl group having 3 to 10 carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms, wherein each of $Ar^1$ and $Ar^2$ independently represents a substituted or unsubstituted aromatic hydrocarbon group having 6 to 13 carbon atoms, and at least one of $Ar^1$ and $Ar^2$ represents a substituted aromatic hydrocarbon group having 6 to 13 carbon atoms, wherein a substituent of the substituted aromatic hydrocarbon group having 6 to 13 carbon is represented by any one of an alkyl group having 3 to 10 carbon atoms, a substituted or unsubstituted cycloalkyl group having 3 to 10 carbon atoms, a cycloalkyl group having a bridge structure having 7 to 10 carbon atoms, and a trialkylsilyl group having 3 to 12 carbon atoms, wherein each of $R^1$ to $R^{16}$ independently represents any one of hydrogen, an alkyl group having 3 to 10 carbon atoms, a substituted or unsubstituted cycloalkyl group having 3 to 10 carbon atoms, a trialkylsilyl group having 3 to 12 carbon atoms, and a substituted or unsubstituted aryl group having 6 to 25 carbon atoms, and wherein the substituted or unsubstituted condensed heteroaromatic ring having 3 to 30 carbon atoms represents a condensed heteroaromatic ring including a pyrrole ring, a dibenzofuran ring, or a dibenzothiophene ring.

2. A light-emitting device comprising an EL layer between a pair of electrodes,
wherein the EL layer comprises a light-emitting layer, and
wherein the light-emitting layer comprises the compound according to claim 1.

3. A light-emitting device comprising an EL layer between a pair of electrodes,
wherein the EL layer comprises a light-emitting layer, and
wherein the light-emitting layer comprises a phosphorescent material and the compound according to claim 1.

4. A lighting device comprising:
the light-emitting device according to claim 2; and
at least one of a housing, a cover, and a support base.

5. A compound represented by General formula (G2):

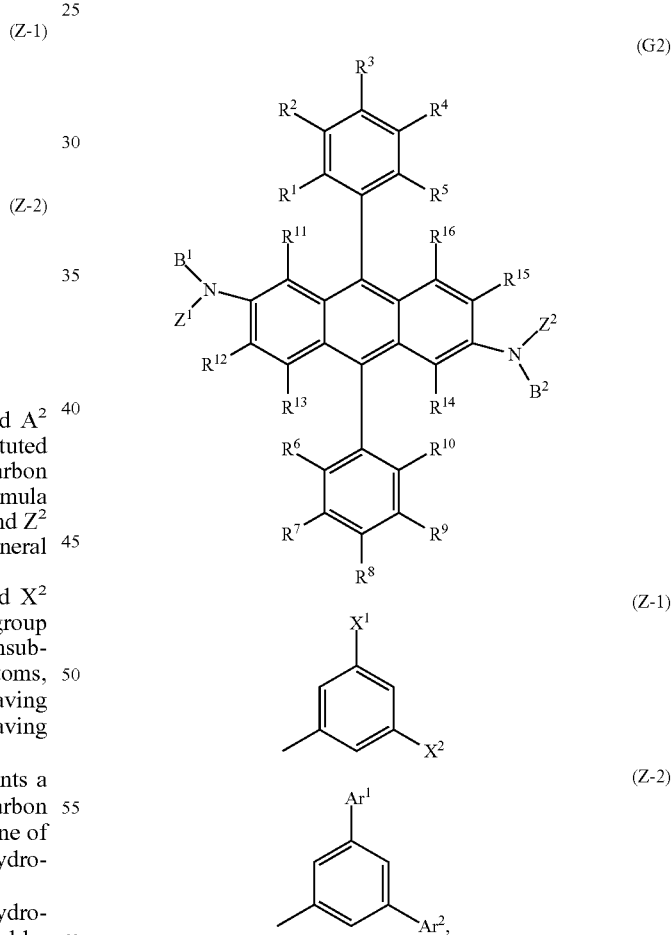

wherein in General Formula (G2), each of $B^1$ and $B^2$ independently represents a substituted or unsubstituted condensed heteroaromatic ring having 3 to 30 carbon atoms; and each of $Z^1$ and $Z^2$ independently has a structure represented by General Formula (Z-1) or General Formula (Z-2), wherein in General Formula (Z-1), each of $X^1$ and $X^2$ independently represents any one of an alkyl group having 3 to 10 carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms, wherein each of $Ar^1$ and $Ar^2$ independently represents a substituted or unsubstituted aromatic hydrocarbon group having 6 to 13 carbon atoms, and at least one of $Ar^1$ and $Ar^2$ represents a substituted aromatic hydrocarbon group having 6 to 13 carbon atoms, wherein a substituent of the substituted aromatic hydrocarbon group having 6 to 13 carbon is represented by any one of an alkyl group having 3 to 10 carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms, wherein each of $R^1$ to $R^{16}$ independently represents any one of hydrogen, an alkyl group having 3 to 10 carbon atoms, a substituted or unsubstituted cycloalkyl group having 3 to 10 carbon atoms, a trialkylsilyl group having 3 to 12 carbon atoms, and a substituted or unsubstituted aryl group having 6 to 25 carbon atoms, and wherein the substituted or unsubstituted condensed heteroaromatic ring having 3 to 30 carbon atoms represents a condensed heteroaromatic ring including a pyrrole ring.

6. A light-emitting device comprising an EL layer between a pair of electrodes,
wherein the EL layer comprises a light-emitting layer, and
wherein the light-emitting layer comprises the compound according to claim 5.

7. A light-emitting device comprising an EL layer between a pair of electrodes,
wherein the EL layer comprises a light-emitting layer, and
wherein the light-emitting layer comprises a phosphorescent material and the compound according to claim 5.

8. A lighting device comprising:
the light-emitting device according to claim 6; and
at least one of a housing, a cover, and a support base.

9. A compound represented by General formula (G3):

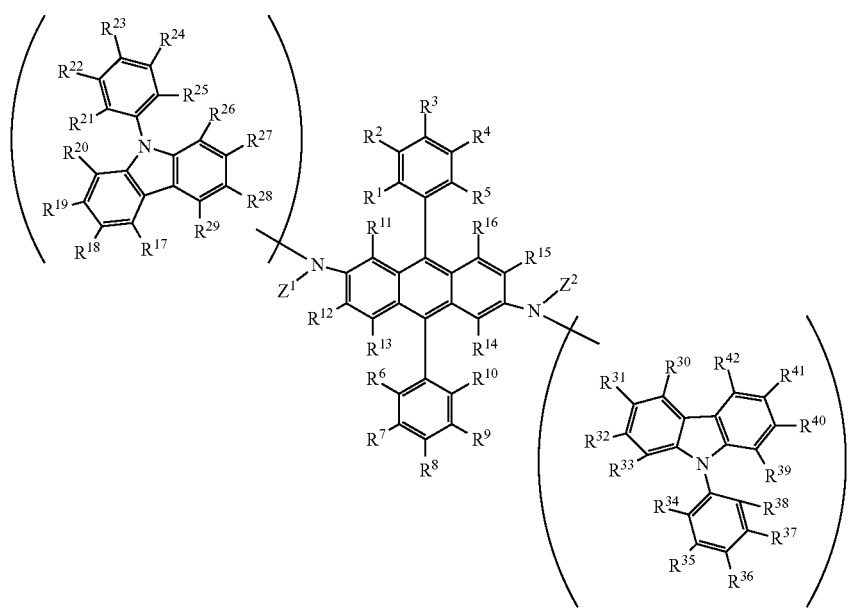

(G3)

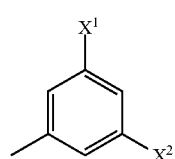

(Z-1)

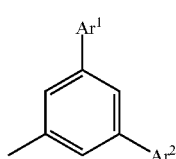

(Z-2)

wherein in General Formula (G3), each of $Z^1$ and $Z^2$ independently has a structure represented by General Formula (Z-1) or General Formula (Z-2), wherein in General Formula (Z-1), each of $X^1$ and $X^2$ independently represents any one of an alkyl group having 3 to 10 carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms, wherein each of $Ar^1$ and $Ar^2$ independently represents a substituted or unsubstituted aromatic hydrocarbon group having 6 to 13 carbon atoms, and at least one of $Ar^1$ and $Ar^2$ represents a substituted aromatic hydrocarbon group having 6 to 13 carbon atoms, wherein a substituent of the substituted aromatic hydrocarbon group having 6 to 13 carbon is represented by any one of an alkyl group having 3 to 10 carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms, and wherein each of $R^1$ to $R^{42}$ independently represents any one of hydrogen, an alkyl group having 3 to 10 carbon atoms, a substituted or unsubstituted cycloalkyl group having 3 to 10 carbon atoms, a trialkylsilyl group having 3 to 12 carbon atoms, and a substituted or unsubstituted aryl group having 6 to 25 carbon atoms; any one of $R^{17}$ to $R^{29}$ is bonded to a nitrogen atom that is bonded to $Z^1$; and any one of $R^{30}$ to $R^{42}$ is bonded to a nitrogen atom that is bonded to $Z^2$.

10. A light-emitting device comprising an EL layer between a pair of electrodes,
wherein the EL layer comprises a light-emitting layer, and
wherein the light-emitting layer comprises the compound according to claim 9.

11. A light-emitting device comprising an EL layer between a pair of electrodes,
wherein the EL layer comprises a light-emitting layer, and
wherein the light-emitting layer comprises a phosphorescent material and the compound according to claim 9.

12. A lighting device comprising:
the light-emitting device according to claim 10; and
at least one of a housing, a cover, and a support base.

13. A compound represented by General formula (G4):

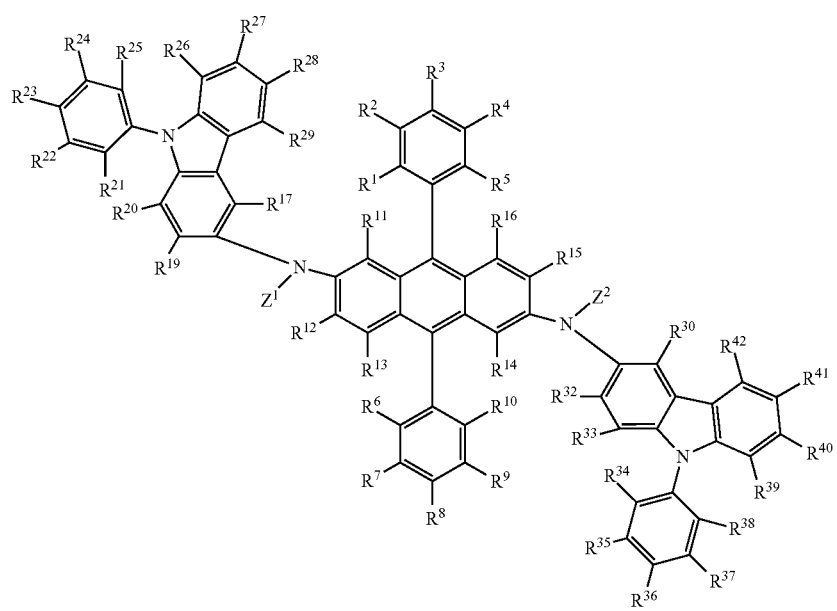

(G4)

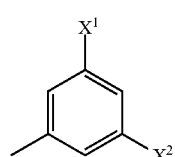

(Z-1)

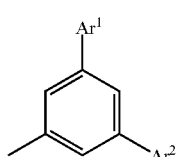

(Z-2)

wherein in General Formula (G4), each of $Z^1$ and $Z^2$ independently has a structure represented by General Formula (Z-1) or General Formula (Z-2), wherein in General Formula (Z-1), each of $X^1$ and $X^2$ independently represents any one of an alkyl group having 3 to 10 carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms, wherein each of $Ar^1$ and $Ar^2$ independently represents a substituted or unsubstituted aromatic hydrocarbon group having 6 to 13 carbon atoms, and at least one of $Ar^1$ and $Ar^2$ represents a substituted aromatic hydrocarbon group having 6 to 13 carbon atoms, wherein a substituent of the substituted aromatic hydrocarbon group having 6 to 13 carbon is represented by any one of an alkyl group having 3 to 10 carbon atoms, a substituted or unsubstituted cycloalkyl group having 3 to 10 carbon atoms, a cycloalkyl group having a bridge structure and having 7 to 10 carbon atoms, and a trialkylsilyl group having 3 to 12 carbon atoms, and wherein each of $R^1$ to $R^{17}$, $R^{19}$ to $R^{30}$, and $R^{32}$ to $R^{42}$ independently represents any one of hydrogen, an alkyl group having 3 to 10 carbon atoms, a substituted or unsubstituted cycloalkyl group having 3 to 10 carbon atoms, a trialkylsilyl group having 3 to 12 carbon atoms, and a substituted or unsubstituted aryl group having 6 to 25 carbon atoms.

14. A light-emitting device comprising an EL layer between a pair of electrodes, wherein the EL layer comprises a light-emitting layer, and wherein the light-emitting layer comprises the compound according to claim 13.

15. A light-emitting device comprising an EL layer between a pair of electrodes, wherein the EL layer comprises a light-emitting layer, and wherein the light-emitting layer comprises a phosphorescent material and the compound according to claim 13.

16. A lighting device comprising:

the light-emitting device according to claim 14; and at least one of a housing, a cover, and a support base.

17. A compound represented by Structural Formula (100):

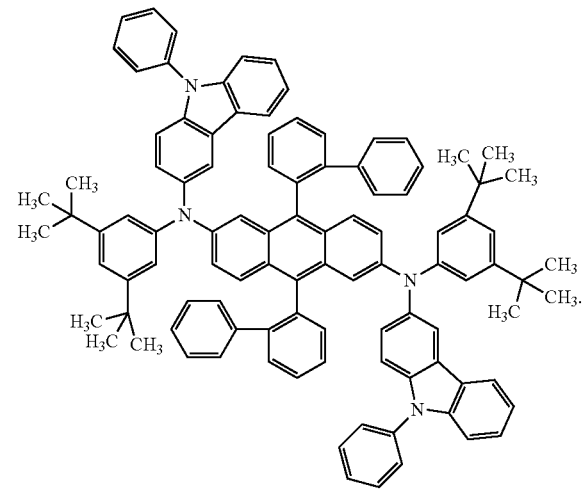

(100)

18. A light-emitting device comprising an EL layer between a pair of electrodes, wherein the EL layer comprises a light-emitting layer, and wherein the light-emitting layer comprises the compound according to claim 17.

19. A light-emitting device comprising an EL layer between a pair of electrodes, wherein the EL layer comprises a light-emitting layer, and wherein the light-emitting layer comprises a phosphorescent material and the compound according to claim 17.

20. A lighting device comprising:

the light-emitting device according to claim 18; and at least one of a housing, a cover, and a support base.

* * * * *